United States Patent
Yang et al.

(10) Patent No.: US 11,478,469 B2
(45) Date of Patent: Oct. 25, 2022

(54) COMBINATION PRODUCT OF BCL-2 INHIBITOR AND MDM2 INHIBITOR AND USE THEREOF IN THE PREVENTION AND/OR TREATMENT OF DISEASES

(71) Applicant: ASCENTAGE PHARMA (SUZHOU) CO., LTD., Suzhou (CN)

(72) Inventors: Dajun Yang, Suzhou (CN); Yifan Zhai, Suzhou (CN); Qiuqiong Tang, Suzhou (CN); Douglas Dong Fang, Suzhou (CN)

(73) Assignee: ASCENTAGE PHARMA (SUZHOU) CO., LTD., Jiangsu (CN)

( * ) Notice: Subject to any disclaimer, the term of this patent is extended or adjusted under 35 U.S.C. 154(b) by 0 days.

(21) Appl. No.: 16/648,590

(22) PCT Filed: Jul. 22, 2019

(86) PCT No.: PCT/CN2019/096968
§ 371 (c)(1),
(2) Date: Mar. 18, 2020

(87) PCT Pub. No.: WO2020/024820
PCT Pub. Date: Feb. 6, 2020

(65) Prior Publication Data
US 2022/0031694 A1    Feb. 3, 2022

(30) Foreign Application Priority Data

Jul. 31, 2018   (CN) .......................... 201810862170.9

(51) Int. Cl.
| | |
|---|---|
| A61K 31/496 | (2006.01) |
| A61P 35/02 | (2006.01) |
| A61P 35/00 | (2006.01) |
| A61K 31/407 | (2006.01) |

(52) U.S. Cl.
CPC .......... *A61K 31/496* (2013.01); *A61K 31/407* (2013.01); *A61P 35/00* (2018.01); *A61P 35/02* (2018.01)

(58) Field of Classification Search
CPC .................................................. A61K 31/496
See application file for complete search history.

(56) References Cited

U.S. PATENT DOCUMENTS

| | | | |
|---|---|---|---|
| 8,546,399 | B2 | 10/2013 | Bruncko et al. |
| 9,745,314 | B2 * | 8/2017 | Wang ....................... A61N 5/10 |
| 10,213,433 | B2 | 2/2019 | Catron et al. |
| 10,221,174 | B2 | 3/2019 | Wang et al. |
| 2010/0305122 | A1 | 12/2010 | Bruncko et al. |
| 2011/0124628 | A1 | 5/2011 | Bruncko et al. |
| 2012/0028925 | A1 | 2/2012 | Tao et al. |
| 2012/0157470 | A1 | 6/2012 | Catron et al. |
| 2015/0329541 | A1 | 11/2015 | Bruncko et al. |

FOREIGN PATENT DOCUMENTS

| | | |
|---|---|---|
| CN | 101918420 A | 12/2010 |
| CN | 105061315 A | 11/2015 |
| CN | 103402521 B | 1/2016 |
| CN | 105246882 A | 1/2016 |
| CN | 105061315 B | 10/2017 |
| CN | 106794171 B | 3/2020 |
| JP | 2013526612 A | 6/2013 |
| JP | 2013540823 A | 11/2013 |
| JP | 2013543894 A | 12/2013 |
| WO | WO 2005/049593 A2 | 6/2005 |
| WO | WO 2008/030836 A2 | 3/2008 |
| WO | WO 2008/070663 A2 | 6/2008 |
| WO | WO 2010/065824 A2 | 6/2010 |
| WO | WO 2010/065865 A2 | 6/2010 |
| WO | WO 2010/093742 A1 | 8/2010 |
| WO | WO 2010/138588 A2 | 12/2010 |
| WO | WO 2011/068863 A1 | 6/2011 |
| WO | WO 2011/149492 A1 | 12/2011 |
| WO | WO 2012/058392 A1 | 5/2012 |
| WO | WO 2012/071374 A1 | 5/2012 |
| WO | WO 2012/103059 A2 | 8/2012 |
| WO | WO 2014/113413 A1 | 7/2014 |
| WO | WO 2015/130585 A1 | 9/2015 |
| WO | WO 2015/161032 A1 | 10/2015 |
| WO | WO 2016/024230 A1 | 2/2016 |
| WO | WO 2017/037579 A1 | 3/2017 |
| WO | WO 2018/027097 A1 | 2/2018 |
| WO | WO 2020/024820 A1 | 2/2020 |
| WO | WO 2020/024826 A1 | 2/2020 |
| WO | WO 2020/024834 A1 | 2/2020 |
| WO | WO 2020/024916 A1 | 2/2020 |
| WO | WO 2020/103921 A1 | 5/2020 |

OTHER PUBLICATIONS

Ackler et al., "The Bcl-2 inhibitor ABT-263 enhances the response of multiple chemotherapeutic regimens in hematologic tumors in vivo." *Cancer Chemotherapy and Pharmacology.*, vol. 66, No. 5, (Jan. 2010), pp. 869-880.

Adams et al., "The Bcl-2 apoptotic switch in cancer development and therapy," *Oncogene*, 26(9), pp. 1324-1337, (2007).

Adams et al., "The Bcl-2 protein family: arbiters of cell survival," *Science*, 281 (5381), pp. 1322-1326, (1998).

Amundson et al., "An informatics approach identifying markers of chemosensitivity in human cancer cell lines," *Cancer Res.*, 60(21), pp. 6101-6110, (2000).

Bai L., et al., "BM-1197: A Novel and Specific Bcl-2/Bcl-xL Inhibitor Inducing Complete and Long-Lasting Tumor Regression In Vivo," *PloS ONE*, vol. 9, No. 6, (Jun. 2014), pp. 399404-e99404.

Bingham et al., "Over one hundred solvates of sulfathiazole," *Chem. Commun.*, pp. 603-604, (2001).

(Continued)

*Primary Examiner* — Brian J Davis
(74) *Attorney, Agent, or Firm* — Barnes & Thornburg, LLP

(57) ABSTRACT

Provided herein is a combination product comprising a Bcl-2 inhibitor and an MDM-2 inhibitor, the combination product providing a use in the prevention and/or treatment of diseases (e.g., cancer).

10 Claims, 5 Drawing Sheets

(56) References Cited

OTHER PUBLICATIONS

Bogenberger et al., "Combined venetoclax and alvocidib in acute myeloid leukemia," Oncotarget., vol. 8, No. 63, (Nov. 2017), pp. 107206-107222.
Caira et al., "Preparation and crystal characterization of a polymorph, a monohydrate, and an ethyl acetate solvate of the antifungal fluconazole," J. Pharm. Sci., 93(3), pp. 601-611, (2004).
Cang et al., "ABT-199 (venetoclax) and BCL-2 inhibitors in clinical development," J. Hematol. Oncol., 8, pp. 129, (2015).
Chen et al., "The Bcl-2/Bcl-X-L/Bcl-w Inhibitor, Navitoclax, Enhances the Activity of Chemotherapeutic Agents In Vitro and In Vivo," Molecular Cancer Therapeutics., vol. 11, No. 12, (Sep. 2011), pp. 2340-2349.
Danial et al., "Cell death: critical control points," Cell, 116(2), pp. 205-219, (2004).
Dey et al., "Voruciclib, a clinical stage oral CDK9 inhibitor, represses MCL-1 and sensitizes high-risk Diffuse Large B-cell Lymphoma to BCL2 inhibition," Scientific Reports 7:18007, pp. 1-11, (2017).
Dorwald F.A., "Side Reactions in Organic Synthesis," Wiley: VCH, Weinheim, pp. IX of Preface pp. 1-15, (2005).
Huang, "Fluorescence polarization competition assay: the range of resolvable inhibitor potency is limited by the affinity of the fluorescent ligand," J. Biomol. Screen., 8(1), pp. 34-38, (2003).
Inoue-Yamauchi, Akane et al., "Targeting the differential addiction to anti-apoptotic bcl-2 family for cancer therapy," Nature Communications, vol. 8, (Jul. 2017), pp. 1-14.
International Search Report and Written Opinion for PCT/CN2019/097028, dated Oct. 22, 2019.
International Search Report and Written Opinion for PCT/CN2019/097081, dated Oct. 29, 2019.
International Search Report and Written Opinion for PCT/CN2019/098252, dated Nov. 4, 2019.
International Search Report and Written Opinion for PCT/CN2019/120144, dated Feb. 24, 2020.
International Search Report for PCT/US2017/045428, dated Nov. 17, 2017.
Kirkin et al., "The role of Bcl-2 family members in tumorigenesis," Biochem. Biophys. Acta., 1644(2-3), pp. 229-249, (2004).
Kojima et al., "Concomitant Inhibition of MDM2 and Bcl-2 Protein Function Synergistically Induce Mitochondrial Apoptosis in AML," Cell Cycle, vol. 5, Iss. 23, pp. 2778-2786, (Dec. 2006).
Lehmann, Christian et al, "Superior anti-tumor activity of the MDM2 antagonist idasanutlin and the Bcl-2 inhibitor venetoclax in p53 wild-type acute myeloid leukemia models," Journal of Hematology & Oncology, (2016), 9:50; pp. 1-13.
Metro, G. and Cappuzzo, Federico, "Emerging drugs for small-cell lung cancer," Expert Opin. Emerging Drugs, 14(4), pp. 591-606, (2009).
Moss, "Basic terminology of stereochemistry," Pure & Appl. Chem., 68(12), pp. 2193-2222, (1996).
Nakayama et al., "Targeted disruption of Bcl-2 alpha beta in mice: occurrence of gray hair, polycystic kidney disease, and lymphocytopenia," Proc. Natl. Acad. Sci. USA, 91(9), pp. 3700-3704, (1994).
Nikolovska-Coleska et al., "Development and optimization of a binding assay for the XIAP BIR3 domain using fluorescence polarization," Anal. Biochem., 332(2), pp. 261-273, (2004).

Pan et al., "Activation of p56 by Novel MDM2 Antagonist RG7388 Overcomes AML Inherent and Acquired Resistance to Bcl-2 Inhibitor ABT-199 (GDC-0199)," Blood, 124:2162; (2014).
Portell et al., "Abstract B40: Synergistic cytotoxicity of ibrutinib and the BCL2 antagonist ABT-199 in mantle cell lymphoma and chronic lymphocytic leukemia: Molecular analysis reveals mechanisms of target interactions," Hematologic Malignancies, vol. 21, Issue 17, (Sep. 2015).
Reed et al., "BCL-2 family proteins: regulators of cell death involved in the pathogenesis of cancer and resistance to therapy," J. Cell Biochem., 60(1), pp. 2332, (1996).
Reed, "Bcl-2 family proteins: strategies for overcoming chemoresistance in cancer," Adv. Pharmacol., 41, pp. 501-532, (1997).
Seymour et al., "Venetoclax plus rituximab in relapsed or refractory chronic lymphocytic leukaemia: a phase 1b study," Lancet Onco. (Feb. 2017) 18(2), pp. 230-240.
Souers et al., "ABT-199, a potent and selective BCL-2 inhibitor, achieves antitumor activity while sparing platelets," Nat. Med., 19(2), pp. 202-208, (2013).
Tse et al., "ABT-263: a potent and orally bioavailable Bcl-2 family inhibitor," Cancer Res., 68(9), pp. 3421-3428, (2008).
Van Delft et al., "The BH3mimetic ABT-737 targets selective Bcl-2 proteins and efficiently induces apoptosis vai Bak/Bax if Mcl-1 is neutralized," Cancer Cell, 10(5), pp. 389-399, (2006).
Van Goethem et al., "Dual targeting of MDM2 and BCL2 as a therapeutic strategy in neuroblastoma," Oncotarget, vol. 8, No. 34, (2017), pp. 57047-57057.
Van Tonder et al., "Preparation and physicochemical characterization of 5 niclosamide solvates and 1 hemisolvate," AAPS PharmSciTech., 5(1), E12, (2004).
Venclexta, Venclexta tablets label, Translation (Dec. 14, 2017).
Venkatesh, J., "Role of the Development Scientist in Compound Lead Selection and Optimizatin" J. Pharm. Sci., vol. 89, No. 2, pp. 145-154, (2000).
Willis et al., "Apoptosis initiated when BH3 ligands engage multiple Bcl-2 homologs, not Bax or Bak," Science, 315(5813), pp. 856-859, (2007).
Written Opinion of the International Searching Authority for PCT/US2017/045428, dated Nov. 17, 2017.
Zelenetz et al., "Results of a Phase 1b Study of Venetoclax Plus R- or G- CHOP in Patients with B-Cell Non-Hodgkin Lymphoma," Blood, (Dec. 2016), vol. 128(22), pp. 3032-3035.
Zhang, "Apoptosis-based anticancer drugs," Nat. Rev. Drug Discov., 1(2), pp. 101-102, (2002).
Zinzani et al., "Phase 2 Study of Venetoclax Plus Rituximab or Randomized Ven Plus Bendamustine+Rituximab (BR) Versus BR in Patients ith Relapsed/Refractory Follicular Lymphoma: Interim Data," Blood, (Dec. 2016), vol. 128(22), pp. 617-620.
Aguilar et al., "Discovery of 4-((3'R,4'S,5'R)-6"-Chloro-4' -(3-chloro-2-fluorophenyl)-1'-ethyl-2"—oxodispiro[cyclohexane-1,2'—pyrrolidine-3',3" -indoline]-5'-carboxamido)bicycle[2,2,2]octane-1-carboxylic Acid (AA-115/APG-115): A Potent and Orally Active Murine Double Minute 2 (MDM2) Inhibitor in Clinical Development," J. Med. Chem. 2017, 60, pp. 2819-2839.
International Search Report and Written Opinion for PCT/CN2019/096968, dated Oct. 22, 2019.

* cited by examiner

A.

B.

A.

B.

COMBINATION PRODUCT OF BCL-2 INHIBITOR AND MDM2 INHIBITOR AND USE THEREOF IN THE PREVENTION AND/OR TREATMENT OF DISEASES

CROSS-REFERENCE TO RELATED APPLICATIONS

This application is a national phase application of PCT/CN2019/096968, filed Jul. 22, 2019, which application claims the benefit of and priority to Chinese Patent Application No. 201810862170.9, filed Jul. 31, 2018, the entire contents of each of which are incorporated by reference herein.

TECHNICAL FIELD

The invention belongs to the technical field of medicine, and particularly relates to a combined product comprising a Bcl-2 inhibitor and an MDM2 inhibitor and a use thereof in the prevention and/or treatment of diseases (for example, cancer).

BACKGROUND ART

Apoptosis (programmed cell death) is a natural pathway for the body to clear abnormal or unwanted cells, which can cause various diseases such as cancer if affected.

Anti-apoptotic Bcl-2 proteins are associated with many diseases. Bcl-2 family proteins are key regulators in the mitochondria-mediated apoptotic pathway. Escape from apoptosis is one of the characteristics of human cancer and is a common cause of clinical drug resistance.

P53 tumor suppressor plays an important role in controlling cell cycle progression, aging and apoptosis (Vogelstein et al, Nature 408: 307 (2000); Goberdhan, Cancer Cell 7: 505 (2005)). MDM2 and p53 are part of a self-regulating feedback loop (Wu et al., Genes Dev. 7: 1126 (1993)). MDM2 is transcriptionally activated by p53 and MDM2, and in turn, inhibits p53 activity by at least three mechanisms (Wu et al, Genes Dev. 7: 1126 (1993)). First, the MDM2 protein binds directly to the p53 transactivation domain and thus inhibits p53-mediated transactivation. Second, the MDM2 protein contains a nuclear export signal sequence and, when bound to p53, induces nuclear export of p53, thereby preventing p53 from binding to the targeted DNA. Third, the MDM2 protein is an E3 ubiquitin ligase and, when bound to p53, promotes p53 degradation.

With the advancement of molecular biology, molecular targeting therapy has become a hotspot in medical researches (especially tumor research). The biological behavior of most tumors is not dominated by a single signaling pathway, but multiple signaling pathways. Thus, there is a need in the art for protocols and products for the combination of different target proteins and/or different signaling pathways that are capable of reducing the dose of single drug, reducing single drug side effects and/or acting in a synergistic manner for the purpose of preventing and/or treating diseases.

Contents of the Invention

In order to meet the needs in the prior art, the present invention provides a combination product comprising a Bcl-2 inhibitor and an MDM2 inhibitor and its use in the treatment and/or prevention of diseases (for example, cancer).

In particular, a first aspect of the invention relates to a combination product comprising a Bcl-2 inhibitor and an MDM2 inhibitor.

In some embodiments, the Bcl-2 inhibitor is a compound of Formula I-A, or a pharmaceutically acceptable salt thereof:

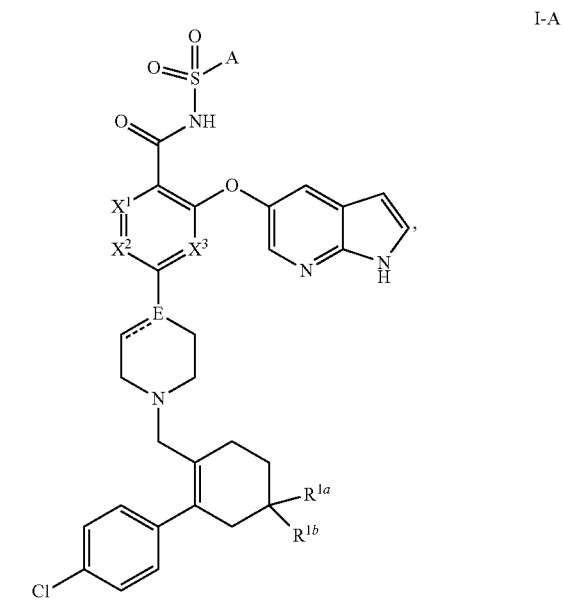

I-A wherein:
A is

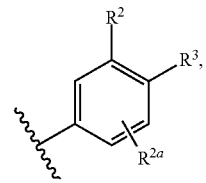

A-1

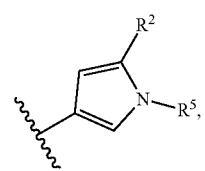

A-2

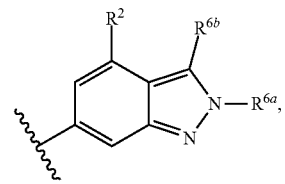

A-3

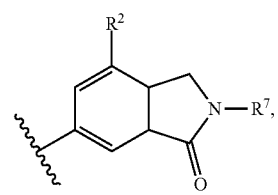

A-4

-continued

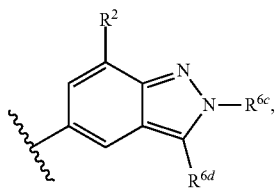
A-5

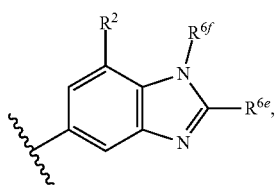
A-6

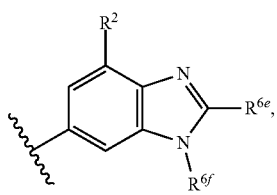
A-7

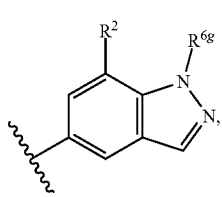
A-8

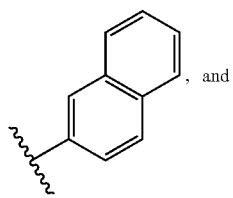
A-9

, and

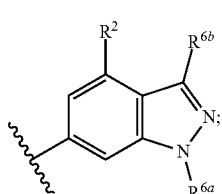
A-10

E is a carbon atom and --- is a double bond; or
E is a —C(H)— and --- is a single bond; or
E is a nitrogen atom and --- is a single bond;
X1, X2 and X3 are each independently selected from the group consisting of —CR8═ and —N═;
R1a and R1b taken together with the carbon atom to which they are attached form a 3-, 4-, or 5-membered optionally substituted aliphatic ring; or
R1a and R1b taken together with the carbon atom to which they are attached form a 4- or 5-membered optionally substituted heterocyclo;
R2 is selected from the group consisting of —NO2, —SO2CH3, and —SO2CF3;
R2a is selected from the group consisting of hydrogen and X;
R3 is selected from the group consisting of hydrogen, —CN, —C≡CH, and —N(R4a)(R4b);

R4a is selected from the group consisting of optionally substituted C1-6 alkyl, optionally substituted C3-6 cycloalkyl, heterocyclo, heteroalkyl, cycloalkylalkyl, and heterocycloalkyl;
R4b is selected from the group consisting of hydrogen and C1-4 alkyl;
R5 is selected from the group consisting of optionally substituted C1-6 alkyl, heterocyclo, cycloalkylalkyl, and heterocycloalkyl;
R6a, R6c, R6e, R6f, and R6g are each independently selected from the group consisting of hydrogen, optionally substituted C1-6 alkyl, optionally substituted C3-6 cycloalkyl, optionally substituted aryl, optionally substituted heteroaryl, heterocyclo, heteroalkyl, cycloalkylalkyl, and heterocycloalkyl;
R6b and R6d are each independently selected from the group consisting of hydrogen, C1-4 alkyl, and halogen;
R7 is selected from the group consisting of optionally substituted C1-6 alkyl, heterocyclo, heteroalkyl, cycloalkylalkyl, and heterocycloalkyl; and
R8 is selected from the group consisting of hydrogen and halogen.

In some embodiments, the MDM2 inhibitor is selected from the group consisting of: APG-115, SAR405838, RG7112, RG7388 (Idasanutlin), MI-773, Nutlin 3, Nutlin 3a, Nutlin 3b, HDM201, Kevetrin hydrochloride, MX69, NVP-CGM097, NVP-CGM097 sulfate, Nutlin 3b, R08994, YH239-EE, NVP-CGM097 stereoisomer, AMG 232, Triptolide, NSC59984, PRIMA-1, NSC66811, NSC207895, Serdemetan (JNJ 26854165), R5C3, Caylin-1, Caylin-2, HLI373, NSC319726, YH239-EE, Tenovin-1. Preferably, the MDM2 inhibitor is APG-115 having the following structure:

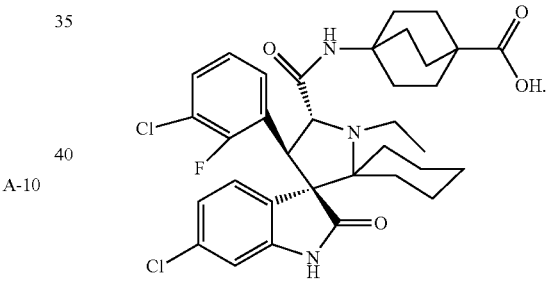

In some embodiments, the MDM2 inhibitor is selected from the group

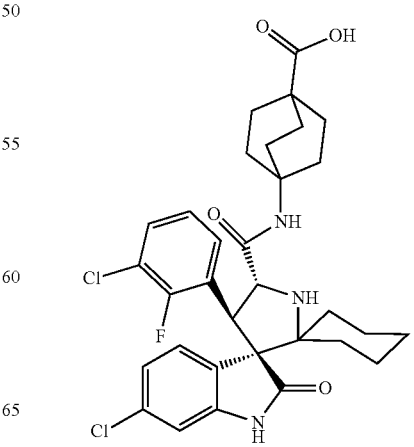

-continued
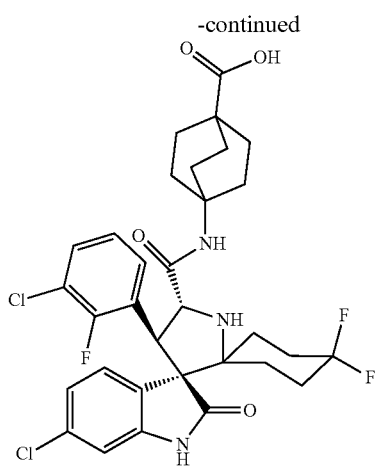
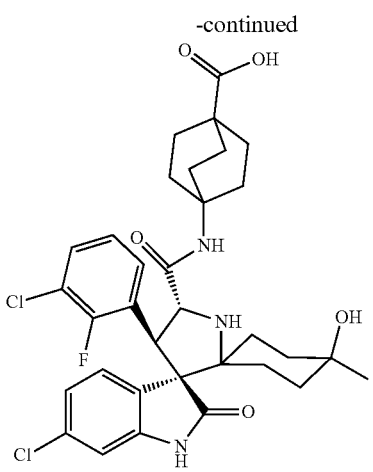
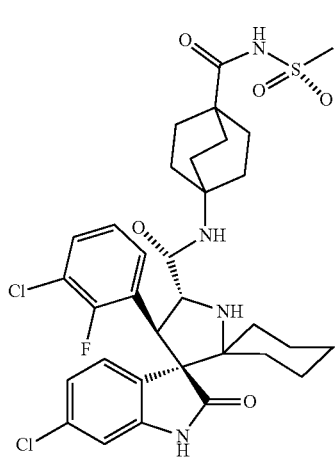
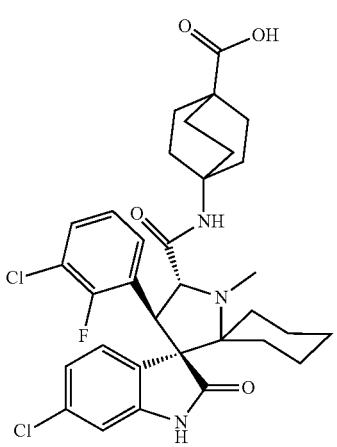
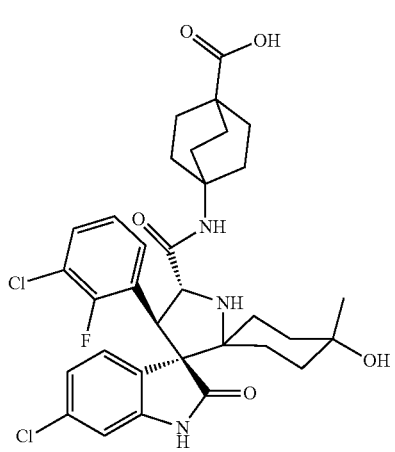
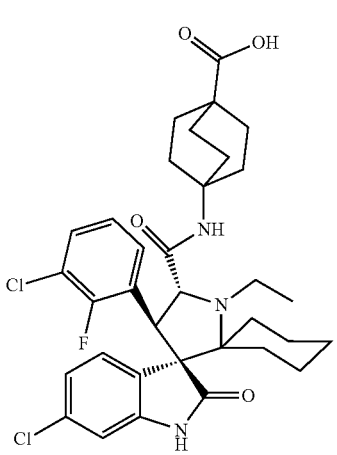

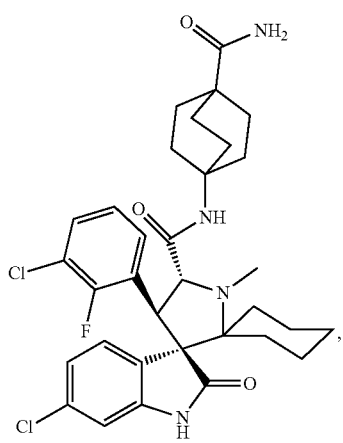
consisting of DS-3032b, BI-907828, ALRN-6924 or UBX0101.
In some embodiments, the Bcl-2 inhibitor is selected from the group consisting of a compound or a pharmaceutically acceptable salt or solvate thereof:
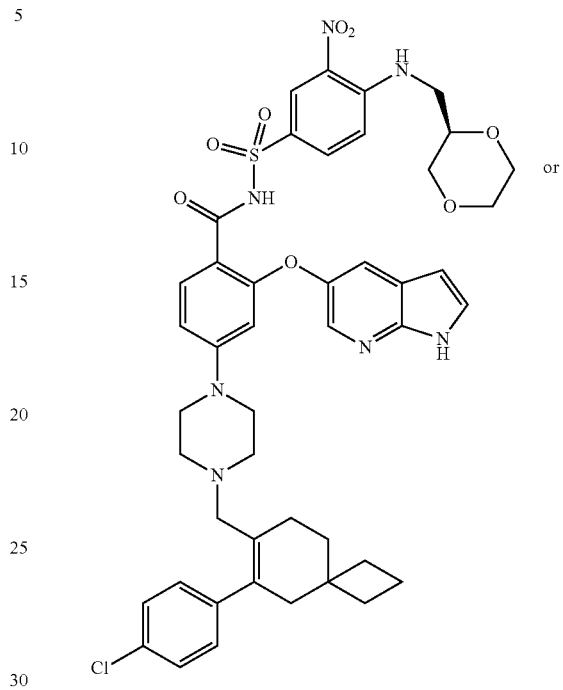
or
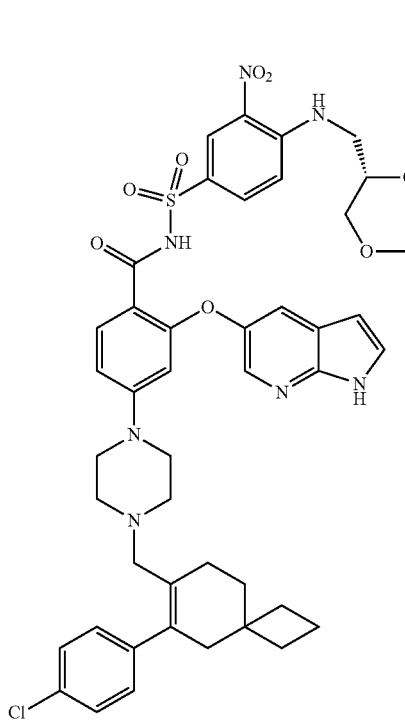
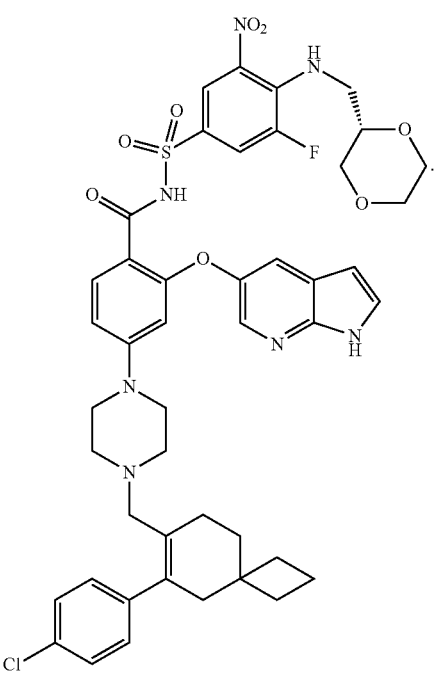 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

In some embodiments, the Bcl-2 inhibitor is the following compound or a pharmaceutically acceptable salt or solvate thereof:

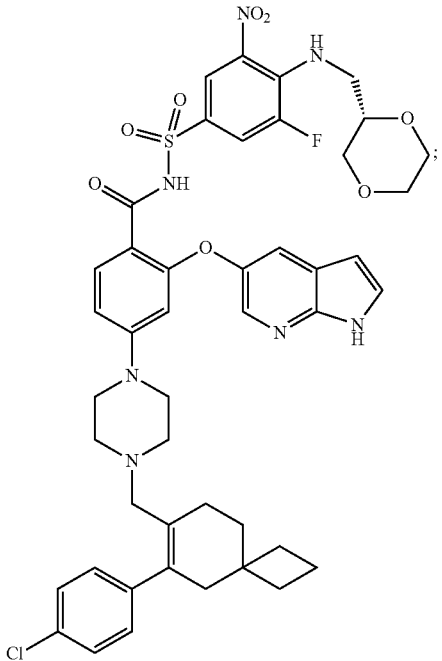 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

and wherein the MDM2 inhibitor is APG-115 or a pharmaceutically acceptable salt or solvate thereof, having the following structure:

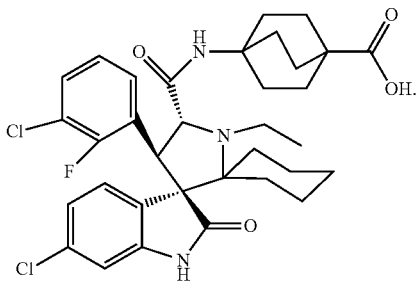 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

In some embodiments, the combination product is in the form of a pharmaceutical composition.

In some embodiments, the Bcl-2 inhibitor and the MDM2 inhibitor are each in a separate preparation.

In some embodiments, the Bcl-2 inhibitor and the MDM2 inhibitor are administered simultaneously or sequentially.

In some embodiments, the combination product further comprises a pharmaceutically acceptable carrier, diluent or excipient.

In some embodiments, the combination product is in the form of tablet, capsule, granule, syrup, powder, lozenge, sachet, cachet, elixir, suspension, emulsion, solution, syrup, aerosol, ointment, cream and injection.

A second aspect of the invention relates to the use of a Bcl-2 inhibitor and an MDM2 inhibitor in the manufacture of a medicament for the prevention and/or treatment of a disease, in which the disease is a cancer.

A third aspect of the invention relates to a combination product for preventing and/or treating a disease, in which the combination product comprises a Bcl-2 inhibitor and an MDM2 inhibitor, and the disease is a cancer.

A fourth aspect of the invention relates to a method of preventing and/or treating a disease comprising administering to a subject in need thereof a prophylactically and/or therapeutically effective amount of a Bcl-2 inhibitor and an MDM2 inhibitor, wherein the disease is a cancer.

In some embodiments, the cancer is a hematological malignancy. The hematological malignancy is selected from the group consisting of non-Hodgkin's lymphoma (NHL), diffuse large B-cell lymphoma (DLBCL), follicular lymphoma (FL), acute myeloid leukemia (AML), acute lymphoblastic leukemia (ALL), chronic lymphocytic leukemia (CLL), multiple myeloma (MM).

In some embodiments, the cancer is selected from the group consisting of non-Hodgkin's lymphoma (NHL), diffuse large B-cell lymphoma (DLBCL), follicular lymphoma (FL), acute myeloid leukemia (AML), acute lymphoblastic leukemia (ALL), chronic lymphocytic leukemia (CLL), multiple myeloma (MM), non-small cell lung cancer (NSCLC).

In some embodiments, the Bcl-2 inhibitor or a pharmaceutically acceptable salt or solvate thereof is administered in an amount from about 0.0025 to 1500 mg/day.

In some embodiments, the MDM2 inhibitor or a pharmaceutically acceptable salt or solvate thereof is administered in an amount from about 0.005 to 500 mg/day.

BRIEF DESCRIPTION OF DRAWINGS

FIG. 5A shows the bioluminescence signals in the bioluminescence measurements for vehicle, compound 6, APG-115 and the combination, respectively. FIG. 5B shows the plot of bioluminescence vs days of treatment for vehicle, compound 6, APG-115 and the combination, respectively.

DEFINITIONS

Figure 1:
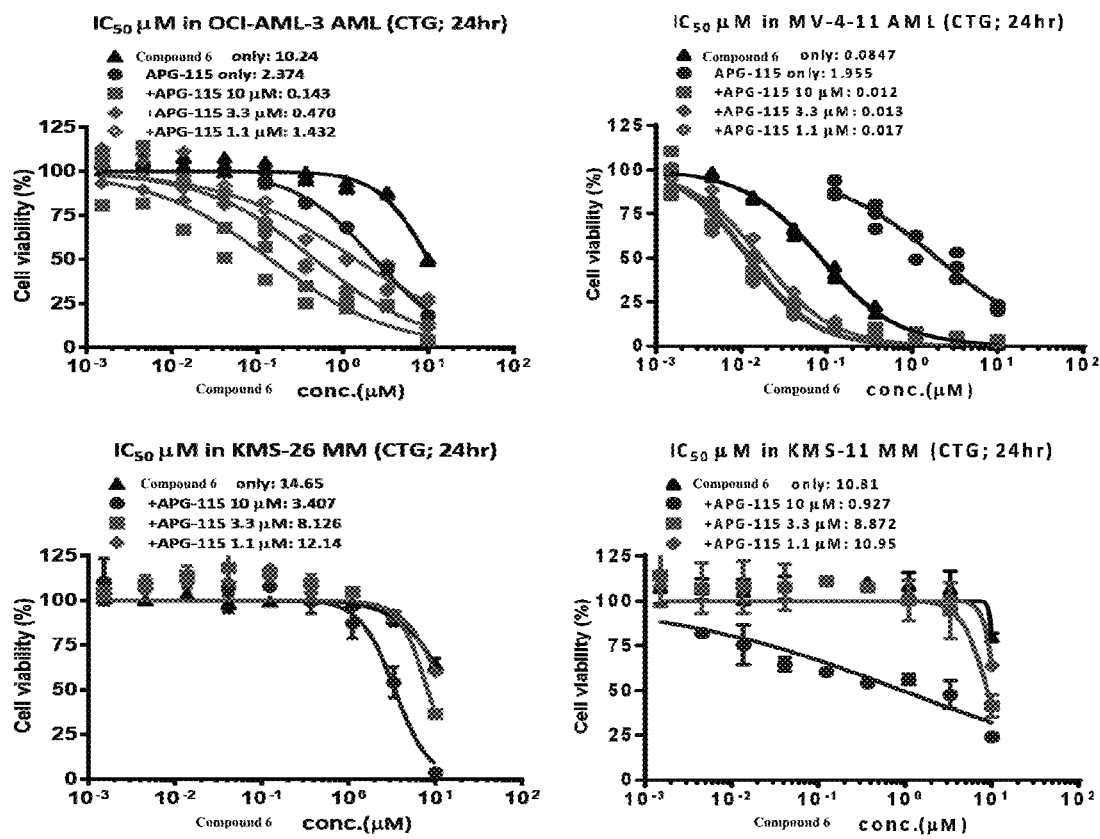
FIG. 1 shows the cell viability (%) values of Compound 6 alone and the combination of Compound 6 and APG-115 in the following malignant tumor cells in the CTG experiment: OCI-AML-3 (acute myeloid leukemia (AML)), MV-4-11 (acute myeloid leukemia (AML)), KMS-26 (multiple myeloma (MM)), KMS-11 (multiple myeloma (MM)).

The term "MDM2 inhibitor" as used herein refers to a substance that competes for binding to MDM2, a substance that affects the binding of MDM2 to a p53 protein, a substance that inhibits MDM2 activity, or a substance that degrades MDM2, or a gene tool that lowers MDM2 level.

The term "pharmaceutically acceptable salt" as used herein, refers to a salt of a free acid or a free base, usually prepared by reacting the free base with a suitable organic or inorganic acid or by reacting the acid with a suitable organic or inorganic base. This term can be used in any of the compounds of the invention. Representative salts include: acetate, besylate, benzoate, bicarbonate, hydrogen sulfate, hydrogen tartrate, borate, bromide, calcium edetate, camphorsulfonate, carbonate, chloride, clavulanate, citrate, dihydrochloride, edetate, ethanedisulfonate, estolate, esylate, fumarate, glucoheptonate, gluconate, glutamate, glycolylarsanilate, hexylresorcinate, hydrabamine, hydrobromide, hydrochloride, hydroxynaphthoate, iodide, isethionate, lactate, lactobionate, laurate, malate, maleate, mandelate, methanesulfonate, methylbromide, methylnitrate, methylsulfate, monopotassium maleate, mucate, naphthalenesulfonate, nitrate, N-methylglucosamine salt, oxalate, pamoate (dihydroxylnaphthalate), palmitate, pantothenate, phosphate/diphosphate, polygalacturonate, potassium salt, salicylate, sodium salt, stearate, subacetate, succinate, tannate, tartrate, teoclate, p-toluenesulfonate, triethiodide, trimethylamine salt and valerate. When an acidic substituent is present, such as —COOH, an ammonium salt, morpholine salt, sodium salt, potassium salt, barium salt, calcium salt or the like can be formed for use in a dosage form. When a basic group is present (for example, in a limonoid compound or a 1,1-dimethylbiguanide), such as an amino group or basic heteroaryl group such as a pyridyl group, an acidic salt can be formed, such as hydrochloride, hydrobromide, phosphate, sulfate, trifluoroacetate, trichloroacetate, acetate, oxalate, maleate, pyruvate, malonate, succinate, citrate, tartrate, fumarate, mandelate, benzoate, cinnamate, methanesulfonate, ethanesulfonate, picrate, and the like.

The term "prevention/preventing" as used herein refers to a compound or medicament (e.g., a combination product as claimed herein) can reduce a frequency of a symptom of a medical condition in a subject or delay the onset thereof when it is applied to a disease or condition (e.g., cancer), in comparison with a subject to which the compound or medicament is not applied.

The term "treatment/treating" as used herein refers to reducing, alleviating or ameliorating a symptoms of a disease or condition, ameliorating a symptom caused by a potential metabolism, inhibiting a disease or symptom, such as preventing a disease or a disorder from progression, ameliorating a disease or condition, causing regression of a disease or condition, alleviating a condition caused by a disease or condition, or preventing a symptom of a disease or condition.

The term "cancer" as used herein refers to a neoplasm or tumor caused by abnormal, uncontrolled cell growth. Non-limiting examples include those exemplary cancers described in the detailed description of the invention. The term "cancer" includes diseases involving both pre-malignant cancer cells and malignant cancer cells.

The term "solvate" as used herein is a combination, physical binding, and/or solvation of a compound of the invention with a solvent molecule, such as a disolvate, a monosolvate, a hemisolvate. The compounds of the present invention may be in a solvate form with a pharmaceutically acceptable solvent such as water, methanol, ethanol, etc., which does not significantly affect the pharmacological activity or toxicity of the compounds and which may act as a pharmacological equivalent.

The term "subject" as used herein refers to including humans (e.g, patients) and animals (e.g, mice, rats, dogs, cats, rabbits, chickens, monkeys, etc.). When the subject is a human patient (usually calculated as body weight of 60 kg), a dose described herein can be obtained by conversion performed with a conversion factor for an experimental animal (e.g., human dose=mouse dose/12.3) unless otherwise stated (Kin Tam. "Estimating the "First in human" dose-a revisit with particular emphasis on oncology drugs, ADMET & DMPK 1 (4) (2013) 63-75). Those of ordinary skill in the art can reasonably adjust the dose based on common sense and according to the specific weight of subject, the type and severity of disease, and other factors, and all of these adjusted technical solutions fall within the scope of the technical solutions claimed in the present invention.

The term "effective amount" or "prophylactically and/or therapeutically effective amount" as used herein refers to a sufficient amount (e.g, a dose) of a medicament or compound to be administered that will alleviate one or more symptoms of a disease or condition to be treated to some extent. The result can be a reduction and/or alleviation in the cause of the condition or the cause of disease or any other desired changes in biological system. For example, an "effective amount" for therapeutic use is an amount of a compound or medicament (e.g, a combination product as claimed herein) that provides a significant reduction in the clinical symptoms of the disease or condition without causing excessive toxic side effects.

The term "dose" as used herein refers to a weight (e.g, milligrams (mg)) of an active substance per kilogram (kg) of a subject's body weight.

The term "IC50" as used herein refers to an amount, concentration or dose of a particularly tested compound or medicament that achieves a 50% inhibition of maximum effect in an assay that measures such effect, for example inhibition of BCL-2 or MDM2.

The term "room temperature" as used herein refers to 25° C.±1° C. At the same time, if the experimental temperature is not specified, it is room temperature.

The term "about" as used herein refers to ±10%, more preferably ±5%, and most preferably ±2% of the value modified by the term, so that one of ordinary skill in the art can clearly determine the scope of the term "about" according to the modified value.

The terms "aliphatic ring", "heterocycle", "heterocycloalkyl", "heteroalkyl", "cycloalkylalkyl" and "halogen" as used herein have the ordinary meanings in the art, and a person of ordinary skill in the art will be able to understand the meaning thereof by the general knowledge or by reference to the prior art (for example, WO 2018/027097, the entire disclosure of which is incorporated herein by reference).

The term "APG-115" as used herein is a compound having the structure:

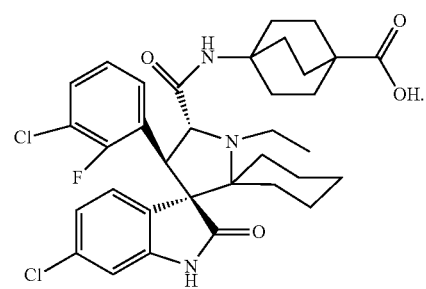 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

DETAILED DESCRIPTION OF THE INVENTION
In a first aspect of the invention relates to a combination product comprising or consisting of a Bcl-2 inhibitor and an MDM2 inhibitor.
In some embodiments, the Bcl-2 inhibitor is a compound of Formula I-A, or a pharmaceutically acceptable salt or solvate thereof:
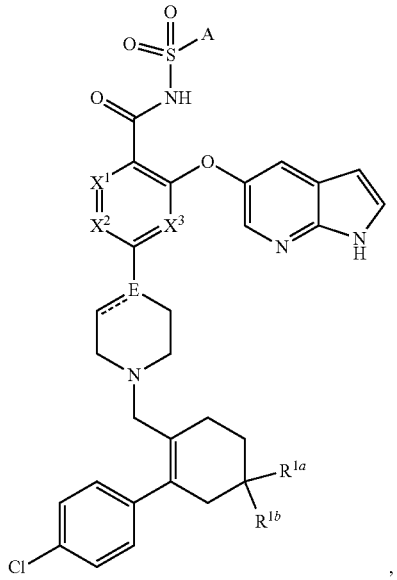
I-A
wherein:
A is
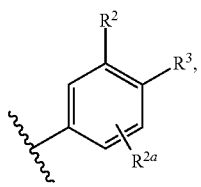
A-1
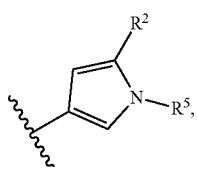
A-2
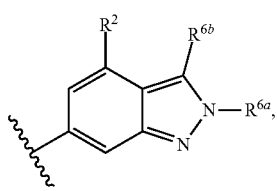
A-3
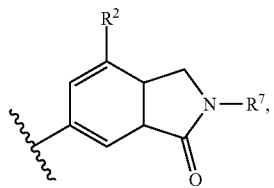
A-4
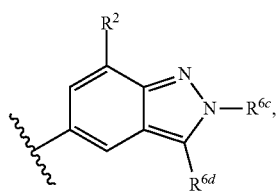
A-5
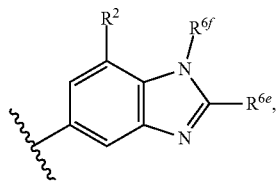
A-6
A-7
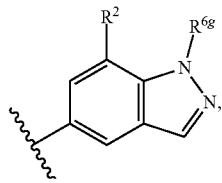
A-8
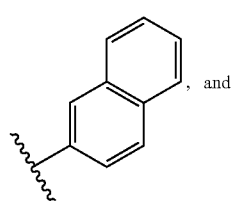, and
A-9

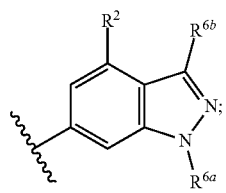

A-10

E is a carbon atom and --- is a double bond; or

E is a —C(H)— and --- is a single bond; or

E is a nitrogen atom and --- is a single bond;

X1, X2 and X3 are each independently selected from the group consisting of —CR8═ and —N═;

R1a and R1b taken together with the carbon atom to which they are attached form a 3-, 4-, or 5-membered optionally substituted aliphatic ring; or R1a and R1b taken together with the carbon atom to which they are attached form a 4- or 5-membered optionally substituted heterocyclo;

R2 is selected from the group consisting of —NO2, —SO2CH3, and —SO2CF3;

R2a is selected from the group consisting of hydrogen and X;

R3 is selected from the group consisting of hydrogen, —CN, —C≡CH, and —N(R4a)(R4b);

R4a is selected from the group consisting of optionally substituted C1-6 alkyl, optionally substituted C3-6 cycloalkyl, heterocyclo, heteroalkyl, cycloalkylalkyl, and heterocycloalkyl;

R4b is selected from the group consisting of hydrogen and C1-4 alkyl;

R5 is selected from the group consisting of optionally substituted C1-6 alkyl, heterocyclo, cycloalkylalkyl, and heterocycloalkyl;

R6a, R6c, R6e, R6f, and R6g are each independently selected from the group consisting of hydrogen, optionally substituted C1-6 alkyl, optionally substituted C3-6 cycloalkyl, optionally substituted aryl, optionally substituted heteroaryl, heterocyclo, heteroalkyl, cycloalkylalkyl, and heterocycloalkyl;

R6b and R6d are each independently selected from the group consisting of hydrogen, C1-4 alkyl, and halogen;

R7 is selected from the group consisting of optionally substituted C1-6 alkyl, heterocyclo, heteroalkyl, cycloalkylalkyl, and heterocycloalkyl; and R8 is selected from the group consisting of hydrogen and halogen.

In the above compound of Formula I-A, the "X" in the definition of variant R2a refers to halogen. Further, halogen mentioned above refers to F, Cl, Br, or I.

In some embodiments, the Bcl-2 inhibitor is a compound of Formula I-A, wherein: A is selected from the group consisting of A-1, A-2, A-3, A-4, A-5, A-6, A-7, A-8, and A-9; R4a is selected from the group consisting of optionally substituted C1-6 alkyl, heterocyclo, heteroalkyl, cycloalkylalkyl, and heterocycloalkyl; and R6a, R6c, R6e, R6f and R6g are each independently selected from the group consisting of hydrogen, optionally substituted C1-6 alkyl, heterocyclo, heteroalkyl, cycloalkylalkyl, and heterocycloalkyl.

In some embodiments, the Bcl-2 inhibitor is a compound of Formula I, or a pharmaceutically acceptable salt or solvate thereof,

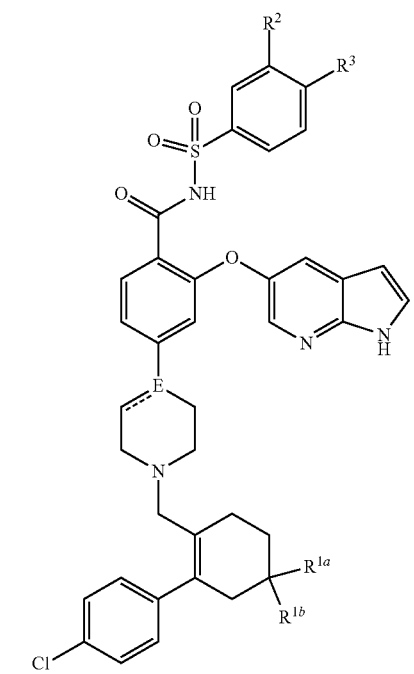

I wherein:

E is a carbon atom and --- is a double bond; or E is —C(H)— and --- is a single bond; or E is a nitrogen atom and --- is a single bond;

R1a and R1b together with the carbon atom connected thereto form a 3-, 4-, or 5-membered optionally substituted aliphatic ring; or R1a and R1b together with the carbon atom connected thereto form a 4- or 5-membered optionally substituted heterocyclo;

R2 is selected from the group consisting of —NO2, —SO2CH3, and —SO2CF3;

R3 is selected from the group consisting of hydrogen, —CN, —C≡CH, and —N(R4a)(R4b);

R4a is selected from the group consisting of optionally substituted C1-6 alkyl, heterocyclo, cycloalkylalkyl, and heterocycloalkyl;

R4b is selected from the group consisting of hydrogen and C1-4 alkyl.

In some embodiments, the Bcl-2 inhibitor is a compound of Formula II, or a pharmaceutically acceptable salt or solvate thereof,

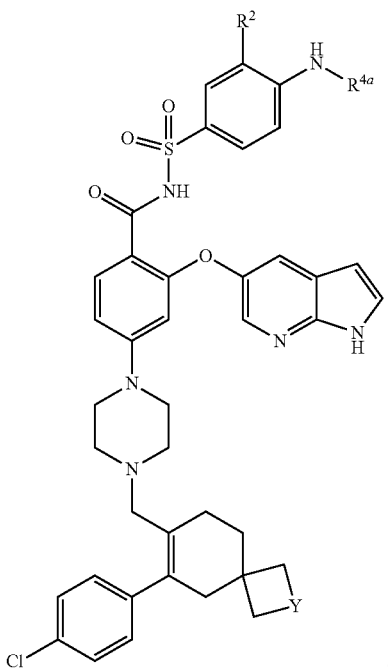

wherein Y is selected from the group consisting of —CH2- and —O—, and R2 and R4a are as defined in connection with Formula I.

In some embodiments, the Bcl-2 inhibitor is a compound of Formula III, or a pharmaceutically acceptable salt or solvate thereof,

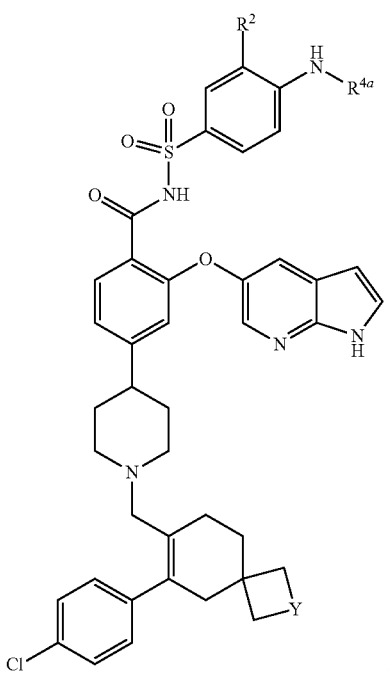

wherein Y is selected from the group consisting of —CH2- and —O—, and R2 and R4a are as defined in connection with Formula I.

In some embodiments, the Bcl-2 inhibitor is a compound of Formula IV, or a pharmaceutically acceptable salt or solvate thereof,

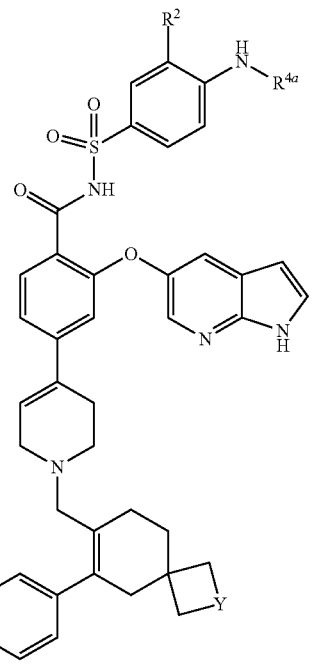

wherein Y is selected from the group consisting of —CH2- and —O—, and R2 and R4a are as defined in connection with Formula I.

In some embodiments, the Bcl-2 inhibitor is a compound of Formula V, or a pharmaceutically acceptable salt or solvate thereof,

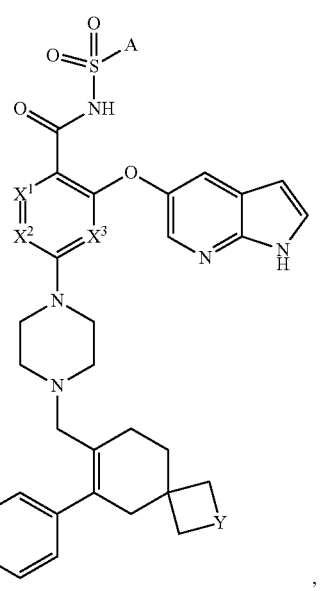

wherein Y selected from the group consisting of —CH2- and —O—, and A, X1, X2, and X3 are as defined in connection with Formula I-A.

In some embodiments, the Bcl-2 inhibitor is a compound of Formula VI, or a pharmaceutically acceptable salt or solvate thereof,

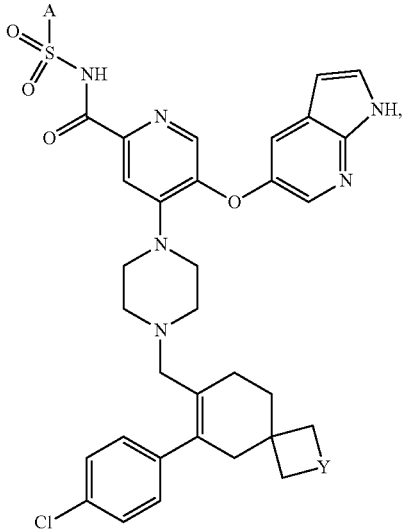

VI wherein Y selected from the group consisting of —CH2- and —O—, and A is as defined in connection with Formula I-A.

In some embodiments, the Bcl-2 inhibitor is a compound of Formula I-A, V or VI, or a pharmaceutically acceptable salt or solvate thereof, wherein A is A-1.

In some embodiments, the Bcl-2 inhibitor is a compound of Formula I-A, V or VI, or a pharmaceutically acceptable salt or solvate thereof, wherein A is A-2.

In some embodiments, the Bcl-2 inhibitor is a compound of Formula I-A, V or VI, or a pharmaceutically acceptable salt or solvate thereof, wherein A is A-3.

In some embodiments, the Bcl-2 inhibitor is a compound of Formula I-A, V or VI, or a pharmaceutically acceptable salt or solvate thereof, wherein A is A-4.

In some embodiments, the Bcl-2 inhibitor is a compound of Formula I-A, V or VI, or a pharmaceutically acceptable salt or solvate thereof, wherein A is A-5.

In some embodiments, the Bcl-2 inhibitor is a compound of Formula I-A, V or VI, or a pharmaceutically acceptable salt or solvate thereof, wherein A is A-6.

In some embodiments, the Bcl-2 inhibitor is a compound of Formula I-A, V or VI, or a pharmaceutically acceptable salt or solvate thereof, wherein A is A-7.

In some embodiments, the Bcl-2 inhibitor is a compound of Formula I-A, V or VI, or a pharmaceutically acceptable salt or solvate thereof, wherein A is A-8.

In some embodiments, the Bcl-2 inhibitor is a compound of Formula I-A, V or VI, or a pharmaceutically acceptable salt or solvate thereof, wherein A is A-9.

In some embodiments, the Bcl-2 inhibitor is a compound of Formula I-A, V or VI, or a pharmaceutically acceptable salt or solvate thereof, wherein A is A-10.

In some embodiments, the Bcl-2 inhibitor is a compound of Formula VII, or a pharmaceutically acceptable salt or solvate thereof,

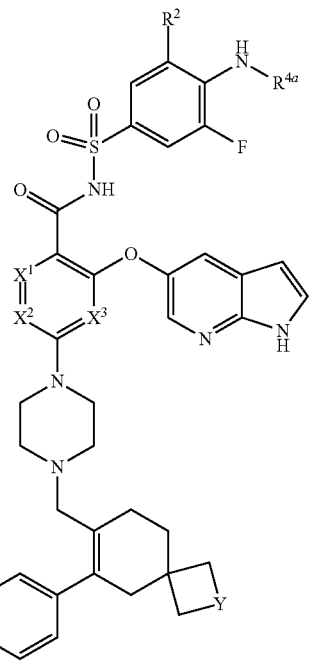

VII wherein Y selected from the group consisting of —CH2- and —O—, and X1, X2, X3, R2, and R4a are as defined in connection with Formula I-A.

In some embodiments, the Bcl-2 inhibitor is a compound of Formula I-A, V or VII, or a pharmaceutically acceptable salt or solvate thereof, wherein all X1, X2, and X3 are —CH═.

In some embodiments, the Bcl-2 inhibitor is a compound of Formula I-A, V or VII, or a pharmaceutically acceptable salt or solvate thereof, wherein X1 is —CF═, and both X2 and X3 are —CH═.

In some embodiments, the Bcl-2 inhibitor is a compound of Formula I-A, V or VII, or a pharmaceutically acceptable salt or solvate thereof, wherein both X1 and X3 are —CH═, and X2 is —CF═.

In some embodiments, the Bcl-2 inhibitor is a compound of Formula I-A, V or VII, or a pharmaceutically acceptable salt or solvate thereof, wherein both X1 and X2 are —CH═, and X3 is —CF═.

In some embodiments, the Bcl-2 inhibitor is a compound of Formula I-A, V or VII, or a pharmaceutically acceptable salt or solvate thereof, wherein X1 is —N═, and both X2 and X3 are —CH═.

In some embodiments, the Bcl-2 inhibitor is a compound of Formula I-A, V or VII, or a pharmaceutically acceptable salt or solvate thereof, wherein both X1 and X3 are —CH═, and X2 is —N═.

In some embodiments, the Bcl-2 inhibitor is a compound of Formula I-A, V or VII, or a pharmaceutically acceptable salt or solvate thereof, wherein both X1 and X2 are —CH═, and X3 is —N═.

In some embodiments, the Bcl-2 inhibitor is a compound of any one of Formulae II-VII, or a pharmaceutically acceptable salt or solvate thereof, wherein Y is —O—.

In some embodiments, the Bcl-2 inhibitor is a compound of any one of Formulae II-VII, or a pharmaceutically acceptable salt or solvate thereof, wherein Y is —CH2-.

In some embodiments, the Bcl-2 inhibitor is a compound of any one of Formulae I-A or I-VII, or a pharmaceutically acceptable salt or solvate thereof, wherein R2 is —NO2.

In some embodiments, the Bcl-2 inhibitor is a compound of any one of Formulae I-VI, or a pharmaceutically acceptable salt or solvate thereof, wherein R4a is selected from the group consisting of:

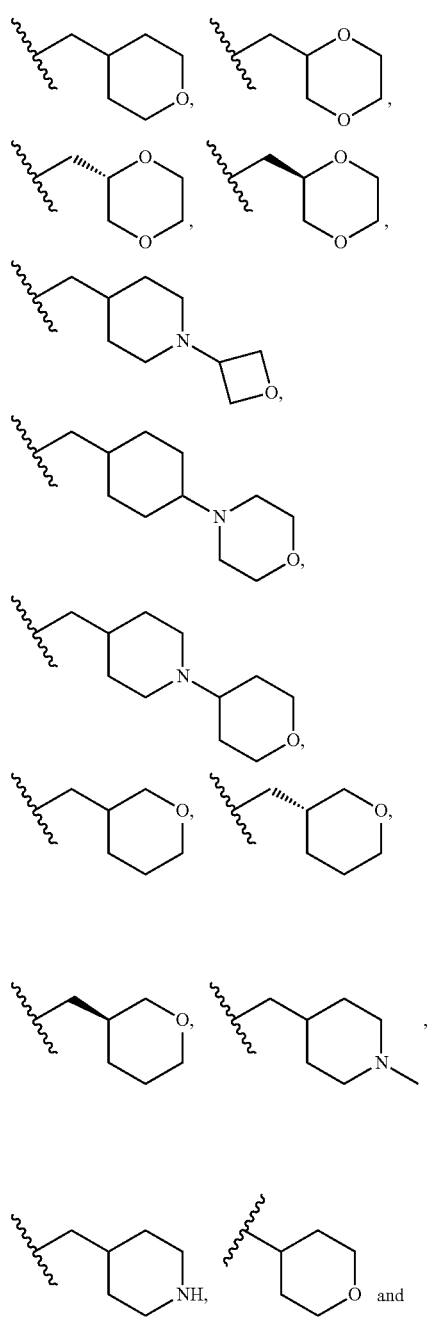

In some embodiments, the Bcl-2 inhibitor is a compound of any one of Formulae I-A or V-VII, or a pharmaceutically acceptable salt or solvate thereof, wherein R4a, R5, R6a, and R7 are each independently selected from the group consisting of:

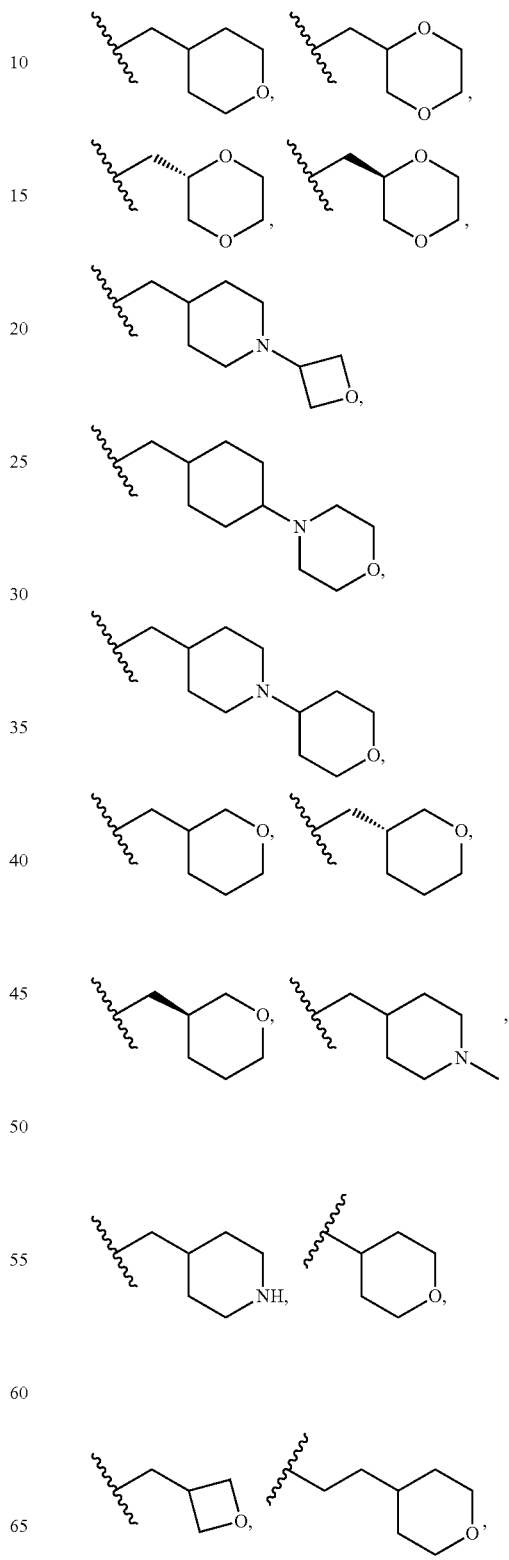

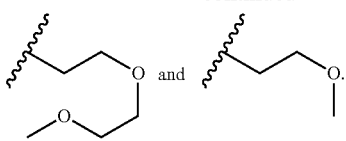

In some embodiments, the Bcl-2 inhibitor is a compound of Formula VIII, or a pharmaceutically acceptable salt or solvate thereof, wherein $R^{2a}$ is hydrogen or fluoro and $R^{4a}$ is as defined in connection with Formula I-A.

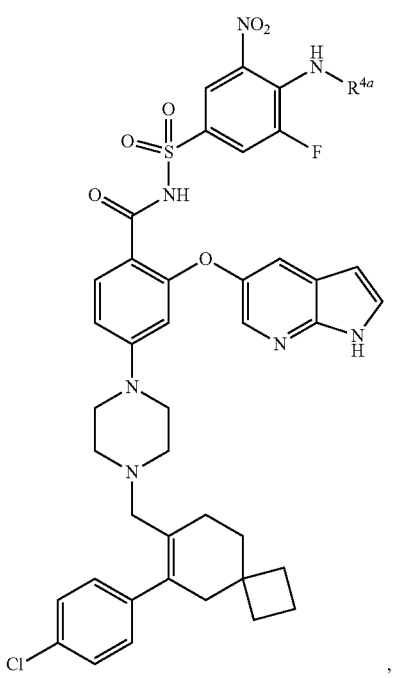

VIII

In some embodiments, the Bcl-2 inhibitor is a compound of Formula VIII, or a pharmaceutically acceptable salt or solvate thereof, wherein $R^{4a}$ is selected from the group consisting of:

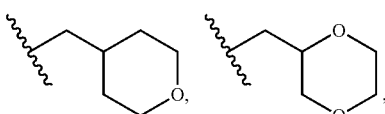

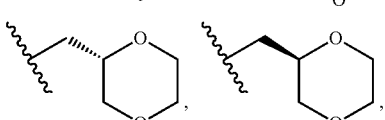

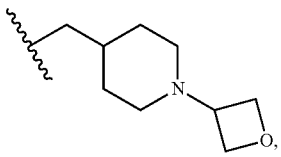

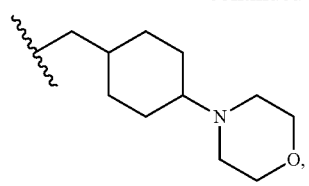

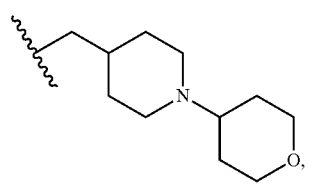

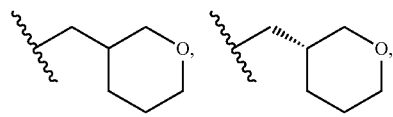

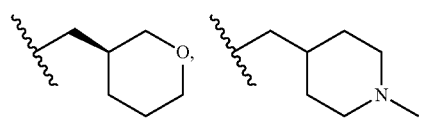

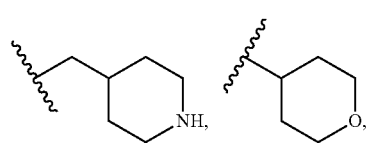

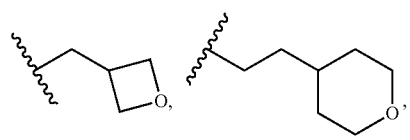

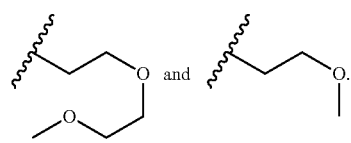

In some embodiments, the Bcl-2 inhibitor is a compound selected from one or more of the compounds of Table 1, or a pharmaceutically acceptable salt or solvate thereof.

TABLE 1

| Cpd. No. | Structure | Name |
|---|---|---|
| 1 | 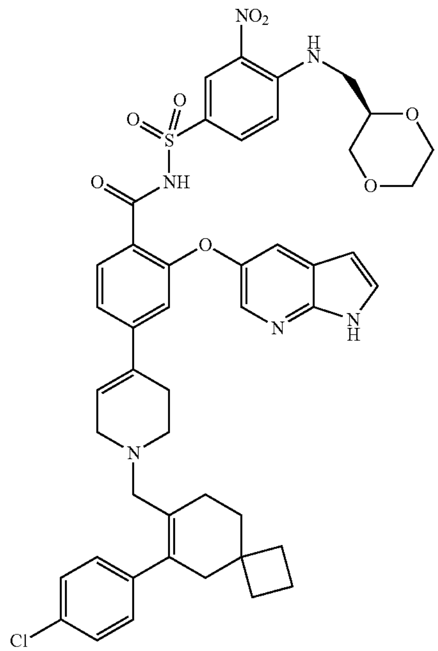 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CCC4)CC3)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)benzamide |
| 2 | 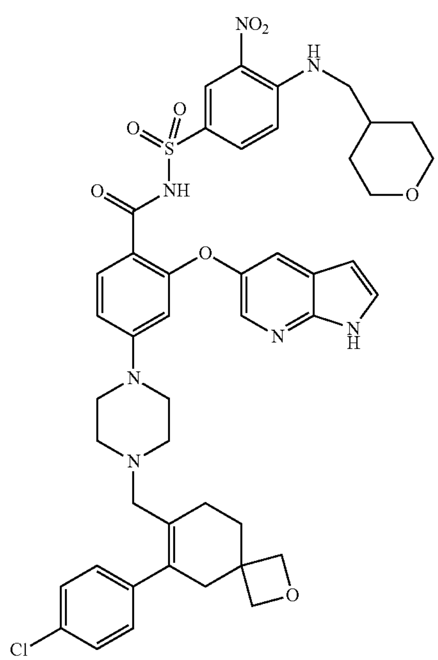 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CC3)COC4)CC2)cc1Oc1cnc2[nH]ccc2c1] | 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)-N-((3-nitro-4-(((tetrahydro-2H-pyran-4-yl)methyl)amino)phenyl)sulfonyl)benzamide |

TABLE 1-continued
| Cpd. No. | Structure | Name |
|---|---|---|
| 3 | 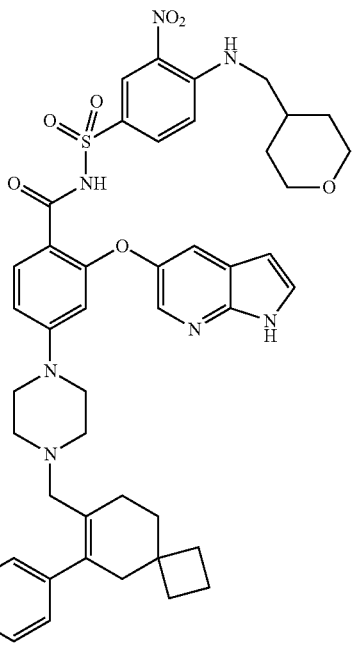 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide |
| 4 | 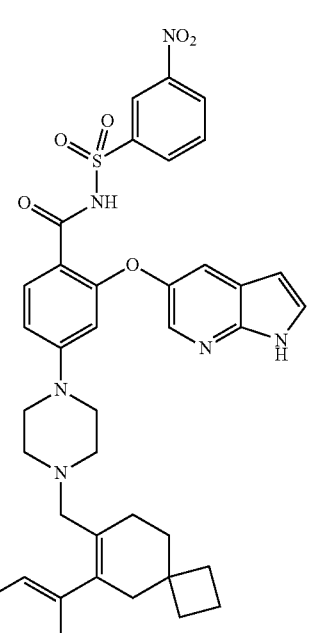 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitrophenyl)sulfonyl)benzamide |

TABLE 1-continued

| Cpd. No. | Structure | Name |
|---|---|---|
| 5 | 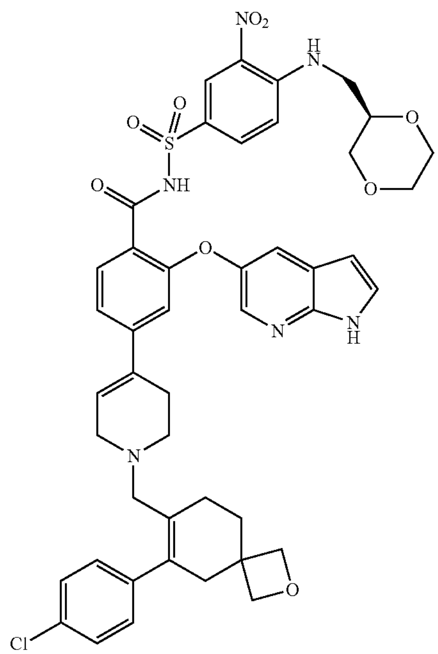 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CC3)COC4)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)benzamide |
| 6 | 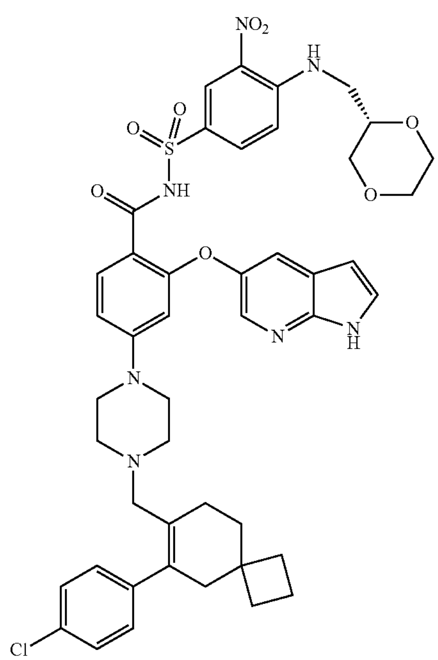 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-continued
| Cpd. No. | Structure | Name |
|---|---|---|
| 7 | 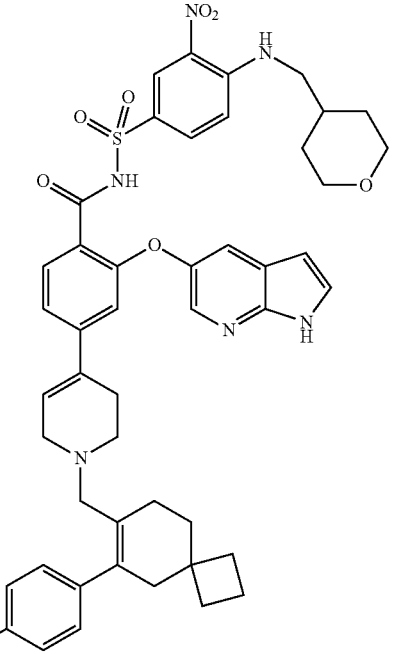 | 2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |
| 8 | 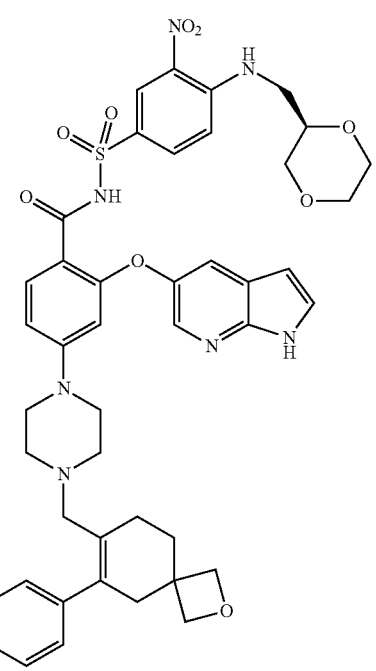 | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzamide |

TABLE 1-continued

| Cpd. No. | Structure | Name |
|---|---|---|
| 9 | 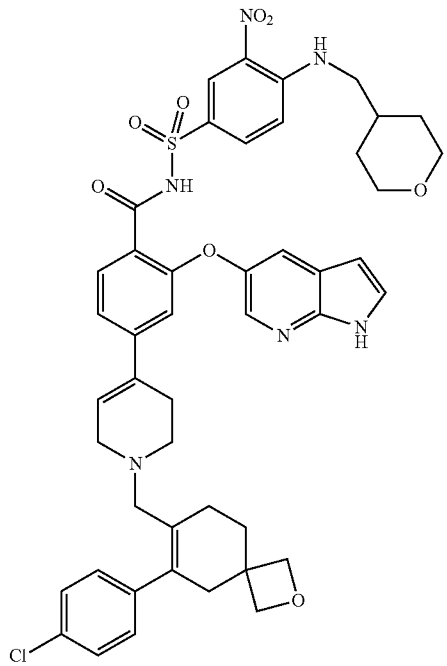 [SMILES: O=C(NS(=O)(=O)c1ccc(NCC2CCOCC2)c([N+](=O)[O-])c1)c1ccc(C2=CCN(CC3=C(c4ccc(Cl)cc4)CC4(CC3)COC4)CC2)cc1Oc1cnc2[nH]ccc2c1] | 2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |
| 10 | 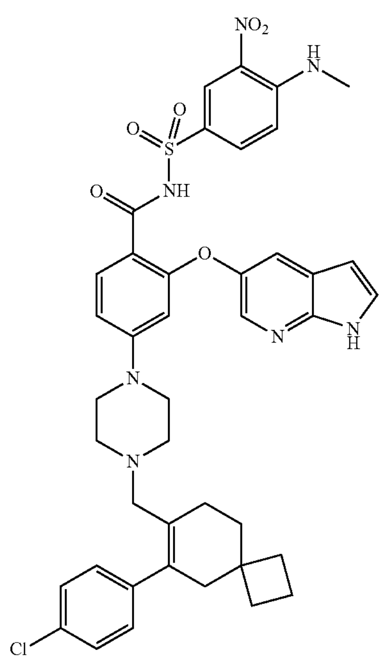 [SMILES: CNc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(methylamino)-3-nitrophenyl)sulfonyl)benzamide |

TABLE 1-continued

| Cpd. No. | Structure | Name |
|---|---|---|
| 11 | 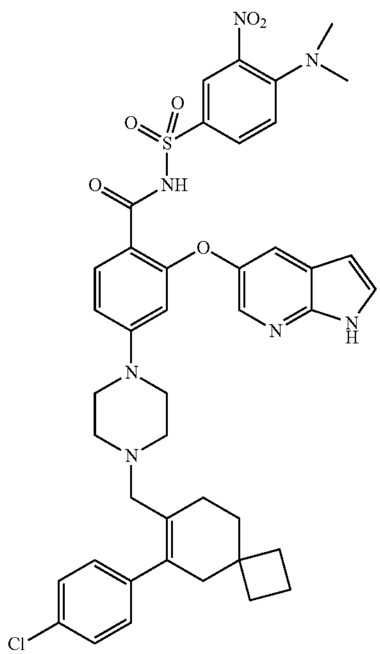 [SMILES: CN(C)c1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(dimethylamino)-3-nitrophenyl)sulfonyl)benzamide |
| 12 | 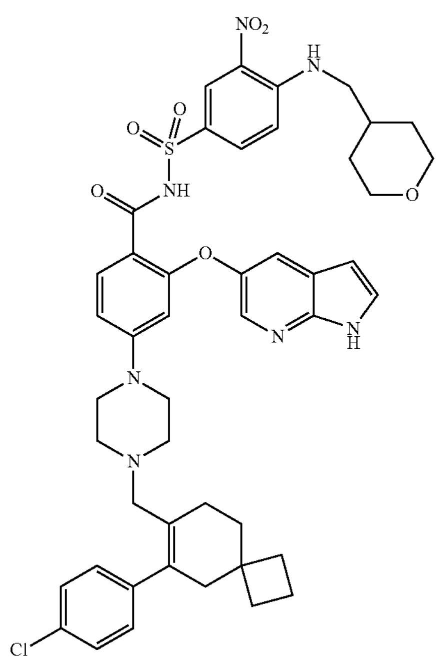 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(1-((6-(4-chlorophenyl)spiro[3.5]non-6-en-7-yl)methyl)piperidin-4-yl)-N-((3-nitro-4-(((tetrahydro-2H-pyran-4-yl)methyl)amino)phenyl)sulfonyl)benzamide |

TABLE 1-continued

| Cpd. No. | Structure | Name |
|---|---|---|
| 13 | 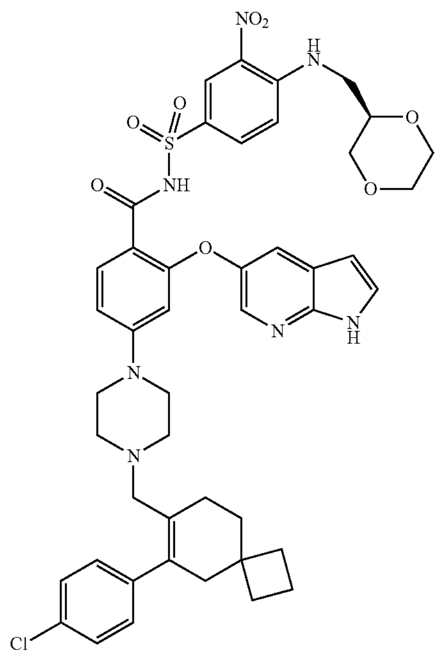 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 14 | 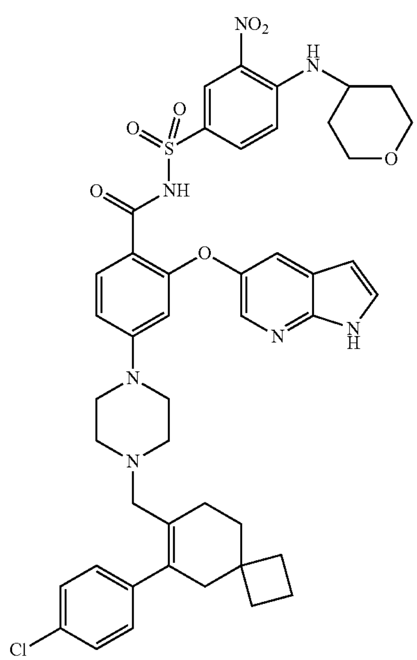 [SMILES: O=C(NS(=O)(=O)c1ccc(NC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((tetrahydro-2H-pyran-4-yl)amino)phenyl)sulfonyl)benzamide |

TABLE 1-continued
| Cpd. No. | Structure | Name |
|---|---|---|
| 15 | 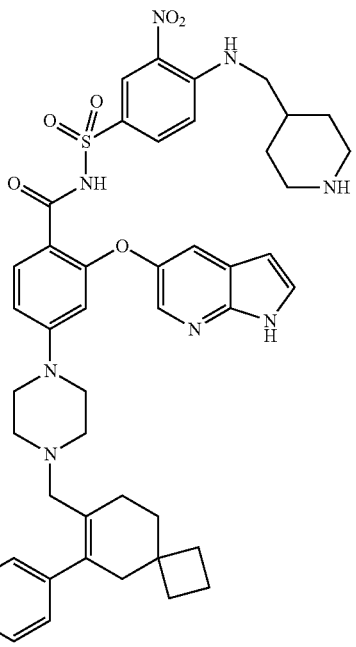 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((piperidin-4-ylmethyl)amino)phenyl)sulfonyl)benzamide |
| 16 | 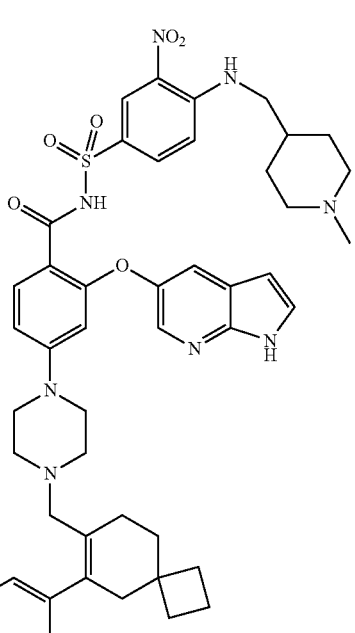 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(((1-methylpiperidin-4-yl)methyl)amino)-3-nitrophenyl)sulfonyl)benzamide |

TABLE 1-continued
| Cpd. No. | Structure | Name |
|---|---|---|
| 17 | 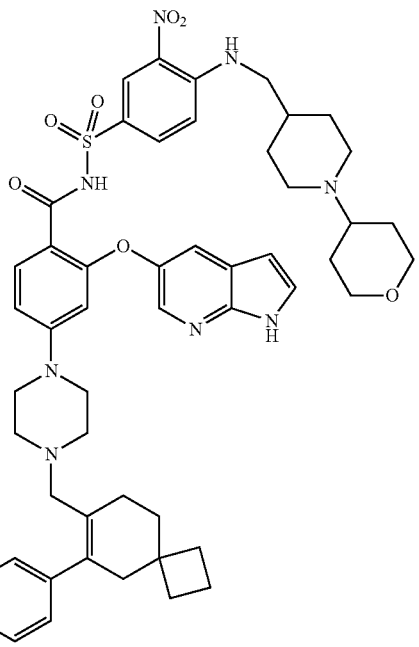 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((1-(tetrahydro-2H-pyran-4-yl)piperidin-4-yl)methyl)amino)phenyl)sulfonyl)benzamide |
| 18 | 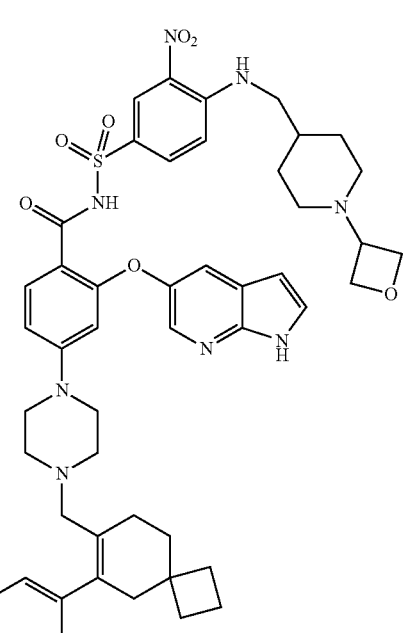 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((1-(oxetan-3-yl)piperidin-4-yl)methyl)amino)phenyl)sulfonyl)benzamide |

TABLE 1-continued
| Cpd. No. | Structure | Name |
|---|---|---|
| 19 | 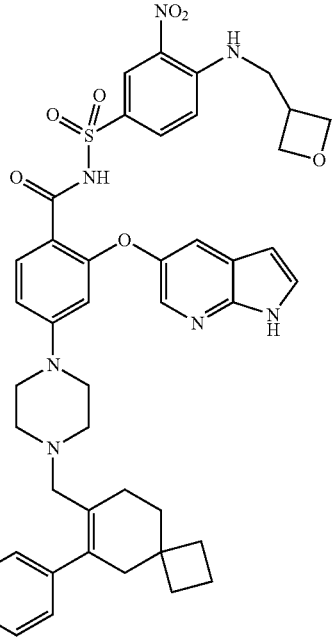 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((oxetan-3-ylmethyl)amino)phenyl)sulfonyl)benzamide |
| 20 | 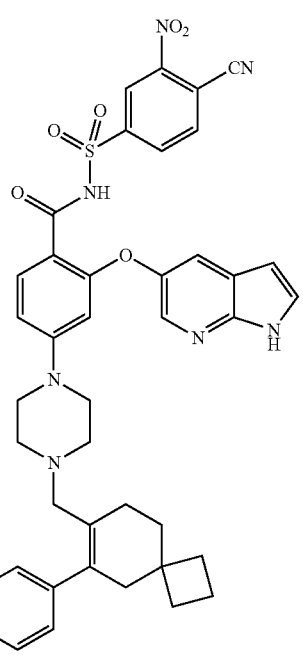 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-cyano-3-nitrophenyl)sulfonyl)benzamide |

TABLE 1-continued

| Cpd. No. | Structure | Name |
|---|---|---|
| 21 | 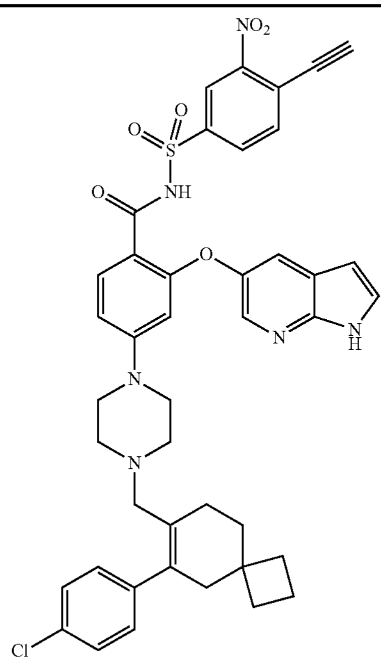 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-ethynyl-3-nitrophenyl)sulfonyl)benzamide |

In some embodiments, the Bcl-2 inhibitor is a compound selected from one or more of the compounds of Table 1-A, or a pharmaceutically acceptable salt or solvate thereof.

TABLE 1-A

| Cpd. No. | Structure | Name |
|---|---|---|
| 22 | 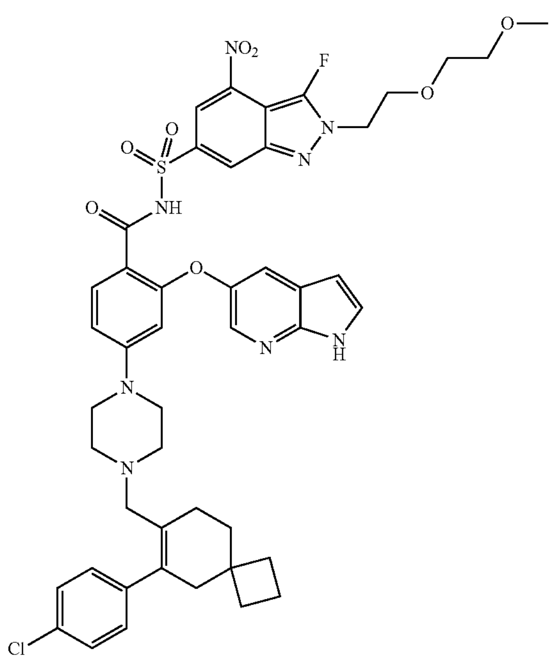 [SMILES: COCCOCCn1nc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2c1F] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-fluoro-2-(2-(2-methoxyethoxy)ethyl)-4-nitro-2H-indazol-6-yl)sulfonyl)benzamide |

TABLE 1-A-continued

| Cpd. No. | Structure | Name |
|---|---|---|
| 23 | 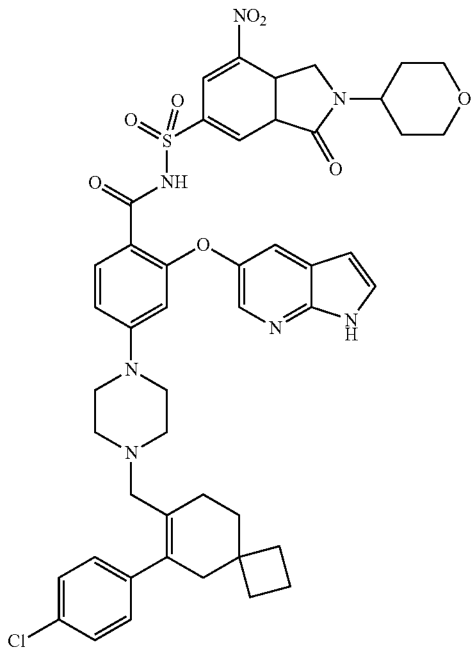 [SMILES: O=C(NS(=O)(=O)C1=CC2C(=O)N(C3CCOCC3)CC2C([N+](=O)[O-])=C1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-3-oxo-2-(tetrahydro-2H-pyran-4-yl)-2,3,3a,7a-tetrahydro-1H-isoindol-5-yl)sulfonyl)benzamide |
| 24 | 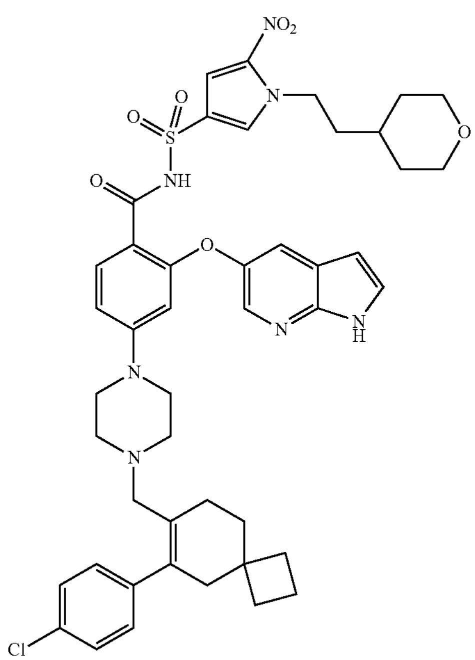 [SMILES: O=C(NS(=O)(=O)c1cc([N+](=O)[O-])n(CCC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((5-nitro-1-(2-(tetrahydro-2H-pyran-4-yl)ethyl)-1H-pyrrol-3-yl)sulfonyl)benzamide |

TABLE 1-A-continued
| Cpd. No. | Structure | Name |
|---|---|---|
| 25 | 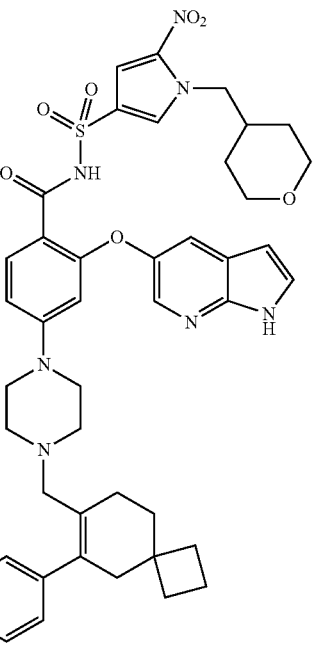 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((5-nitro-1-((tetrahydro-2H-pyran-4-yl)methyl)-1H-pyrrol-3-yl)sulfonyl)benzamide |
| 26 | 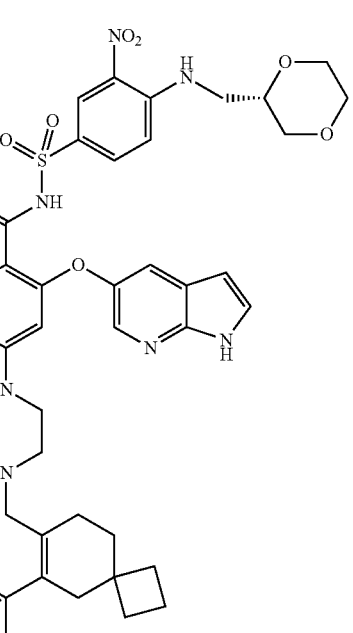 | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluorobenzamide |

TABLE 1-A-continued

| Cpd. No. | Structure | Name |
|---|---|---|
| 27 | 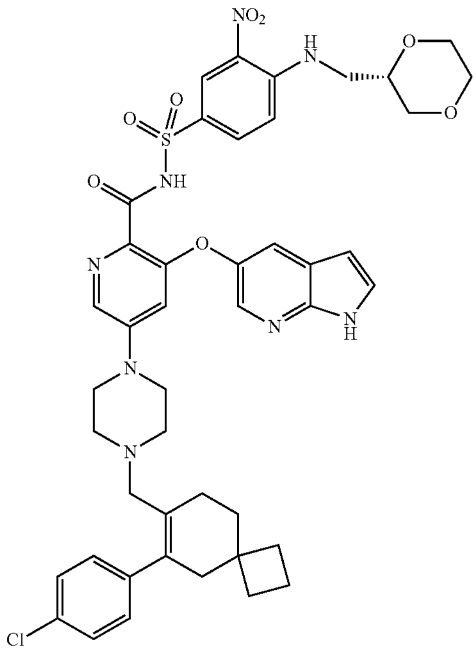 [SMILES: O=C(NS(=O)(=O)c1ccc(NC[C@H]2COCCO2)c([N+](=O)[O-])c1)c1ncc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-3-((1H-pyrrolo[2,3-b]pyridin-5-yl)oxy)-5-(4-((6-(4-chlorophenyl)spiro[3.5]non-6-en-7-yl)methyl)piperazin-1-yl)picolinamide |
| 28 | 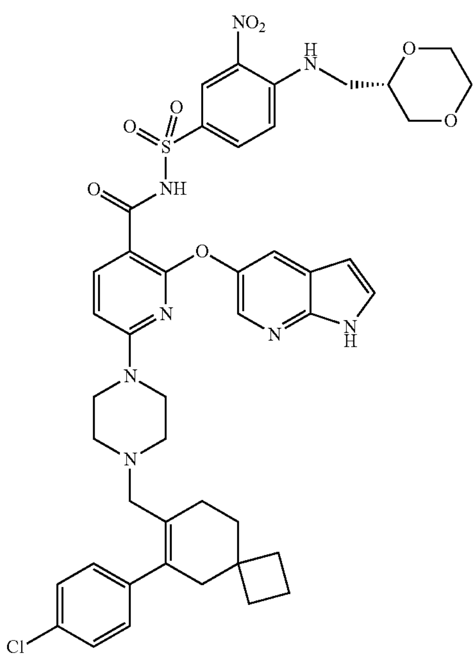 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)nc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-6-(4-((6-(4-chlorophenyl)spiro[3.5]non-6-en-7-yl)methyl)piperazin-1-yl)nicotinamide |

TABLE 1-A-continued

| Cpd. No. | Structure | Name |
|---|---|---|
| 29 | 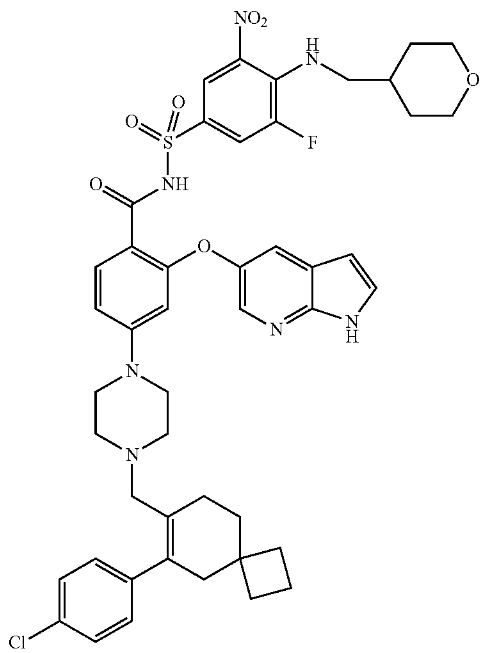 [SMILES: O=C(NS(=O)(=O)c1cc(F)c(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-fluoro-5-nitro-4-(((tetrahydro-2H-pyran-4-yl)methyl)amino)phenyl)sulfonyl)benzamide |
| 30 | 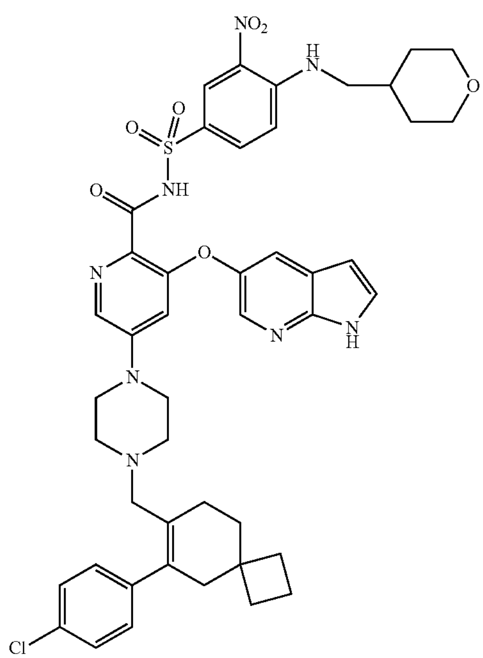 [SMILES: O=C(NS(=O)(=O)c1ccc(NCC2CCOCC2)c([N+](=O)[O-])c1)c1ncc(N2CCN(CC3=C(c4ccc(Cl)cc4)CC4(CCC4)CC3)CC2)cc1Oc1cnc2[nH]ccc2c1] | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)picolinamide |

TABLE 1-A-continued

| Cpd. No. | Structure | Name |
|---|---|---|
| 31 | 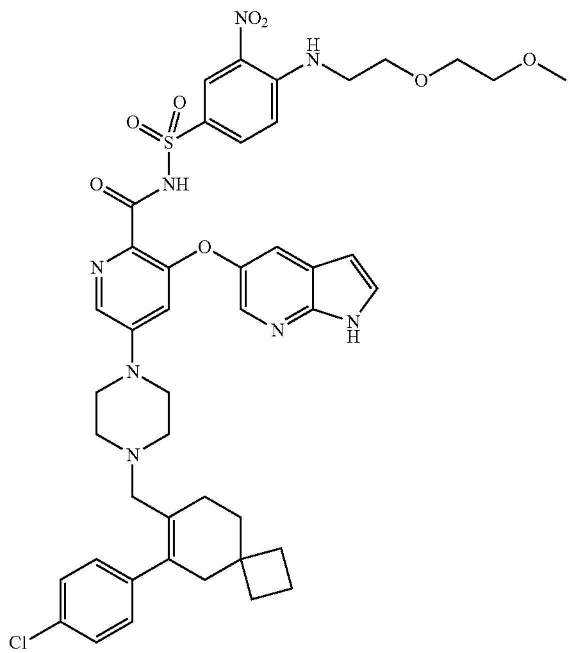 [SMILES: COCCOCCNc1ccc(S(=O)(=O)NC(=O)c2ncc(N3CCN(CC4=C(c5ccc(Cl)cc5)CC5(CCC5)CC4)CC3)cc2Oc2cnc3[nH]ccc3c2)cc1[N+](=O)[O-]] | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)picolinamide |
| 32 | 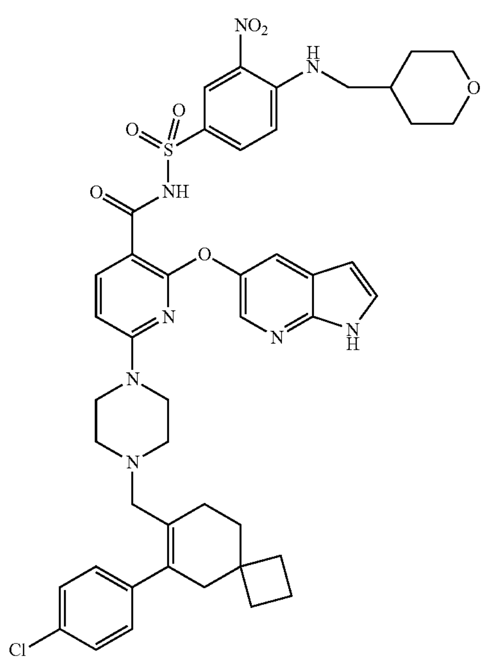 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)nc1Oc1cnc2[nH]ccc2c1] | 2-((1H-pyrrolo[2,3-b]pyridin-5-yl)oxy)-6-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)nicotinamide |

| Cpd. No. | Structure | Name |
|---|---|---|
| 33 | 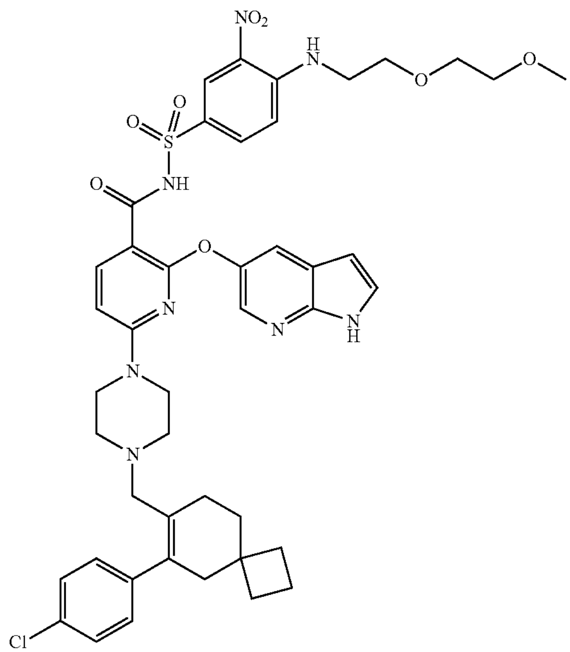 [SMILES: COCCOCCNc1ccc(S(=O)(=O)NC(=O)c2ccc(N3CCN(CC4=C(c5ccc(Cl)cc5)CC5(CCC5)CC4)CC3)nc2Oc2cnc3[nH]ccc3c2)cc1[N+](=O)[O-]] | 2-((1H-pyrrolo[2,3-b]pyridin-5-yl)oxy)-6-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)nicotinamide |
| 34 | 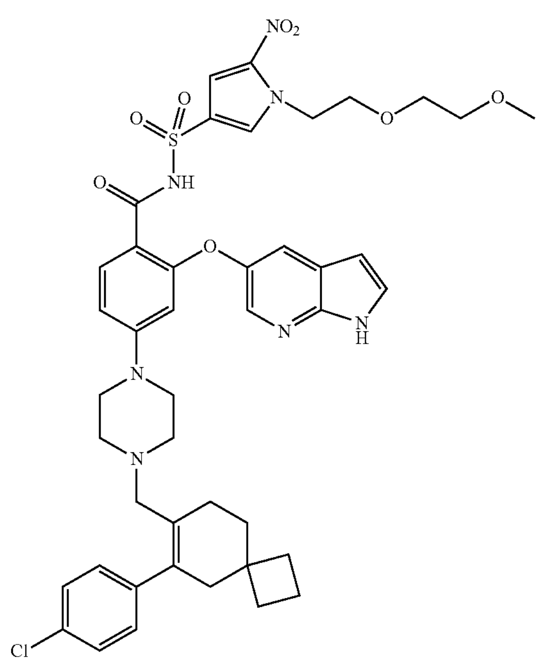 [SMILES: COCCOCCn1cc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((4-((2-(2-methoxyethoxy)ethyl)amino)-3-nitrophenylsulfonyl)picolinamide |

TABLE 1-A-continued
| Cpd. No. | Structure | Name |
|---|---|---|
| 35 | 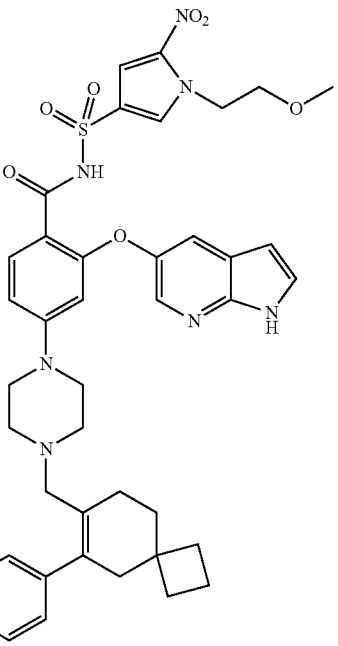 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-(2-methoxyethyl)-5-nitro-1H-pyrrol-3-yl)sulfonyl)benzamide |
| 36 | 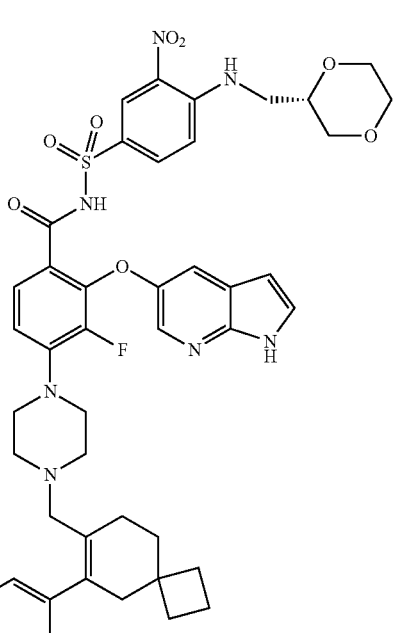 | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluorobenzamide |

TABLE 1-A-continued

| Cpd. No. | Structure | Name |
|---|---|---|
| 37 | 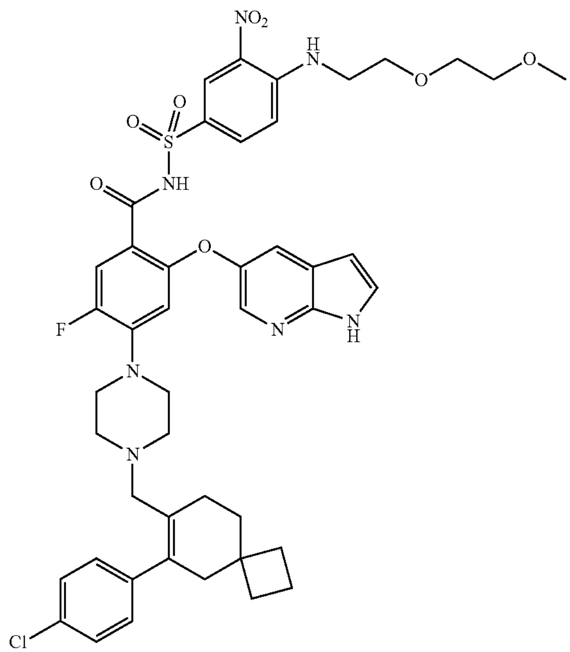 [SMILES: COCCOCCNc1ccc(S(=O)(=O)NC(=O)c2cc(F)c(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluoro-N-((4-((2-(2-methoxyethoxy)ethyl)amino)-3-nitrophenyl)sulfonyl)benzamide |
| 38 | 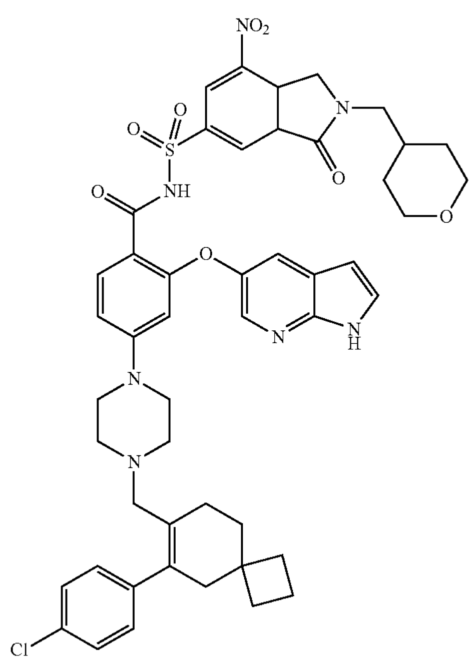 [SMILES: O=C(NS(=O)(=O)C1=CC2C(=O)N(CC3CCOCC3)CC2C([N+](=O)[O-])=C1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-3-oxo-2-((tetrahydro-2H-pyran-4-yl)methyl)-2,3,3a,7a-tetrahydro-1H-isoindol-5-yl)sulfonyl)benzamide |

TABLE 1-A-continued

| Cpd. No. | Structure | Name |
|---|---|---|
| 39 | 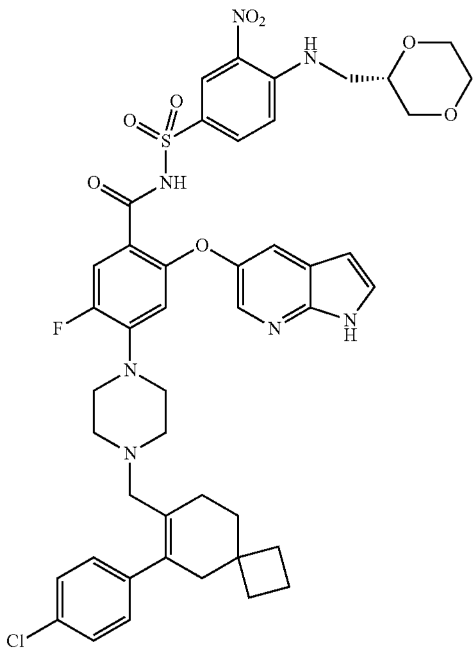 [SMILES: O=C(NS(=O)(=O)c1ccc(NC[C@H]2COCCO2)c([N+](=O)[O-])c1)c1cc(F)c(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluorobenzamide |
| 40 | 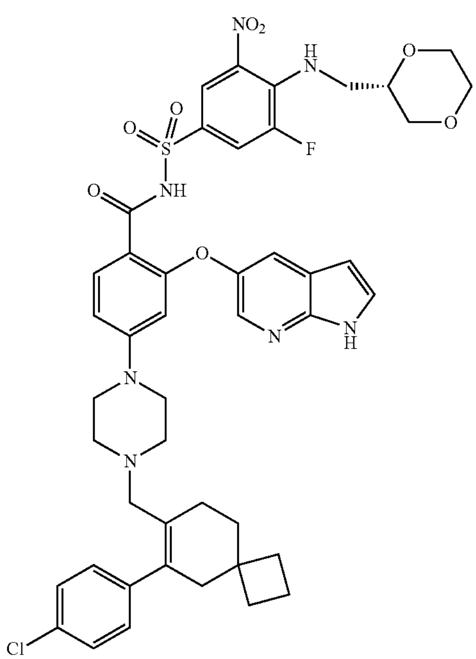 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-A-continued

| Cpd. No. | Structure | Name |
| --- | --- | --- |
| 41 | 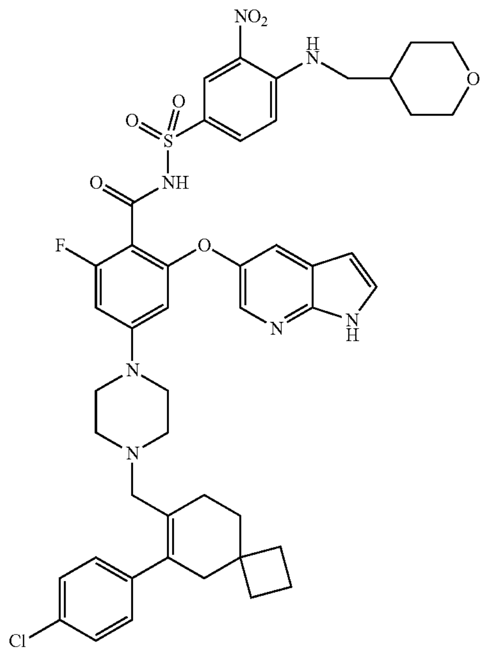 [SMILES: O=C(NS(=O)(=O)c1ccc(NCC2CCOCC2)c([N+](=O)[O-])c1)c1c(F)cc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-6-fluoro-N-((3-nitro-4-(((tetrahydro-2H-pyran-4-yl)methyl)amino)phenyl)sulfonyl)benzamide |
| 42 | 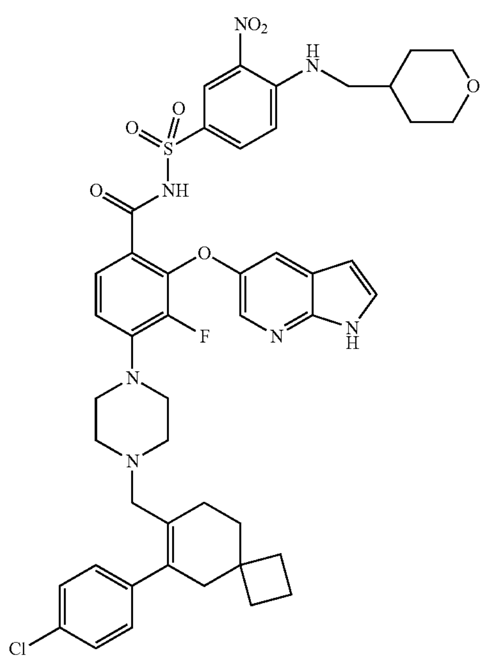 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)c(F)c1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluoro-N-((3-nitro-4-(((tetrahydro-2H-pyran-4-yl)methyl)amino)phenyl)sulfonyl)benzamide |

TABLE 1-A-continued

| Cpd. No. | Structure | Name |
| --- | --- | --- |
| 43 | 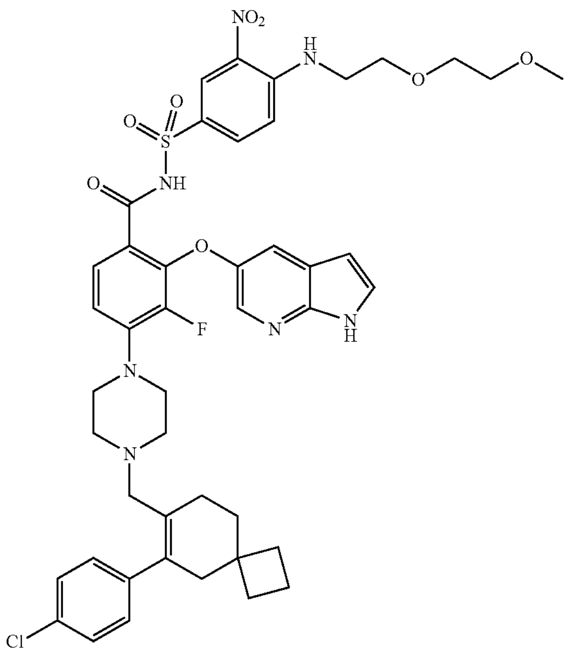 [SMILES: COCCOCCNc1ccc(S(=O)(=O)NC(=O)c2ccc(N3CCN(CC4=C(c5ccc(Cl)cc5)CC5(CCC5)CC4)CC3)c(F)c2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluoro-N-((4-((2-(2-methoxyethoxy)ethyl)amino)-3-nitrophenyl)sulfonyl)benzamide |
| 44 | 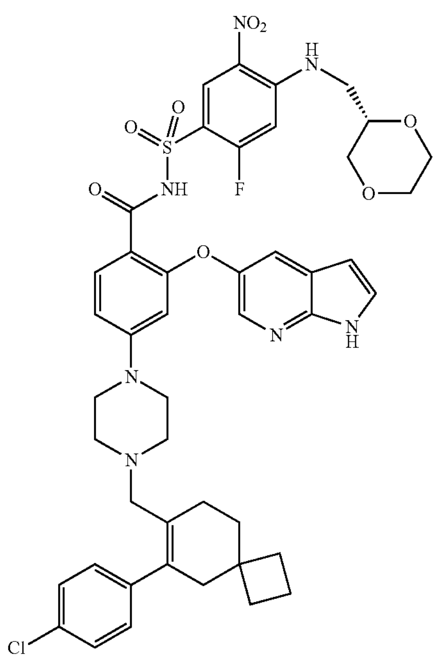 [SMILES: O=C(NS(=O)(=O)c1cc([N+](=O)[O-])c(NC[C@H]2COCCO2)cc1F)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-2-fluoro-5-nitrophenyl)sulfonyl)-2-((1H-pyrrolo[2,3-b]pyridin-5-yl)oxy)-4-(4-((6-(4-chlorophenyl)spiro[3,5]non-6-en-7-yl)methyl)piperazin-1-yl)benzamide |

TABLE 1-A-continued

| Cpd. No. | Structure | Name |
|---|---|---|
| 45 | 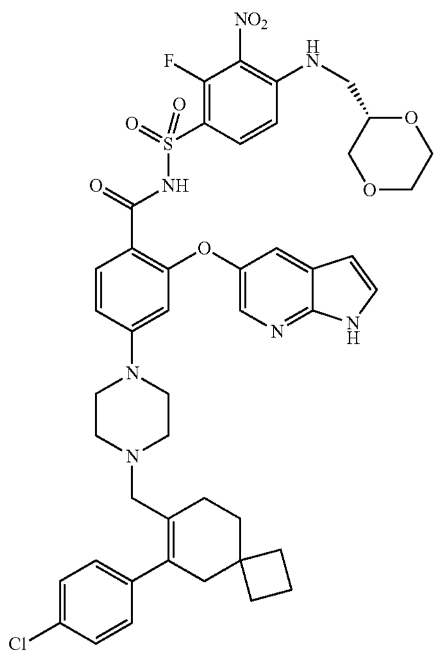 [SMILES: O=C(NS(=O)(=O)c1ccc(NC[C@H]2COCCO2)c([N+](=O)[O-])c1F)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-2-fluoro-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 46 | 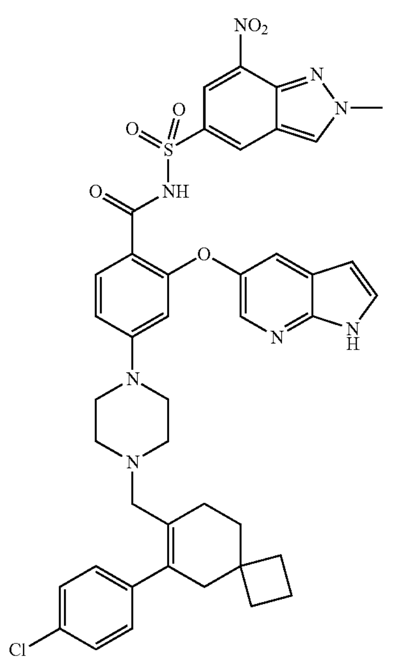 [SMILES: Cn1cc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2n1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-methyl-7-nitro-2H-indazol-5-yl)sulfonyl)benzamide |

TABLE 1-A-continued
| Cpd. No. | Structure | Name |
|---|---|---|
| 47 | 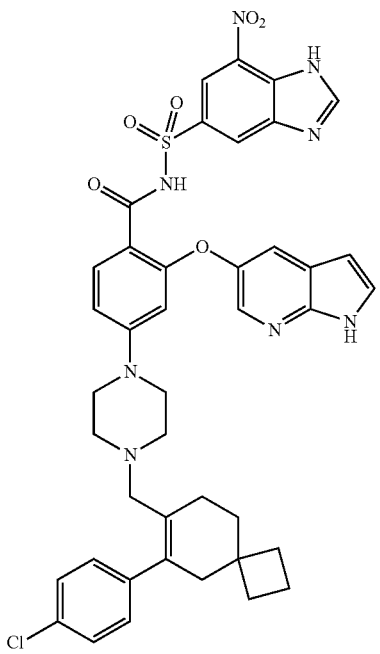 [SMILES: O=C(NS(=O)(=O)c1cc([N+](=O)[O-])c2[nH]cnc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-1H-benzo[d]imidazol-5-yl)sulfonyl)benzamide |
| 48 | 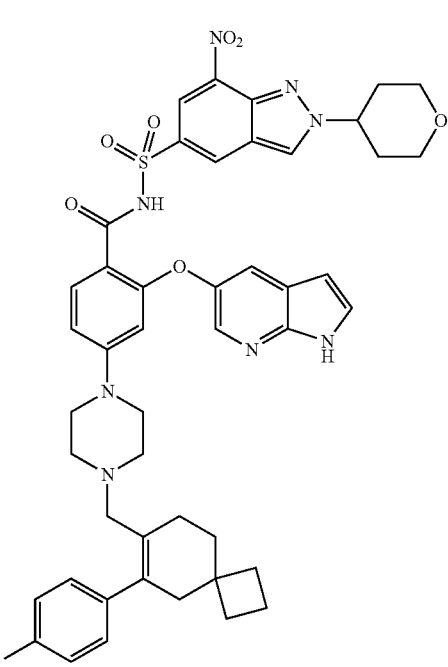 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-(tetrahydro-2H-pyran-4-yl)-2H-indazol-5-yl)sulfonyl)benzamide |

TABLE 1-A-continued

| Cpd. No. | Structure | Name |
|---|---|---|
| 49 | 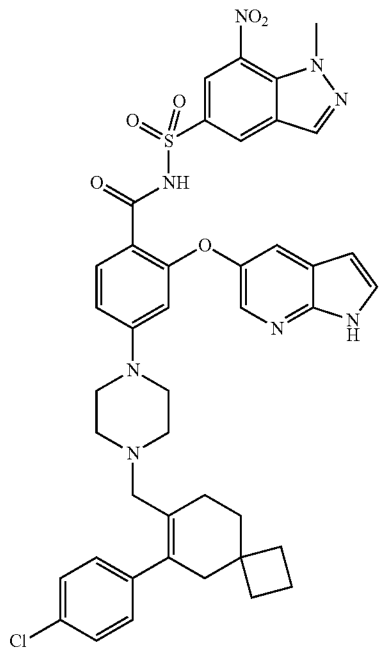 [SMILES: Cn1ncc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c21] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-7-nitro-1H-indazol-5-yl)sulfonyl)benzamide |
| 50 | 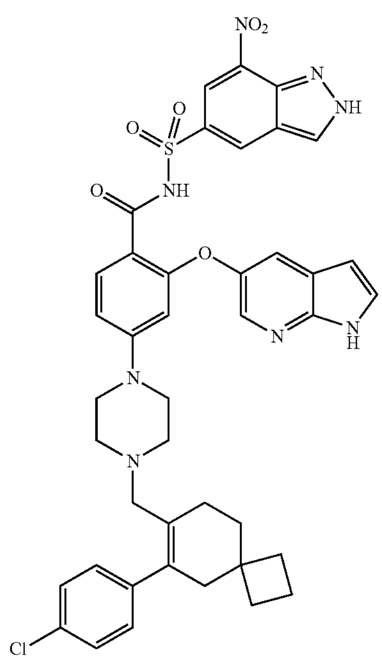 [SMILES: O=C(NS(=O)(=O)c1cc([N+](=O)[O-])c2n[nH]cc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2H-indazol-5-yl)sulfonyl)benzamide |

TABLE 1-A-continued
| Cpd. No. | Structure | Name |
|---|---|---|
| 51 | 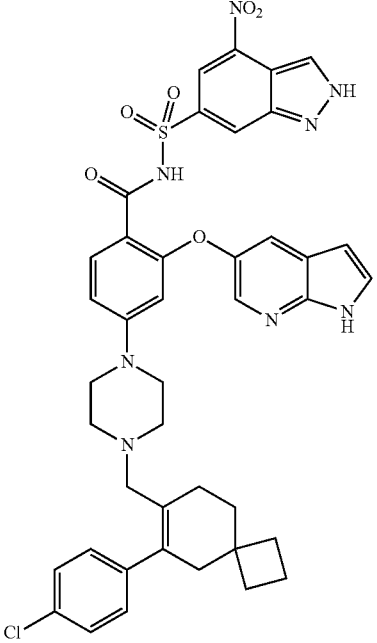 [SMILES: O=C(NS(=O)(=O)c1cc([N+](=O)[O-])c2c[nH]nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2H-indazol-6-yl)sulfonyl)benzamide |
| 52 | 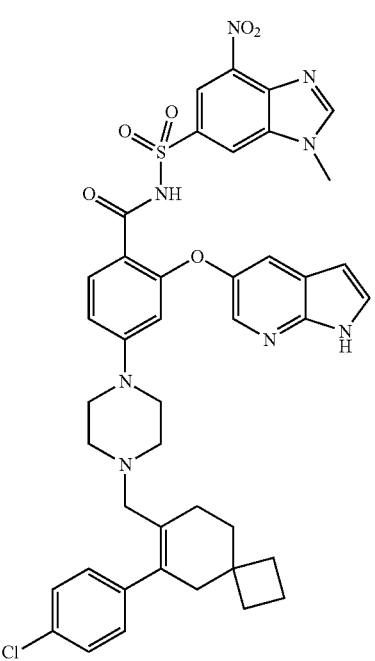 [SMILES: Cn1cnc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc21] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-4-nitro-1H-benzo[d]imidazol-6-yl)sulfonyl)benzamide |

TABLE 1-A-continued
| Cpd. No. | Structure | Name |
|---|---|---|
| 53 | 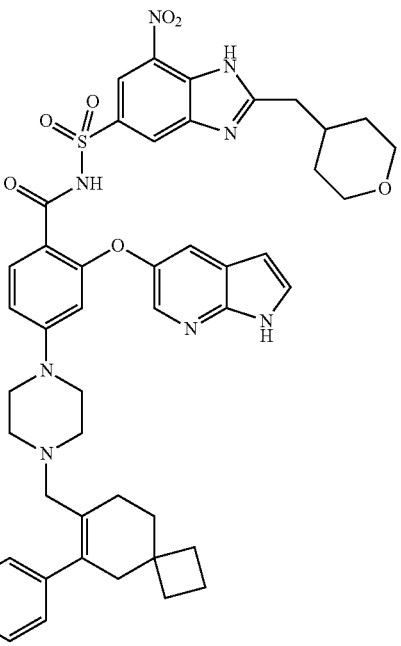 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-((tetrahydro-2H-pyran-4-yl)methyl)-1H-benzo[d]imidazol-5-yl)sulfonyl)benzamide |
| 54 | 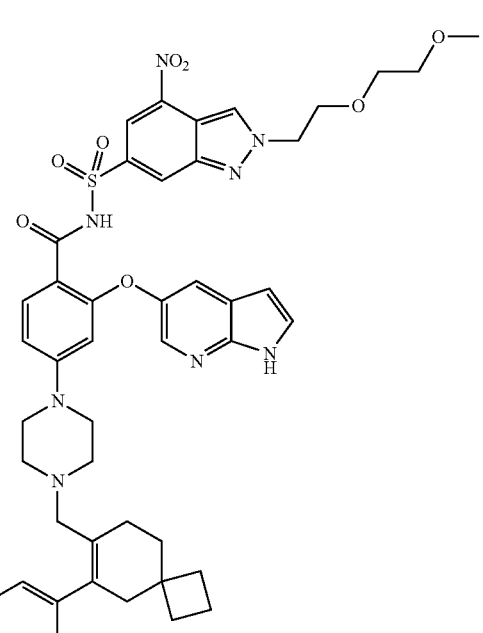 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-(2-methoxyethoxy)ethyl)-4-nitro-2H-indazol-6-yl)sulfonyl)benzamide |

TABLE 1-A-continued
| Cpd. No. | Structure | Name |
|---|---|---|
| 55 | 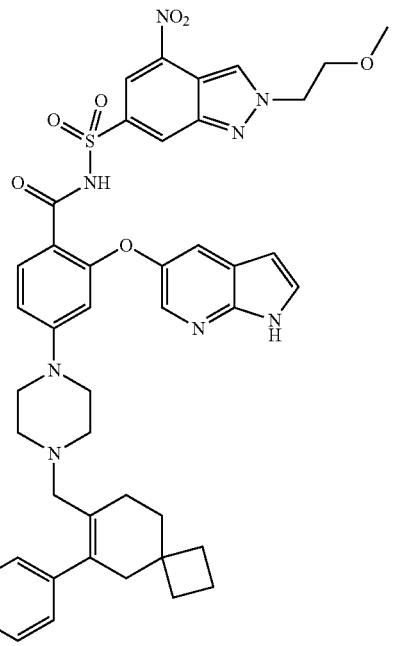 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-methoxyethyl)-4-nitro-2H-indazol-6-yl)sulfonyl)benzamide |
| 56 | 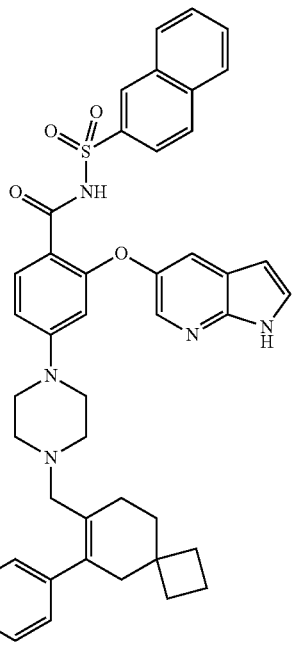 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-(naphthalen-2-ylsulfonyl)benzamide |

In some embodiments, the Bcl-2 inhibitor is the compound of Table 1-B, or a pharmaceutically acceptable salt or solvate thereof.

TABLE 1-B

| Cpd. No. | Structure | Name |
|---|---|---|
| 57 | 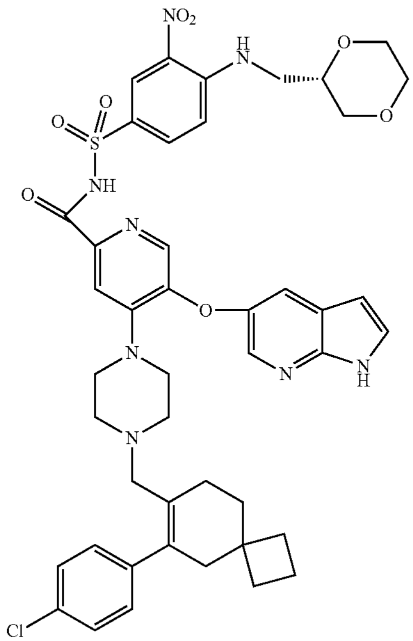 [SMILES: O=C(NS(=O)(=O)c1ccc(NC[C@H]2COCCO2)c([N+](=O)[O-])c1)c1cc(N2CCN(CC3=C(c4ccc(Cl)cc4)CC4(CCC4)CC3)CC2)c(Oc2cnc3[nH]ccc3c2)cn1] | (S)-N-((4-(((1,4-dioxan-2-yl)methyl)amino)-3-nitrophenyl)sulfonyl)-5-((1H-pyrrolo[2,3-b]pyridin-5-yl)oxy)-4-(4-((6-(4-chlorophenyl)spiro[3.5]non-6-en-7-yl)methyl)piperazin-1-yl)picolinamide |

In some embodiments, the MDM2 inhibitor is selected from the group consisting of APG-115, SAR405838, RG7112, RG7388 (Idasanutlin), MI-773, Nutlin 3, Nutlin 3a, Nutlin 3b, HDM201, Kevetrin hydrochloride, MX69, NVP-CGM097, NVP-CGM097 sulfate, Nutlin 3b, R08994, YH239-EE, NVP-CGM097 stereoisomer, AMG 232, Triptolide, NSC59984, PRIMA-1, NSC66811, NSC207895, Serdemetan (JNJ 26854165), R5C3, Caylin-1, Caylin-2, HL1373, NSC319726, YH239-EE or Tenovin-1. Preferably, the MDM2 inhibitor is APG-115.

In some embodiments, the MDM2 inhibitor is selected from the group

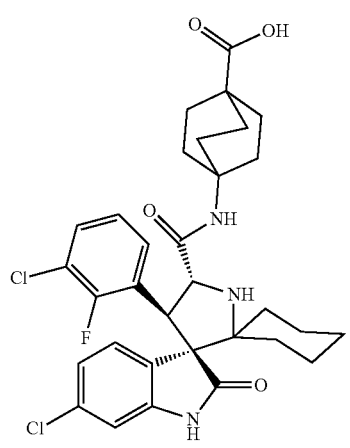

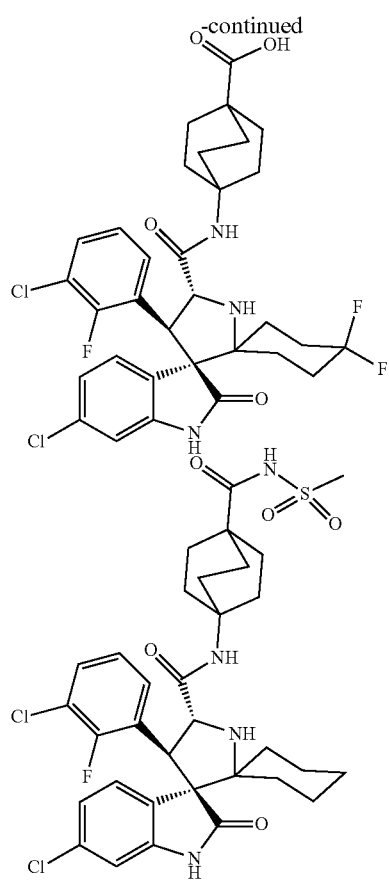

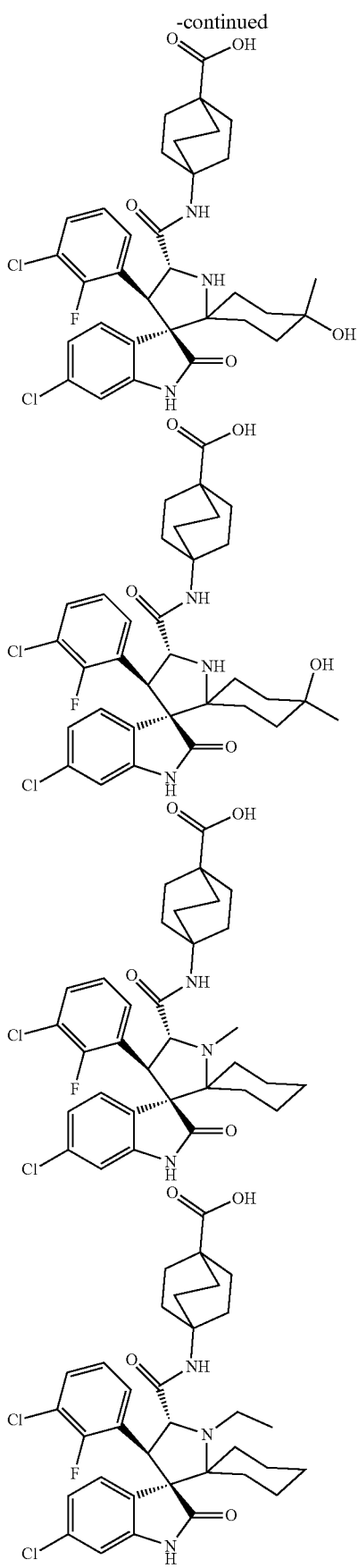

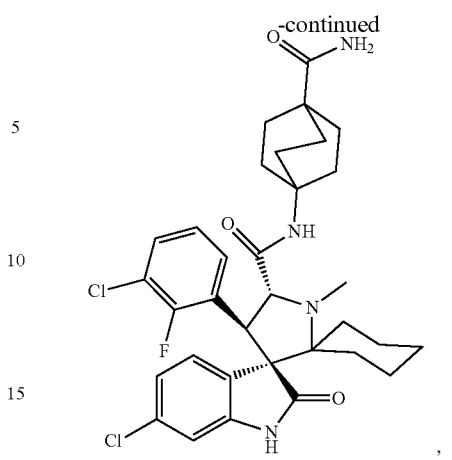

consisting of DS-3032b, BI-907828, ALRN-6924 or UBX0101.

In some embodiments, the Bcl-2 inhibitor is the following compound or a pharmaceutically acceptable salt or solvate thereof:

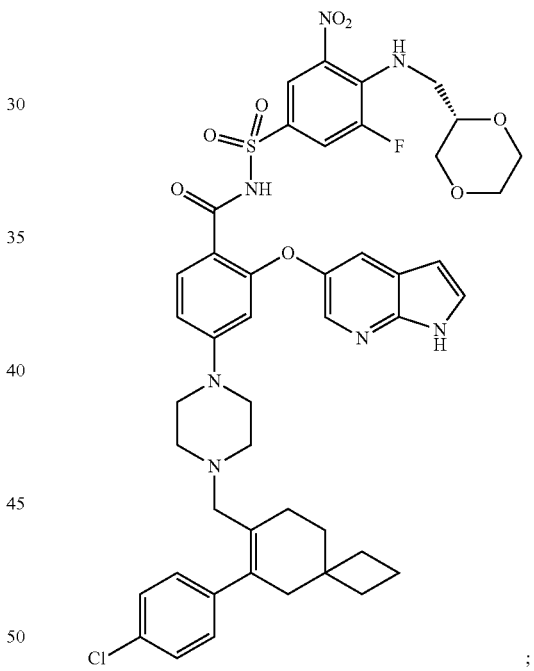

the MDM2 inhibitor is APG-115 or a pharmaceutically acceptable salt or solvate thereof.

In some embodiments, the combination product is in the form of a pharmaceutical composition.

In some embodiments, the Bcl-2 inhibitor and the MDM2 inhibitor are each in a separate preparation.

In some embodiments, the Bcl-2 inhibitor and the MDM2 inhibitor are administered simultaneously or sequentially.

In some embodiments, the Bcl-2 inhibitor and the MDM2 inhibitor may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the combination products of the invention containing the Bcl-2 inhibitor and the MDM2 inhibitor in the form of a pharmaceutical composition (preferably, each in a separate dosage unit form), as desired, may be administered for, including, but not limited to, 1 time, 2 times, 3 times, 4 times, 5 times or 6 times.

In some embodiments, the combination product of the present invention containing the Bcl-2 inhibitor and the MDM2 inhibitor, in the form of a pharmaceutical composition (preferably, in the form of a dosage unit), as desired, may be administered for, including, but not limited to, 1 time, 2 times, 3 times, 4 times, 5 times or 6 times.

In some embodiments, the combination product can be administered in the following manner: oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor, or a pharmaceutically acceptable salt or solvate thereof, is administered in an amount from about 0.0025 to 1500 mg/day. Preferably, the daily dose of the Bcl-2 inhibitor is 1 mg, 5 mg, 10 mg, 20 mg, 30 mg, 40 mg, 50 mg, 60 mg, 61 mg, 70 mg, 80 mg, 90 mg, 100 mg, 122 mg, 150 mg, 200 mg, 244 mg, 250 mg, 300 mg, 350 mg, 400 mg, 450 mg, 460 mg, 470 mg, 480 mg, 487 mg, 490 mg, 500 mg, 550 mg, 600 mg, 650 mg, 700 mg, 750 mg, 800 mg, 850 mg, 900 mg, 950 mg, 1000 mg, and a range between the respective doses, for example, 1 mg to 1000 mg, 30 mg to 900 mg, 61 mg to 800 mg, 100 mg to 700 mg, 122 mg to 600 mg, 122 mg to 500 mg, 122 mg to 487 mg, 122 mg to 300 mg, 122 mg to 244 mg, 30 mg to 487 mg, 61 mg to 487 mg and the like. And the MDM2 inhibitor or a pharmaceutically acceptable salt or solvate thereof is administered in an amount of from about 0.005 to 500 mg/day. Preferably, the daily dose of the MDM2 inhibitor is 10 mg, 20 mg, 30 mg, 40 mg, 50 mg, 60 mg, 70 mg, 80 mg, 90 mg, 100 mg, 150 mg, 200 mg, 244 mg, 250 mg, 300 mg, 350 mg, 400 mg, 450 mg, 460 mg, 470 mg, 480 mg, 487 mg, 490 mg, 500 mg, and a range between the respective doses, for example, 10 mg to 500 mg, 20 mg to 450 mg, 30 mg to 400 mg, 40 mg to 300 mg, 50 mg to 244 mg, 100 mg to 240 mg, 200 mg to 244 mg, 200 mg to 487 mg, 244 mg to 487 mg, and the like.

In some embodiments, the combination product further comprises a pharmaceutically acceptable carrier, diluent or excipient.

In some embodiments, the combination product is in the form of tablet, capsule, granule, syrup, powder, lozenge, sachet, cachet, elixir, suspension, emulsion, solution, syrup, aerosol, ointment, cream and injection.

A second aspect of the invention relates to the use of a Bcl-2 inhibitor and an MDM2 inhibitor in the manufacture of a medicament for the prevention and/or treatment of a disease, in which the disease is a cancer.

In some embodiments, the Bcl-2 inhibitor is a compound (e.g, Compound I-A), or a pharmaceutically acceptable salt or solvate thereof, as specifically described in the first aspect of the invention.

In some embodiments, the MDM2 inhibitor is selected from the group consisting of: APG-115, SAR405838, RG7112, RG7388 (Idasanutlin), MI-773, Nutlin 3, Nutlin 3a, Nutlin 3b, HDM201, Kevetrin hydrochloride, MX69, NVP-CGM097, NVP-CGM097 sulfate, Nutlin 3b, R08994, YH239-EE, NVP-CGM097 stereoisomer, AMG 232, Triptolide, NSC59984, PRIMA-1, NSC66811, NSC207895, Serdemetan (JNJ 26854165), R5C3, Caylin-1, Caylin-2, HL1373, NSC319726, YH239-EE or Tenovin-1. Preferably, the MDM2 inhibitor is APG-115.

In some embodiments, the MDM2 inhibitor is selected from the group

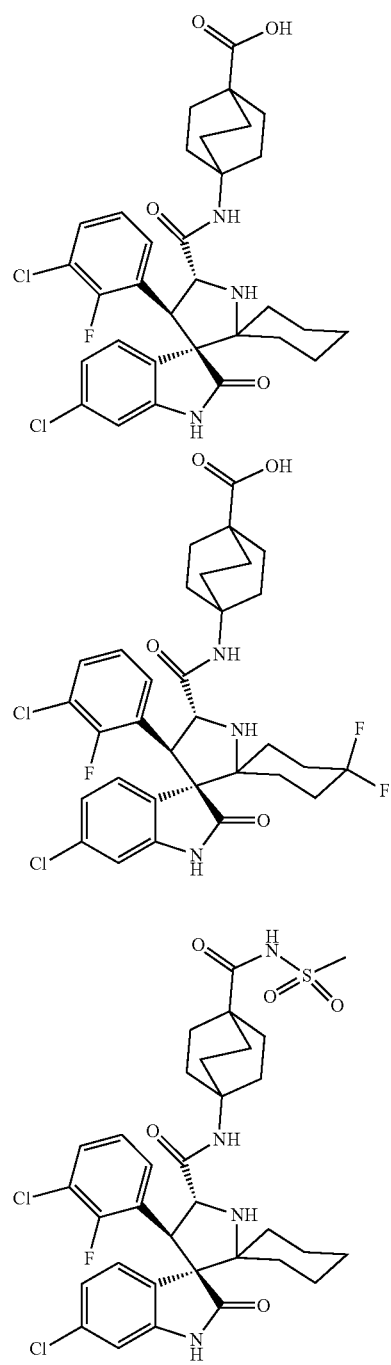

87

-continued

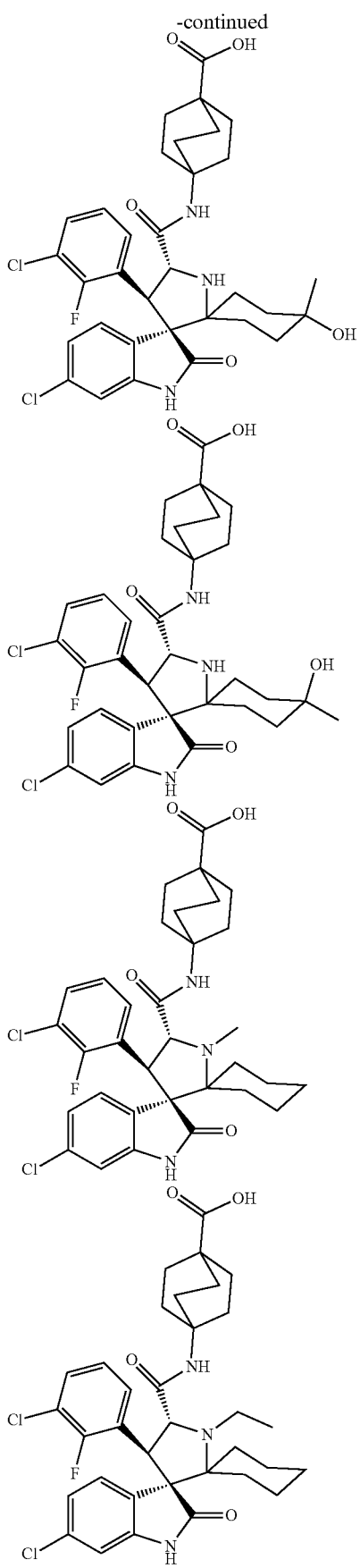

88

-continued

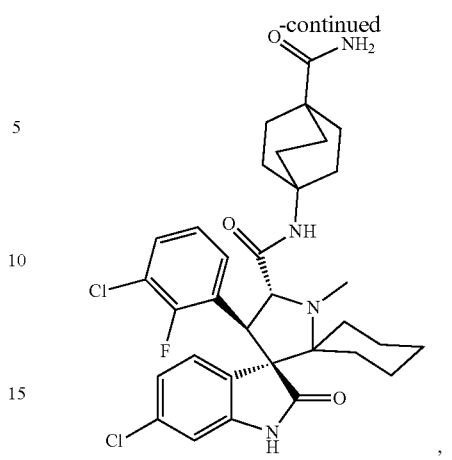

consisting of DS-3032b, BI-907828, ALRN-6924 or UBX0101.

In some embodiments, the Bcl-2 inhibitor is the following compound or a pharmaceutically acceptable salt or solvate thereof:

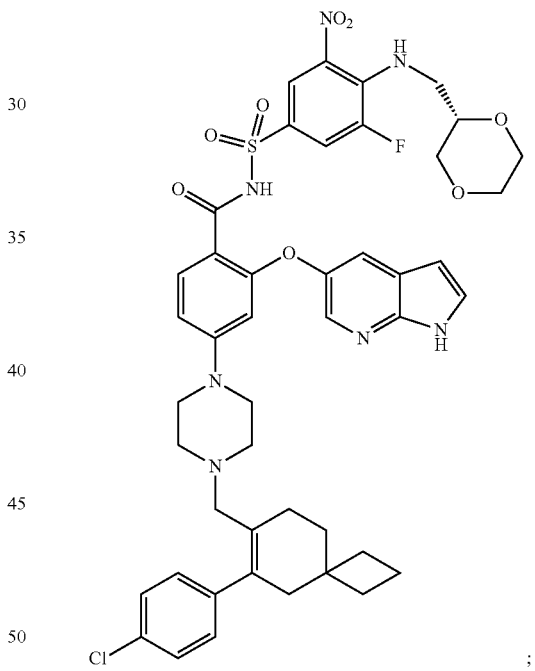

the MDM2 inhibitor is APG-115 or a pharmaceutically acceptable salt or solvate thereof.

In some embodiments, the medicament is in the form of a pharmaceutical composition.

In some embodiments, the Bcl-2 inhibitor and the MDM2 inhibitor are each in a separate preparation.

In some embodiments, the Bcl-2 inhibitor and the MDM2 inhibitor are administered simultaneously or sequentially.

In some embodiments, the Bcl-2 inhibitor and the MDM2 inhibitor may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the medicament of the present invention containing the Bcl-2 inhibitor and the MDM2 inhibitor in the form of a pharmaceutical composition (preferably, each in a separate dosage unit form), as desired, may be administered for, including, but not limited to, 1 time, 2 times, 3 times, 4 times, 5 times or 6 times.

In some embodiments, the medicament of the present invention containing the Bcl-2 inhibitor and the MDM2 inhibitor in the form of a pharmaceutical composition (preferably, in the form of a dosage unit), as desired, may be administered for, including, but not limited to, 1 time, 2 times, 3 times, 4 times, 5 times or 6 times.

In some embodiments, the medicament can be administered in the following manner: oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor or a pharmaceutically acceptable salt or solvate thereof, and the MDM2 inhibitor or a pharmaceutically acceptable salt or solvate thereof, are administered in a daily amount as described above in the first aspect of the invention in the detailed description of the invention.

In some embodiments, the disease is cancer.

Further, the cancer described in the present invention includes, but is not limited to, a cancer selected from the group consisting of: adrenal cancer, lymphoid epithelioma, acinic cell carcinoma, lymphoma, acoustic neuroma, acute lymphocytic leukemia, acral lentiginous melanoma, acute myelogeous leukemia, acrospiroma, chronic lymphocytic leukemia, acute eosinophilic leukemia, liver cancer, acute erythroid leukemia, small cell lung cancer, acute lymphoblastic leukemia, non-small cell lung cancer, acute megakaryoblastic leukemia, MALT lymphoma, acute monocytic leukemia, malignant fibrous histiocytoma, acute promyelocytic leukemia, malignant peripheral schwannomas, adenocarcinoma, malignant triton tumor, adenoid cystic carcinoma, mantle cell lymphoma, adenoma, marginal zone B cell lymphoma, adenomatoid odontogenic tumor, mast cell leukemia, adenosquamous carcinoma, mediastinal germ cell tumor, adipose tissue neoplasm, medullary carcinoma of the breast, adrenal cortical carcinoma, medullary thyroid carcinoma, adult T-cell leukemia/lymphoma, medulloblastoma, aggressive NK cell leukemia, melanoma, AIDS-related lymphoma, meningiomas, alveolar rhabdomyosarcoma, merkel cell carcinoma, alveolar soft tissue sarcoma, mesothelioma, ameloblastic fibroma, metastatic urothelial carcinoma, anaplastic large cell lymphoma, mixed mullerian tumor, anaplastic thyroid cancer, mucinous tumor, angioimmunoblastic T-cell lymphoma, multiple myeloma, angiomyolipoma, muscle tissue neoplasm, angiosarcoma, mycosis fungoides, astrocytoma, myxoid liposarcoma, atypical malformation rhabdoid tumor, myxoma, B cell chronic lymphocytic leukemia, myxosarcoma, B-cell prolymphocytic leukemia, nasopharyngeal carcinoma, B-cell lymphoma, neurinoma, basal cell carcinoma, neuroblastoma, biliary tract cancer, neurofibromatosis, bladder cancer, neuroma, blastoma, nodular melanoma, bone cancer, ocular cancer, Brenner tumor, oligodendroma, brown tumor, oligodendroglioma, Burkitt's lymphoma, oncocytoma, breast cancer, optic nerve sheath meningioma, brain cancer, optic nerve tumor, carcinoma, oral carcinoma, carcinoma in situ, osteosarcoma, carcinosarcoma, ovarian cancer, cartilage tumor, pancoast tumor, cementoma, papillary thyroid carcinoma, myeloid sarcoma, paraganglioma, chondroma, pineoblastoma, chordoma, pinealocytoma, choriocarcinoma, pituitary tumor, choroid plexus papilloma, pituitary adenoma, clear-cell sarcoma of the kidney, pituitary tumor, craniopharyngioma, plasmacytoma, cutaneous T-cell lymphoma, polyembryoma, cervical cancer, precursor T lymphoblastic lymphoma, colorectal cancer, primary central nervous system lymphoma, Degos' disease, primary effusion lymphoma, desmoplastic small round cell tumor, primary peritoneal cancer, diffuse large B-cell lymphoma, prostate cancer, dysembryoplastic neuroepithelial tumor, pancreatic cancer, dysgerminoma, pharyngeal carcinoma, embryonal carcinoma, peritoneal pseudomyxoma, endocrine gland tumor, renal cell carcinoma, endodermal sinus tumor, renal medullary carcinoma, enteropathy-associated T-cell lymphoma, retinoblastoma, esophageal cancer, rhabdomyomas, fetus-in-fetus, rhabdomyosarcoma, fibroma, Richter's transformation, fibrosarcoma, rectal cancer, follicular lymphoma, sarcoma, follicular thyroid cancer, schwannomatosis, ganglioneuroma, seminoma, gastrointestinal cancer, sertoli cell tumor, germ cell tumor, sex cord-gonadal stromal tumor, pregnancy-induced choriocarcinoma, signet ring cell carcinoma, giant cell fibroblastoma, skin cancer, giant cell tumor of bone, small blue round cell tumor, glial tumor, small cell carcinoma, glioblastoma multiforme, soft tissue sarcoma, glioma, somatostatinoma, gliomatosis cerebri, soot wart, glucagonoma, spinal tumor, gonadoblastoma, splenic marginal zone lymphoma, granulosa cell tumor, squamous cell carcinoma, gynandroblastoma, synovial sarcoma, gallbladder carcinoma, Sezary disease, gastric cancer, small intestine cancer, hairy cell leukemia, squamous cell carcinoma, hemangioblastoma, stomach cancer, head and neck cancer, T-cell lymphoma, hemangiopericytoma, testicular cancer, hematological malignancy, hepatoblastoma, thyroid cancer, hepatosplenic T-cell lymphoma, transitional cell carcinoma, Hodgkin's lymphoma, laryngeal cancer, non-Hodgkin's lymphoma, urachal carcinoma, invasive lobular carcinoma, genitourinary cancer, intestinal cancer, urothelial carcinoma, renal cancer, uveal melanoma, laryngeal cancer, uterine cancer, lentigo malign, verrucous carcinoma, lethal midline carcinoma, visual pathway glioma, leukemia, vulvar cancer, testicular stromal tumor, vaginal cancer, liposarcoma, Waldenstrom's macroglobulinemia, lung cancer, adenolymphoma, lymphangioma, nephroblastoma and lymphatic sarcoma.

Preferably, the cancer is selected from the group consisting of: acute monocytic leukemia, acute myeloid leukemia, chronic myelogenous leukemia, chronic lymphocytic leukemia and mixed lineage leukemia, NUT midline cancer, multiple myeloma, small cell lung cancer, neuroblastoma, Burkitt's lymphoma, cervical cancer, esophageal cancer, ovarian cancer, colorectal cancer, prostate cancer and breast cancer.

Preferably, the cancer is a hematological malignancy. The hematological malignancy is selected from the group consisting of non-Hodgkin's lymphoma (NHL), diffuse large B-cell lymphoma (DLBCL), follicular lymphoma (FL), acute myeloid leukemia (AML), acute lymphoblastic leukemia (ALL), chronic lymphocytic leukemia (CLL), multiple myeloma (MM).

More preferably, the cancer is selected from the group consisting of: non-Hodgkin's lymphoma (NHL), diffuse large B-cell lymphoma (DLBCL), follicular lymphoma (FL), acute myeloid leukemia (AML), acute lymphocytic leukemia (ALL), chronic lymphocytic leukemia (CLL), multiple myeloma (MM), non-small cell lung cancer (NSCLC).

Most preferably, the cancer is selected from the group consisting of acute myeloid leukemia (AML) and acute lymphocytic leukemia (ALL).

Preferably, the cancer is adrenocortical carcinoma, advanced cancer, anal cancer, aplastic anemia, cholangiocarcinoma, bladder cancer, bone cancer, bone metastasis, adult brain/CNS tumor, childhood brain/CNS tumor, breast cancer, male breast cancer, childhood cancer, unknown primary cancer, Castleman disease, cervical cancer, colon/rectal cancer, endometrial cancer, esophageal cancer, Ewing family of tumors, eye cancer, gallbladder cancer, gastrointestinal carcinoid tumor, gastrointestinal stromal tumor (GIST), gestational trophoblastic disease, Hodgkin disease, Kaposi sarcoma, kidney cancer, larynx and hypopharyngeal carcinoma, adult acute lymphoblastic leukemia (ALL), acute myeloid leukemia (AML), chronic lymphocytic leukemia (CLL), chronic myelogenous leukemia (CML), chronic myelogenous leukemia (CML), childhood leukemia, liver cancer, non-small cell lung cancer, small cell lung cancer, lung cancer, cutaneous lymphoma, malignant mesothelioma, multiple myeloma, myelodysplastic syndrome, nasal and paranasal sinus cancer, nasopharyngeal carcinoma, neuroblastoma, non-Hodgkin's lymphoma, non-Hodgkin's lymphoma in children, oral and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma—adult soft tissue cancer, basal skin cancer and squamous cell skin cancer, skin cancer—melanoma, small intestine cancer, stomach cancer, testicular cancer, thymic cancer, thyroid cancer, uterine sarcoma, vaginal cancer, vulvar cancer, Waldenstrom macroglobulinemia, or Wilms Tumor.

A third aspect of the invention relates to a combination product for preventing and/or treating a disease, in which the combination product comprises a Bcl-2 inhibitor and an MDM2 inhibitor, the disease is cancer. Further, the cancer includes, but is not limited to, those cancers as described in the second aspect of the invention in the above detailed description of the invention.

In some embodiments, the Bcl-2 inhibitor is a compound (e.g, Compound I-A), or a pharmaceutically acceptable salt or solvate thereof, as specifically described in the first aspect of the invention.

In some embodiments, the MDM2 inhibitor is selected from the group consisting of: APG-115, SAR405838, RG7112, RG7388 (Idasanutlin), MI-773, Nutlin 3, Nutlin 3a, Nutlin 3b, HDM201, Kevetrin hydrochloride, MX69, NVP-CGM097, NVP-CGM097 sulfate, Nutlin 3b, R08994, YH239-EE, NVP-CGM097 stereoisomer, AMG 232, Triptolide, NSC59984, PRIMA-1, NSC66811, NSC207895, Serdemetan (JNJ 26854165), R5C3, Caylin-1, Caylin-2, HL1373, NSC319726, YH239-EE or Tenovin-1. Preferably, the MDM2 inhibitor is APG-115.

In some embodiments, the MDM2 inhibitor is selected from the group

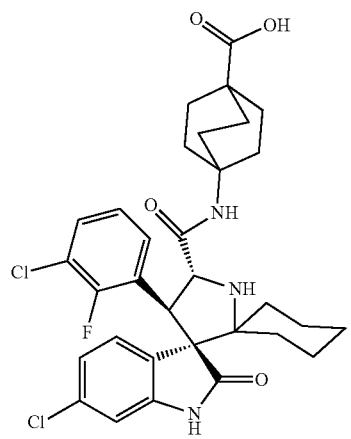

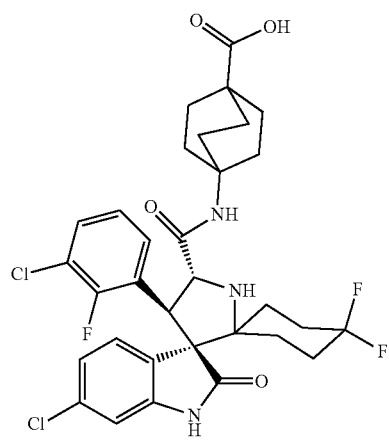

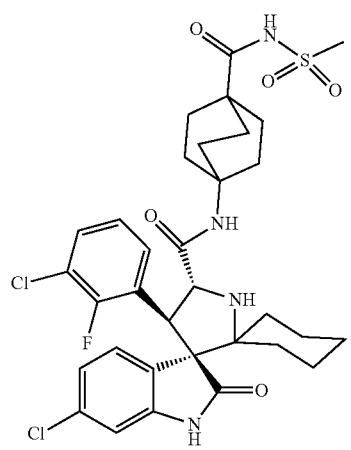

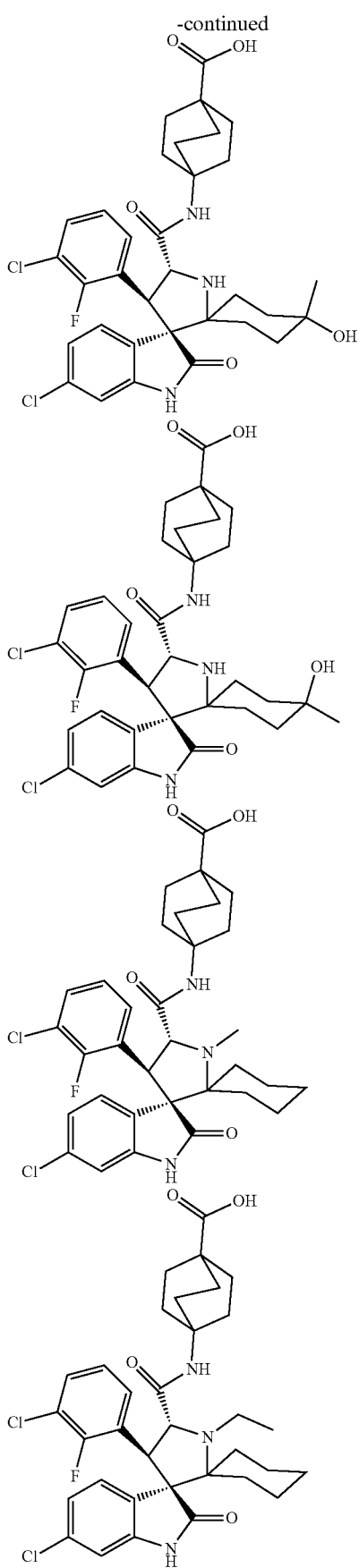

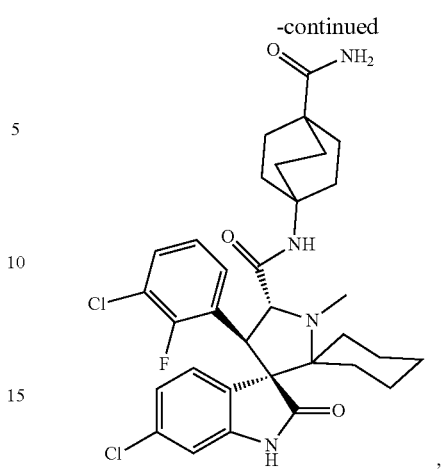

consisting of DS-3032b, BI-907828, ALRN-6924 or UBX0101.

In some embodiments, the Bcl-2 inhibitor is the following compound or a pharmaceutically acceptable salt or solvate thereof:

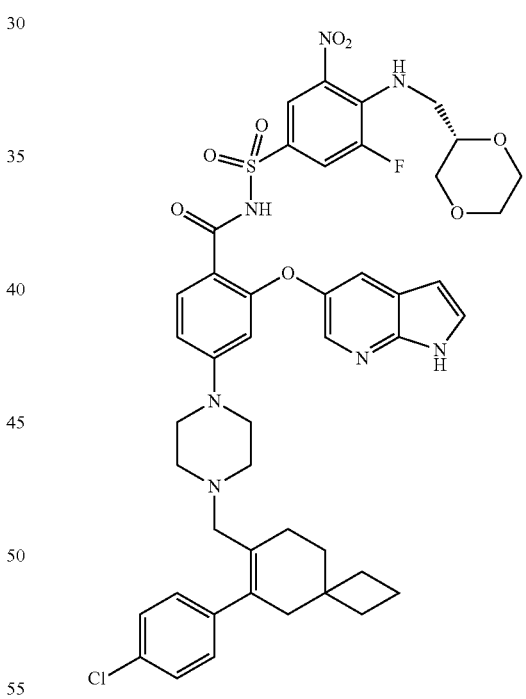

the MDM2 inhibitor is APG-115 or a pharmaceutically acceptable salt or solvate thereof.

In some embodiments, the combination product is in the form of a pharmaceutical composition.

In some embodiments, the Bcl-2 inhibitor and the MDM2 inhibitor are each in a separate preparation.

In some embodiments, the Bcl-2 inhibitor and the MDM2 inhibitor are administered simultaneously or sequentially.

In some embodiments, the Bcl-2 inhibitor and the MDM2 inhibitor may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the combination products of the invention containing the Bcl-2 inhibitor and the MDM2 inhibitor in the form of a pharmaceutical composition (preferably, each in a separate dosage unit form), as desired, may be administered for, including, but not limited to, 1 time, 2 times, 3 times, 4 times, 5 times or 6 times.

In some embodiments, the combination product of the present invention containing the Bcl-2 inhibitor and the MDM2 inhibitor, in the form of a pharmaceutical composition (preferably, in the form of a dosage unit), as desired, may be administered for, including, but not limited to, 1 time, 2 times, 3 times, 4 times, 5 times or 6 times.

In some embodiments, the combination product can be administered in the following manner: oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor or a pharmaceutically acceptable salt or solvate thereof, and the MDM2 inhibitor or a pharmaceutically acceptable salt or solvate thereof, are administered in a daily dose as described in the first aspect of the invention in the above detailed description of the invention.

A fourth aspect of the invention relates to a method of preventing and/or treating a disease comprising administering to a subject in need thereof a prophylactically and/or therapeutically effective amount of a Bcl-2 inhibitor and an MDM2 inhibitor, in which the disease is a cancer. Further, the cancer includes, but is not limited to, those cancers as described in the second aspect of the invention in the above detailed description of the invention.

In some embodiments, the Bcl-2 inhibitor is a compound (e.g, Compound I-A) or a pharmaceutically acceptable salt or solvate thereof, or as specifically described in the first aspect of the invention.

In some embodiments, the MDM2 inhibitor is selected from the group consisting of: APG-115, SAR405838, RG7112, RG7388 (Idasanutlin), MI-773, Nutlin 3, Nutlin 3a, Nutlin 3b, HDM201, Kevetrin hydrochloride, MX69, NVP-CGM097, NVP-CGM097 sulfate, Nutlin 3b, R08994, YH239-EE, NVP-CGM097 stereoisomer, AMG 232, Triptolide, NSC59984, PRIMA-1, NSC66811, NSC207895, Serdemetan (JNJ 26854165), R5C3, Caylin-1, Caylin-2, HL1373, NSC319726, YH239-EE or Tenovin-1. Preferably, the MDM2 inhibitor is APG-115.

In some embodiments, the MDM2 inhibitor is selected from the

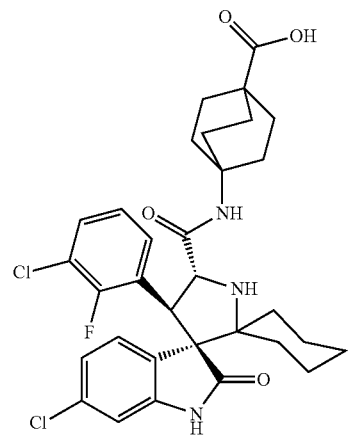

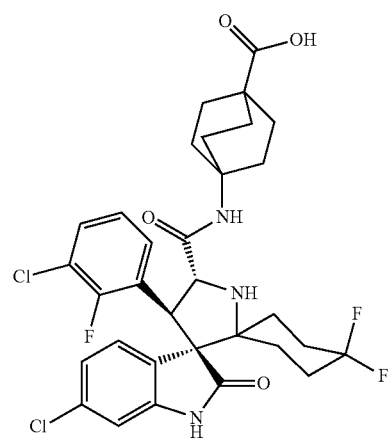

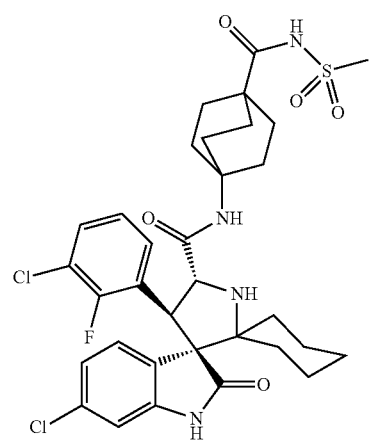

-continued

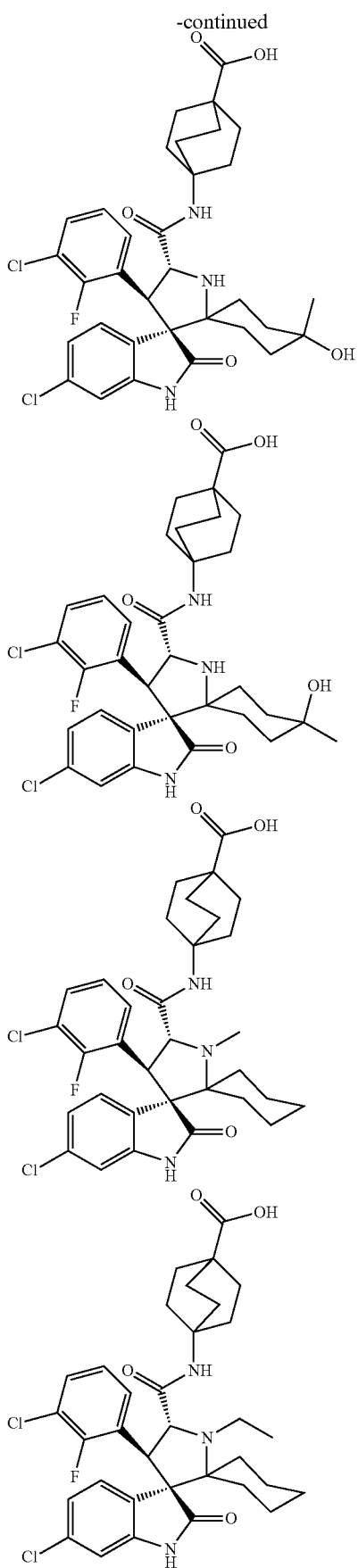

-continued

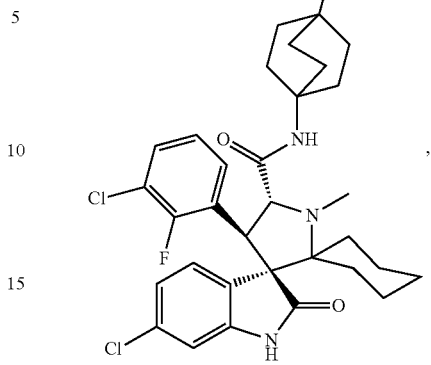

group consisting of DS-3032b, BI-907828, ALRN-6924 or UBX0101.

In some embodiments, the Bcl-2 inhibitor is the following compound or a pharmaceutically acceptable salt or solvate thereof:

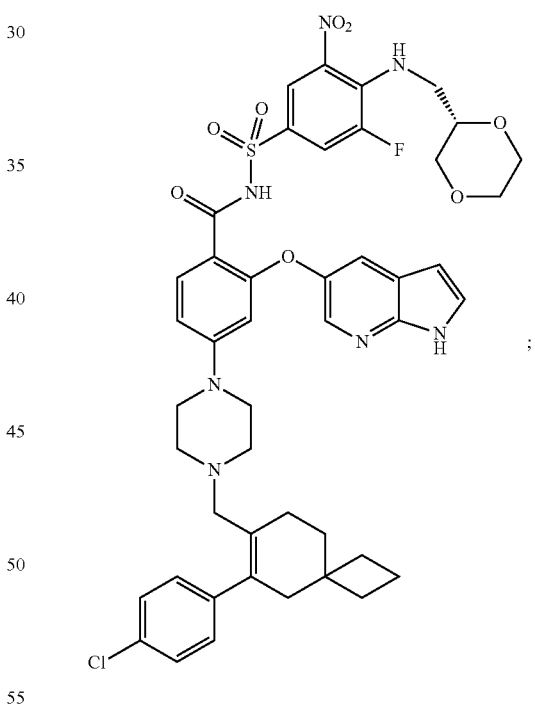

the MDM2 inhibitor is APG-115 or a pharmaceutically acceptable salt or solvate thereof.

In some embodiments, the Bcl-2 inhibitor and the MDM2 inhibitor are in the form of a pharmaceutical composition.

In some embodiments, the Bcl-2 inhibitor and the MDM2 inhibitor are each in a separate preparation.

In some embodiments, the Bcl-2 inhibitor and the MDM2 inhibitor are administered simultaneously or sequentially.

In some embodiments, the Bcl-2 inhibitor and the MDM2 inhibitor may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the Bcl-2 inhibitor and the MDM2 inhibitor in the form of a pharmaceutical composition (preferably, each in a separate dosage unit form), as desired, may be administered for, including, but not limited to, 1 time, 2 times, 3 times, 4 times, 5 times or 6 times.

In some embodiments, the Bcl-2 inhibitor and the MDM2 inhibitor in the form of a pharmaceutical composition (preferably, in the form of a dosage unit), as desired, may be administered for, including, but not limited to, 1 time, 2 times, 3 times, 4 times, 5 times or 6 times.

In some embodiments, the Bcl-2 inhibitor and the MDM2 inhibitor can be administered in the following manner: oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor is administered daily at a dose of 0.017 mg/kg, 0.083 mg/kg, 0.17 mg/kg, 0.33 mg/kg, 0.5 mg/kg, 0.67 mg/kg, 0.83 mg/kg, 1 mg/kg, 1.02 mg/kg, 1.16 mg/kg, 1.33 mg/kg, 1.5 mg/kg, 1.67 mg/kg, 2.03 mg/kg, 2.5 mg/kg, 3.33 mg/kg, 4.06 mg/kg, 4.17 mg/kg, 5 mg/kg, 5.83 mg/kg, 6.67 mg/kg, 7.5 mg/kg, 7.67 mg/kg, 7.83 mg/kg, 8 mg/kg, 8.12 mg/kg, 8.16 mg/kg, 8.33 mg/kg, 9.17 mg/kg, 10 mg/kg, 10.83 mg/kg, 11.66 mg/kg, 12.5 mg/kg, 13.33 mg/kg, 14.17 mg/kg, 15 mg/kg, 15.83 mg/kg, 16.67 mg/kg, and a range between the respective doses, for example, 0.017 mg to 16.67 mg/kg, 0.33 mg to 16.67 mg/kg, 1.02 mg to 15 mg/kg, 1.02 mg to 15 mg/kg, 1.02 to 12.5 mg, 1.02 mg to 10 mg/kg, 1.02 mg to 8.12 mg/kg, 1.02 mg to 4.06 mg/kg, 1.02 mg to 2.03 mg/kg, 2.03 mg to 4.06 mg/kg, etc., and the daily dose of the MDM2 inhibitor is 0.5 mg/kg, 0.67 mg/kg, 0.83 mg/kg, 1 mg/kg, 1.17 mg/kg, 1.22 mg/kg, 2.03 mg/kg, 2.5 mg/kg, 3.33 mg/kg, 4.06 mg/kg, 4.17 mg/kg, 5 mg/kg, 5.83 mg/kg, 6.67 mg/kg, 7.5 mg/kg, 7.67 mg/kg, 7.83 mg/kg, 8 mg/kg, 8.12 mg/kg, 8.16 mg/kg, 8.33 mg/kg, 9.17 mg/kg, 10 mg/kg, and a range between the respective doses, for example, 0.5 mg to 10 mg/kg, 1 mg to 10 mg/kg, 1 mg to 5 mg/kg, 2.5 mg to 8.12 mg/kg, 4.06 mg to 10 mg/kg, 4.06 mg to 8.12 mg/kg, and the like.

Lastly, WO 2018/027097 is incorporated by reference herein, in its entirety and for all purposes.

Specific Models for Carrying Out the Invention

The present invention will be further illustrated by the following examples and control examples. However, it should be understood that these examples and control examples are merely used to explain the invention in more details, but not intend to limit the present invention.

Example 1. General Experimental Methods Used in the Invention (1) CellTiter-Glo® (CTG) Cell Proliferation Assay Anti-proliferative effects were tested by CellTiter-Glo® (CTG) assay. Cells were seeded in 96-well plates and treated with different concentrations of test substance for 24 hours. By using 9 different concentrations of Compound 6 (which were selected in a 3× gradient between 10-3 and 101 μM, i.e., 0.0016, 0.0045, 0.014, 0.041, 0.12, 0.36, 1.1, 3.2, 10 μM) in combination with 3 different concentrations of MDM2 inhibitor (e.g., APG-115) in action for 24 hours, the effects of Compound 6 in combination with the drug were tested. Each test dose was tested with 3 replicate wells.

Usually, 9 series of doses of the test substance were selected, and added to 96-well plates, 5 μl/well. For the combination experiment, the final volume of the two test substances was 5 μl/well. Each test dose was tested with 3 replicate wells. On the same plate, 3-6 wells were selected and added with 100 μl of dilution solution as a control group, and another 3-6 wells were used as a blank control. In addition to the blank control wells, 95 μl of the cell suspension was added to each well (containing an appropriate number of cells to ensure that at the time of detection, the cells of the cell control group just covered the bottom of the well) of the same 96-well plate. The culture plate was cultured at 37° C. for 24 hours in a CO2 incubator. At the end of the culture, 96-well plates and CellTiter-Glo reagent were equilibrated at room temperature for 30 minutes, and 100 μL of CellTiter-Glo reagent was added to each well. After mixing on a shaker for 2 minutes, leaving at room temperature for 10 minutes, the fluorescence value was read by using a Biotek synergy HIMF plate reader. Using the average fluorescence value of 3 replicate wells, the percentage of cell viability was calculated by the following formula:

Cell viability (%)=(fluorescence value of test well—fluorescence value of negative control well)/(fluorescence value of vehicle control-fluorescence value of negative control group)×100%

The IC50 was calculated using the nonlinear regression data analysis method of Graphpad Prism 6.0 software (Golden software, Golden, Colo., USA).

For the combination test, the cell viability was calculated by normalizing the average OD value of 3 duplicate wells of the single drug control. By comparing the 1050 of the combination curve with the single drug curve, the synergistic effect of two compounds was determined by the observation of whether the curve of the combination group was shifted left.

(2) Evaluation Method of In Vivo Pharmacodynamics Experimental

A subcutaneous xenograft tumor model of human tumor immunodeficient mice was established by cell inoculation (see: Gould S E et al. Translational value of mouse models in oncology drug development. Nature medicine. 2015 21, 431-439; and, Souers A J et al. ABT-199, a potent and selective BCL-2 inhibitor, achieves antitumor activity while sparing platelets. Nature medicine. 2012 19.202-208): tumor cells in logarithmic growth phase were collected, counted and resuspended in 1×PBS, and the cell suspension concentration was adjusted to 2.5-5×107/mL. Using a 1 mL syringe (4 gauge needle), the tumor cells were inoculated subcutaneously in the right side of immunodeficient mice, 5-10× 106/0.2 mL/mouse (experimental animals were purchased from Beijing Vital River Laboratory Animal Technology Co., Ltd. SCXK (Beijing) 2016-0006). All animal experiments were strictly in accordance with the laboratory animal use and management practices of GenePharma Co., Ltd. and Ascentage Pharma Group Co., Ltd. The calculation of relevant parameters referred to the Chinese CFDA "Guidelines for Non-Clinical Research Techniques of Cytotoxic Antitumor Drugs".

Animal body weight and tumor size were measured twice a week during the experiment. The conditions and death of the animals were observed every day. Routine monitoring included the effects of tumor growth and treatment on normal animal behaviors, including activity, feeding and drinking situations, weight gain or loss, eyes, coat and other abnormalities in the experimental animals. The deaths and clinical symptoms observed during the experiment were recorded in the raw data. The entire operations of administration, measurement of mouse body weight and tumor volume were performed in a clean bench. Plasma and tumor tissues were collected, weighed and photographed after the end of the last administration according to the experimental protocol. Plasma and tumor samples were frozen and stored at −80° C.

Tumor volume (TV) was calculated as: TV=a×b2/2, in which a and b represented the length and width of the tumor as measured, respectively. The relative tumor volume (RTV) was calculated as: RTV=Vt/V1, in which V1 was the tumor volume at the time of grouping and administration, and Vt was the tumor volume measured on a day after administration. The evaluation index of anti-tumor activity was the relative tumor proliferation rate T/C (%), which was calculated as: relative tumor proliferation rate T/C (%)=(TRTV/CRTV)×100%, in which TRTV was the RTV of the treatment group, CRTV was the RTV of the vehicle control group; tumor remission rate (%) was calculated as: (the number of SD (stable disease), PR (tumor partial regression) and CR (tumor complete regression) in the tumor-bearing mice after treatment)/the total number of mice in the group× 100%.

Change of body weight %=(measured body weight−
body weight at the time of grouping)/body
weight at the time of grouping×100%.

Evaluation criteria of therapeutic efficiency: according to the Chinese CFDA "Technical guidelines for non-clinical research on cytotoxic antitumor drugs" (November 2006), it was determined as effective when the T/C (%) value was ≤40% and statistic analysis showed p<0.05; and a dose of the drug was considered to be severely toxic when the body weight of the mice dropped by more than 20% or the rate of drug-related deaths exceeded 20%.

The synergistic analysis was performed by the following formula (Gould S E et al. Translational value of mouse models in oncology drug development. Nature medicine. 2015 21, 431-439): synergy factor=((A/C)×(B/C))/(AB/C); A=RTV value of the group administered with A only; B=RTV value of the group administered with B only; C=RTV value of the vehicle control group; AB=RTV value of the group administered with A and B in combination (Clarke R. Issues in experimental design and endpoint analysis in the study of experimental cytotoxic agents in vivo in breast cancer and other models [J]. Breast Cancer Research & Treatment, 1997, 46(2-3): 255-278). If the synergy factor was >1, there was a synergistic effect; if the synergistic factor=1, there was an additive effect; if the synergistic factor<1, there was an antagonistic effect.

Example 2. Preparation of Exemplary Compounds as Bcl-2 Inhibitors (Compounds 3, 6 and 13)

(1) Synthesis of 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide (Compound 3)

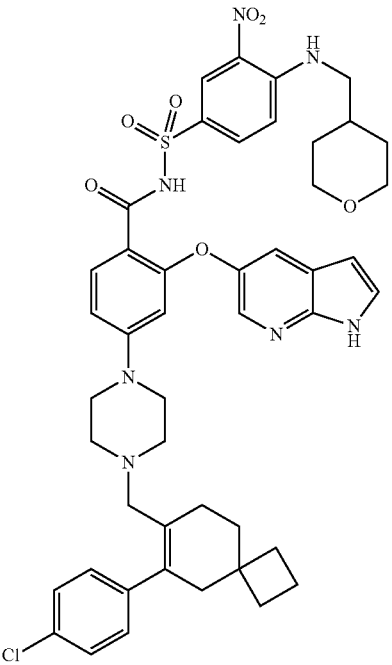 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1]

A mixture of 2-((1H-pyrrolo[2,3-b]pyridin-5-yl)oxy)-4-(4-((6-(4-chlorophenyl) spiro[3.5]non-6-en-7-yl)methyl)piperazin-1-yl)benzoic acid (1.75 g, 3 mmol), 3-nitro-4-(((tetrahydro-2H-pyran-4-yl)methyl)amino) benzenesulfonamide (1.43 g, 4.5) reacted in EDCI (1.15 g, 6 mmol) and 4-(N,N-dimethylamino)pyridine (550 mg, 4.5 mmol) and dichloromethane (40 ml) at room temperature overnight, and then water was added. The aqueous layer was extracted with dichloromethane. The combined organic layers were washed with brine, concentrated and purified with silica column to obtain 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide (1.7 g, 64.4%) was obtained as a yellow solid.

1H NMR (400 MHz, methanol-d4) δ 8.70 (d, J=2.3 Hz, 1H), 8.01 (d, J=2.7 Hz, 1H), 7.87 (d, J=9.2, 2.3 Hz, 1H), 7.66 (d, J=8.9 Hz, 1H), 7.55 (d, J=2.7 Hz, 1H), 7.47 (d, J=3.4 Hz, 1H), 7.38 (d, J=8.4 Hz, 2H), 7.10 (d, J=8.4 Hz, 2H), 6.97 (d, J=9.2 Hz, 1H), 6.77 (dd, J=8.9, 2.4 Hz, 1H), 6.44 (d, J=3.4 Hz, 1H), 6.34 (d, J=2.4 Hz, 1H), 4.02-3.94 (m, 3H), 3.66 (s, 3H), 3.49-3.38 (m, 2H), 3.41-3.25 (m, 7H), 2.42 (s, 3H), 2.26 (s, 3H), 2.00-1.67 (m, 4H), 1.45-1.38 (m, 2H).

(2) Synthesis of (R)—N-((4-(((1,4-dioxan-2-yl)methyl)amino)-3-nitrophenyl) sulfonyl)-2-((1H-pyrrolo[2,3-b]pyridin-5-yl)oxy)-4-(4-((6-(4-chlorophenyl)spiro[3 0.5] non-6-en-7-yl) methyl)piperazin-1-yl)benzamide (Compound 13)

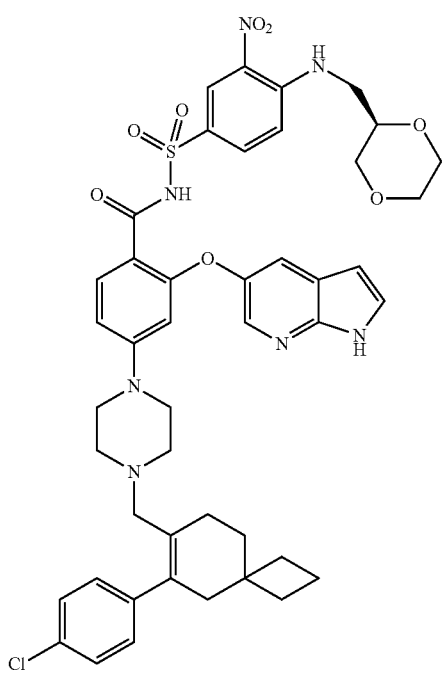 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

The title compound was prepared in a similar manner to that described for the synthesis of Compound 3.

1H NMR (400 MHz, methanol-d4) δ 8.66 (d, J=2.4 Hz, 1H), 7.99 (d, J=2.4 Hz, 1H), 7.84 (dd, J=9.2, 2.4 Hz, 1H), 7.64 (d, J=8.9 Hz, 1H), 7.51 (d, J=2.4 Hz, 2H), 7.45 (d, J=3.3 Hz, 1H), 7.37 (d, J=8.4 Hz, 2H), 7.10 (d, J=8.4 Hz, 2H), 6.94 (d, J=9.2 Hz, 1H), 6.76 (dd, J=8.9, 2.3 Hz, 1H), 6.40 (d, J=3.3 Hz, 1H), 6.36 (d, J=2.3 Hz, 1H), 3.87 (dd, J=11.8, 4.2 Hz, 3H), 3.83-3.70 (m, 3H), 3.67 (s, 2H), 3.62 (dd, J=11.7, 2.9 Hz, 1H), 3.51-3.41 (m, 2H), 3.40-3.35 (m, 1H), 3.29 (dq, J=3.2, 1.6 Hz, 1H), 2.41 (s, 2H), 2.26 (s, 2H), 2.00-1.77 (m, 6H).

Similarly, Compound 6 was prepared similarly according to the method described for the synthesis of Compound 13, with specific reference to WO 2018/027097.

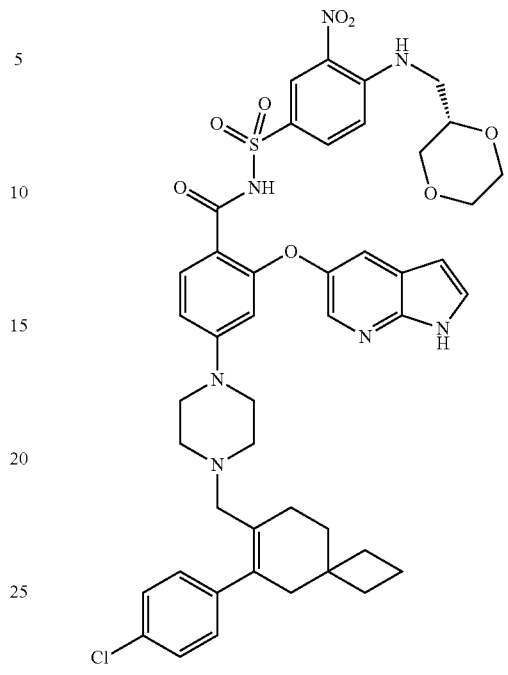

Compound 6

Example 3. Effect of Compound 6 Alone and the Combination of Compound 6 and APG-115 on Different Malignant Tumor Cells (1) The experimental method was as described in Section (1) of Example 1. Cell viability (%) values of Compound 6 alone and the combination of Compound 6 and APG-115 in the following malignant tumor cells were determined in the CTG experiment: OCI-AML-3 (acute myeloid leukemia (AML)), MV-4-11 (acute myeloid leukemia (AML)), KMS-26 (multiple myeloma (MM)), KMS-11 (multiple myeloma (MM)).

(2) Experimental Results

As shown in FIG. 1, in a variety of hematological malignant cells (including AML and MM cells), when Compound 6 was administered in combination with the MDM2 inhibitor APG-115, the inhibitory effect on proliferation of tumor cells was enhanced.

Specifically, in OCI-AML-3 (AML), the $IC_{50}$ of Compound 6 alone for inhibition of proliferation was 10.24, the IC50 of APG-115 alone for inhibition of proliferation was 2.374, and the IC50 values of Compound 6 in combination with APG-115 (10 μM, 3.3 μM, 1 μM) for inhibition of proliferation were 0.143, 0.470 and 1.432, respectively; in MV-4-11 (AML), the IC50 of Compound 6 alone for inhibition of proliferation was 0.0847, the IC50 of APG-115 alone for inhibition of proliferation was 1.955, and the $IC_{50}$ values of Compound 6 in combination with APG-115 (10 μM, 3.3 μM, 1 μM) for inhibition of proliferation were 0.012, 0.013 and 0.017, respectively; in KMS-26 (MM), the $IC_{50}$ of Compound 6 alone for inhibition of proliferation was 14.65, while the $IC_{50}$ values of Compound 6 in combination with APG-115 (10 μM, 3.3 μM, 1 μM) for inhibition of proliferation were 3.407, 8.126 and 12.14, respectively; in KMS-11 (MM), the $IC_{50}$ of Compound 6 alone for inhibition of proliferation was 10.81, while the $IC_{50}$ values of Compound 6 in combination with APG-115 (10 µM, 3.3 µM, 1 µM) for inhibition of proliferation were 0.927, 8.872 and 10.95, respectively.

(3) Summary

Thus, in the in vitro experiment, when Compound 6 was used in combination with MDM2 inhibitor APG-115, the in vitro anti-proliferative activity to hematological malignancies was enhanced, showing a decrease in IC50 value after combination therapy. The comparison of IC50 was performed with the curves of combination administration and the curves of single administration, and it was observed that the curves of combination administration showed left shift. Therefore, the combination of Compound 6 and APG-115 had a synergistic effect.

Example 4. Effects of Compound 6 or APG-115 Alone or a Combination Thereof in Human RS4;11 ALL Mouse Xenograft Tumor Model (1) The experimental method was as described in Section (2) of Example 1. RS4;11 carried wild-type p53 and was an ideal model for evaluating the anti-tumor effect of MDM2 inhibitors. Therefore, a mouse xenograft tumor model was established with RS4;11 tumor cell line (see: Gould S E et al. Translational value of mouse models in oncology drug development. Nature medicine. 2015 21, 431-439. and Souers A J et al. ABT-199, a potent and selective BCL-2 inhibitor, achieves antitumor activity while sparing platelets. Nature medicine. 2012 19.202-208), and in vivo anti-tumor effect of Compound 6 in combination with APG-115 was evaluated.

(2) Experimental Results

Figure 2:
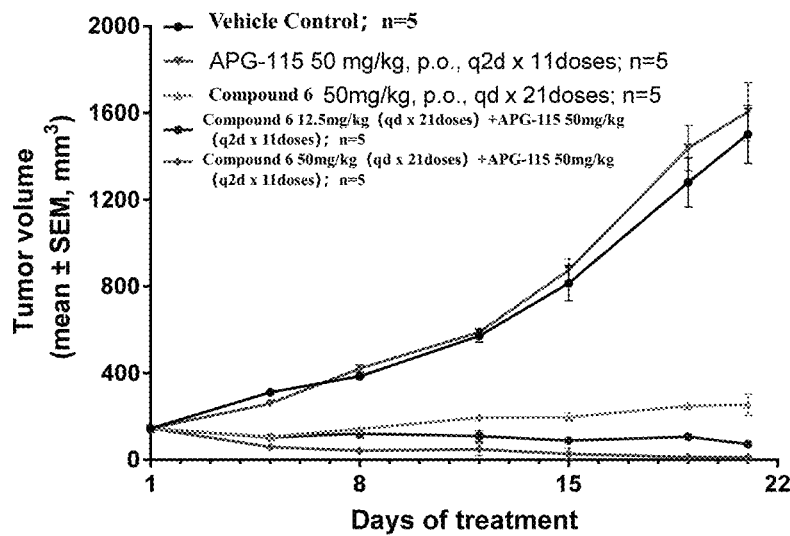
FIG. 2 shows the anti-tumor effect (A) and body weight change (B) of Compound 6 alone or in combination with APG-115 in a human RS4;11 (ALL) mouse xenograft tumor model.
Figure 2:
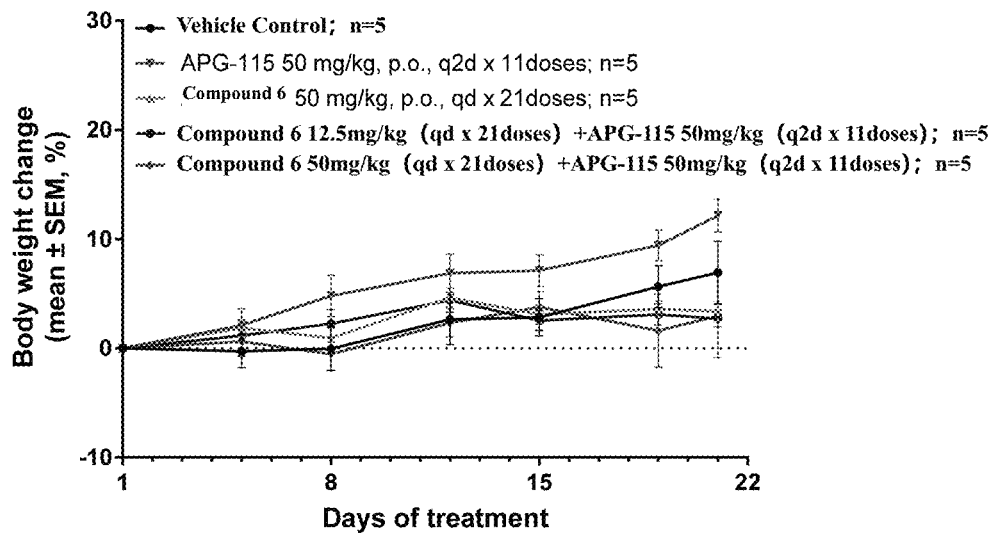

In this model, APG-115 showed no tumor growth inhibition effect after 21 days of administration at a dose of 50 mg/kg, q2d regimen; whereas Compound 6 showed excellent antitumor effect in this model at a dose of 50 mg/kg, qd regimen, and a T/C value of 17% (FIG. 2A, Table 1) at the end of administration (d21). Compound 6 at a dose of 12.5 or 50 mg/kg (qd) in combination with APG-115 (50 mg/kg, q2d) produced significant synergistic effects, and the two combination groups showed T/C values of 5% (P<0.01) and 1% (P<0.01), respectively, and tumor remission rate of 100%, at the end of administration (d21).

(3) Summary

Each of Compound 6 (50 mg/kg) and APG-115 (50 mg/kg) alone did not achieve CR (complete tumor regression) in the RS4;11 model. However, at a well tolerated dose of 12.5 or 50 mg/kg, the combination of Compound 6 and APG-115 was able to achieve partial tumor regression (PR) and complete tumor regression (CR) in the RS4;11 model. Compound 6 in combination with APG-115 had no significant side effects (FIG. 2B), but significantly increased the antitumor effect of single drug in human RS4; 11 ALL mouse xenograft tumor model, and showed synergistic effect (when Compound 6 at dose of 50 mg/kg was combined with APG-115, the synergistic factor was 26.5, much larger than 1). Therefore, the combination of Compound 6 and APG-115 may clinically benefit patients with acute lymphoblastic leukemia (ALL).

Example 5. Effects of Compound 6 or APG-115 Alone or a Combination Thereof in Human OCI-AML-3 AML Mouse Xenograft Tumor Model (1) The experimental method was as described in Section (2) of Example 1. In the in vitro cell proliferation assay, the synergistic anti-proliferative activity of Compound 6 in combination with APG-115 was observed in the OCI-AML-3 tumor cell line. Therefore, a mouse xenograft tumor model was further established using the OCI-AML-3 tumor cell line to evaluate the in vivo anti-tumor effects of Compound 6 and APG-115.

OCI-AML-3 cells (purchased from ATCC) highly expressed MCL-1 (an anti-apoptotic protein), were not sensitive to Compound 6 alone, and belonged to the primary BCL-2 inhibitor-resistant strain. The OCI-AML-3 model grew faster (see: Gould S E et al. Translational value of mouse models in oncology drug development. Nature medicine. 2015 21, 431-439; and, Andresen V et al. Antiproliferative activity of the NPM1 interacting natural product avrainvillamide in acute myeloid leukemia. Cell death and disease (2016) 7, e2497.), and on the 11th day after administration, the average tumor volume of the vehicle control group and the monotherapy groups exceeded the humane endpoint (2000 mm3), and therefore, the experiment was terminated on the 11th day after administration.

TABLE 1

Antitumor effects of Compound 6 alone or in combination with APG-115 in human RS; 11 (ALL) mouse xenograft tumor model

| Treatment | RTV on day 21 after administration (mean ± standard error) | T/C (%) on day 21 after administration | Synergistic factor on day 21 after administration | Tumor remission rate %$^a$ on day 21 after administration |
|---|---|---|---|---|
| Vehicle control | 10.5 ± 1.1 | — | — | 0/5 CR, 0/5 PR (0%) |
| APG-115 50 mg/kg | 11.1 ± 0.9 | 106 | — | 0/5 CR, 0/5 PR (0%) |
| Compound 6 50 mg/kg | 1.8 ± 0.4** | 17 | — | 0/5 CR, 1/5 PR (20%) |
| Compound 6 12.5 mg/kg + APG-115 | 0.5 ± 0.1**,## | 5 | — | 0/5 CR, 5/5 PR (100%) |
| Compound 6 50 mg/kg + APG-115 | 0.1 ± 0.00**,##,+ | 1 | 26.5 | 3/5 CR, 2/5 PR (100%) |

**p < 0.01, compared with vehicle control group;
p < 0.01, compared with APG-115 group;
+p < 0.05, compared with Compound 6 group;
$^a$remission including CR, PR, and SD.

(2) Experimental Results

Figure 3:
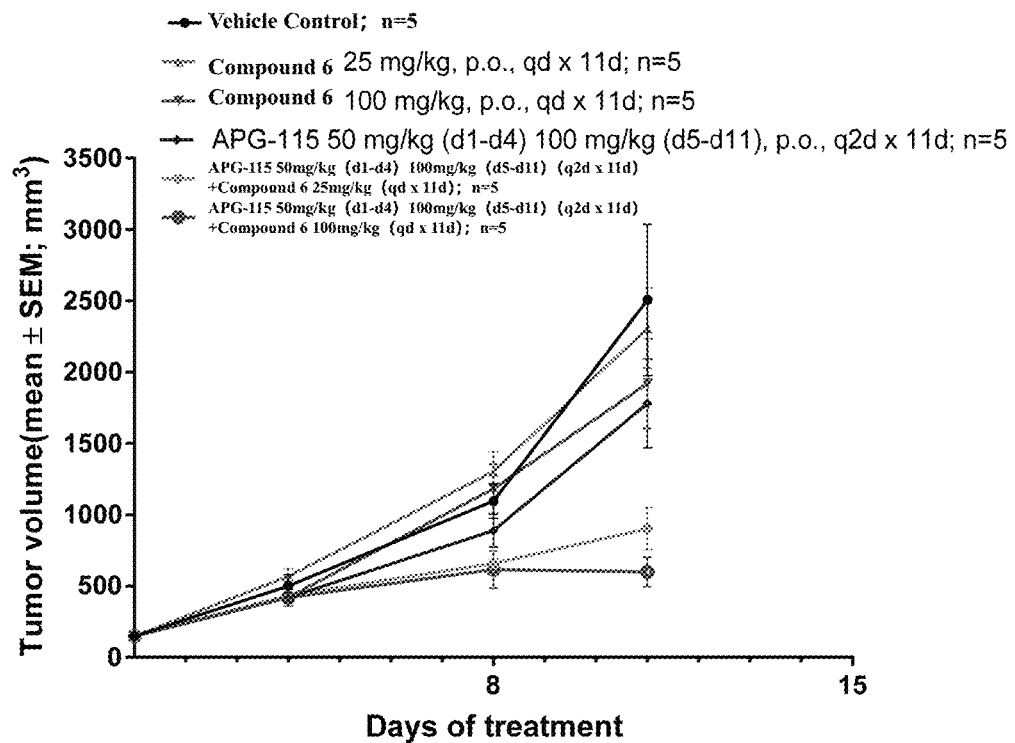
FIG. 3 shows the anti-tumor effect (A) and body weight change (B) of Compound 6 alone or in combination with APG-115 in a human OCI-AML-3 (AML) mouse xenograft tumor model.
Figure 3:
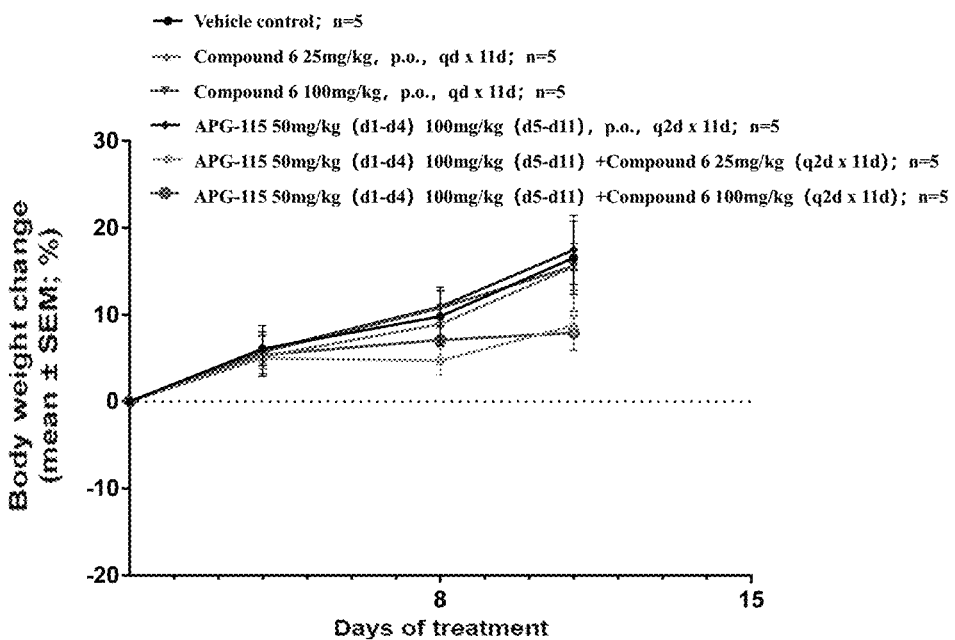

As shown in FIG. 3A and Table 2, Compound 6 at a dose of 25 mg/kg or 100 mg/kg qd regimen did not exhibit tumor growth inhibition after 11 days of administration. APG-115 at doses of 100 mg/kg (d1-d4) and 50 mg/kg (d5-d11) q2d regimen did not exhibit tumor growth inhibition after 11 days of administration as well. However, Compound 6 at a dose of 25 or 100 mg/kg (qd) in combination with APG-115 (100 mg/kg, q2d) produced synergistic effects, and the T/C values of two combination groups reached 36% (P<0.05) and 23% (P<0.01), respectively, at the end of administration (d11).

TABLE 2

Antitumor effects of Compound 6 alone or in combination with APG-115 in human OCI-AML-3 (AML) mouse xenograft tumor model

| Treatment | RTV on day 11 after administration | T/C (%) value on day 11 after administration | Synergistic factor on day 11 after administration |
|---|---|---|---|
| Vehicle group | 18.0 ± 4.9 | — | — |
| Compound 6, 25 mg/kg | 16.2 ± 2.3 | 90 | — |
| Compound 6, 100 mg/kg | 13.0 ± 1.9 | 72 | — |
| APG-115 50 mg/kg | 12.5 ± 2.5 | 69 | — |
| APG-115, 50 mg/kg + Compound 6, 25 mg/kg | 6.5 ± 1.6* | 36 | 1.72 |
| APG-115, 50 mg/kg + Compound 6, 100 mg/kg | 4.1 ± 0.5** | 23 | 2.20 |

*p < 0.05;
**p < 0.01, compared with vehicle control group;
synergistic factor > 1, synergistic effect; synergistic factor = 1, additive effect; synergistic factor < 1, antagonistic effect.

(3) Summary

The combination of Compound 6 and APG-115 was significantly superior to the administration of Compound 6 alone or APG-115 alone. Compound 6 in combination with APG-115 had no significant side effects (FIG. 3B), could significantly increase the antitumor effects of the single agent in the human OCI-AML-3 (AML) mouse xenograft tumor model, and had a significant synergistic effect (when APG-115 was administered in combination with 25 or 100 mg/kg of Compound 6, the synergistic factors were 1.72 or 2.20, respectively, both greater than 1). Therefore, the combination of Compound 6 and APG-115 may clinically benefit patients with acute myeloid leukemia (AML).

Example 6. Antitumor Effect of APG-115 Plus Compound 6 in Human MV-4-11 AML Xenografts (1) The experimental method was as described in Section (2) of Example 1. Compound 6 is a selective BCL-2 inhibitor developed by the Ascentage Pharma Group. The agent is currently under clinical development for cancer therapy both in China and in the US. Enhanced antiproliferation activity of APG-115 in combination with compound 6 has been observed in cell-based assay in AML cell lines in vitro. Accordingly, the synergistic anti-leukemia effects of compound 6 and APG-115 were further evaluated in vivo by using MV-4-11AML xenograft model.

(2) Experimental Results

Figure 4:
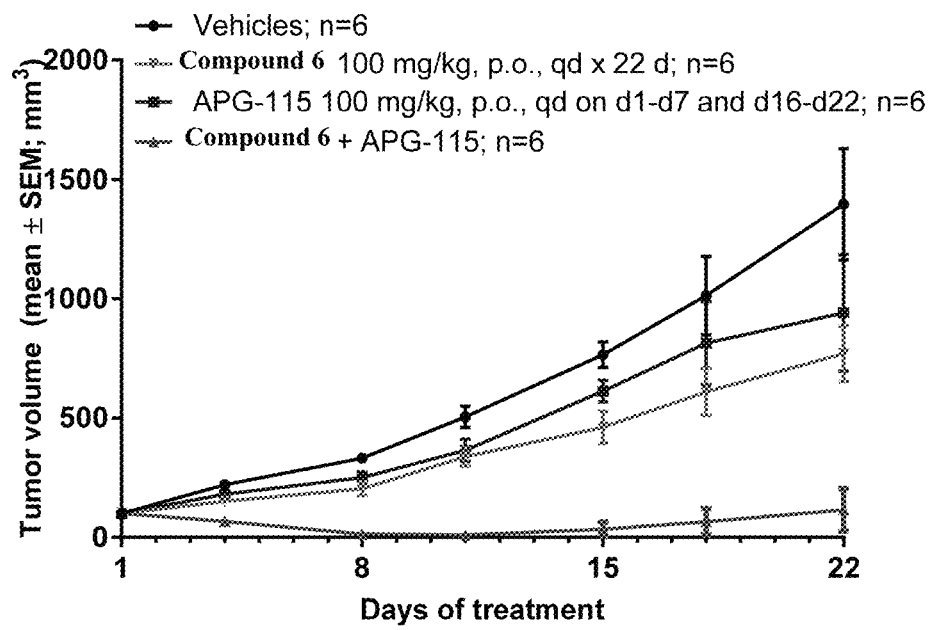
FIG. 4 shows antitumor activity (A) and body weight changes (B) of APG-115 in combination with compound 6 in the treatment of MV-4-11 AML xenograft in Balb/c nude mice.
Figure 4:
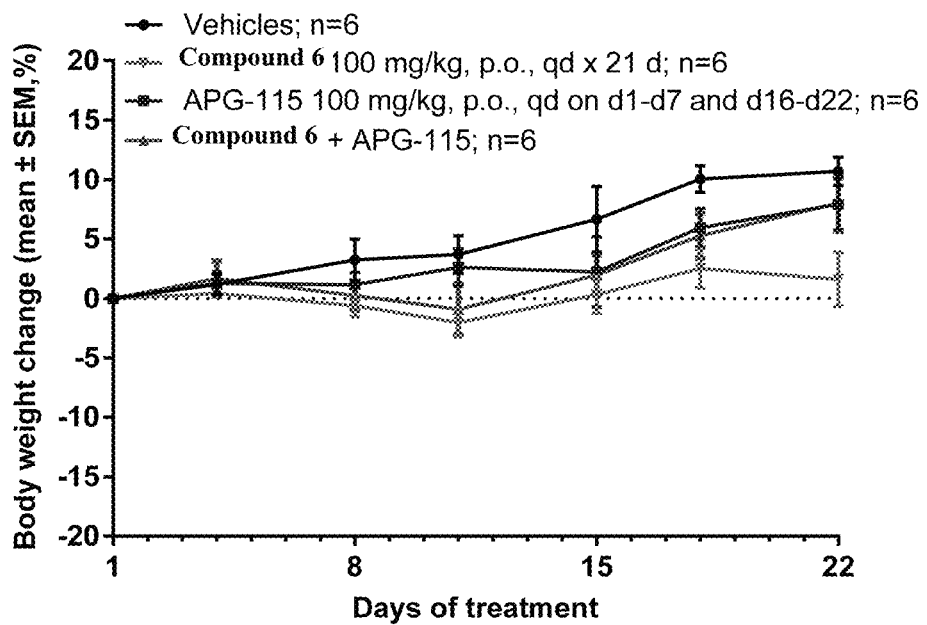

As shown in FIG. 4A and Table 3, compound 6 administered at a dose of 100 mg/kg, p.o., qd×22 d, achieved a T/C value of 55.1% on day 22. APG-115 administered orally at a dose of 100 mg/kg daily on d1-7 and d16-22, achieved a T/C value of 67.1%. Moreover, combined treatment with APG-115 and compound 6 achieved a T/C value of 9.1%, which was statistically significant compared with the vehicle control group and either single agent treatment groups. The synergy ratio was 4.06, indicating that the combination of the two drugs has strong synergistic anti-AML effects. Combination treatment with APG-115 and compound 6 was able to achieve 100% response rates, with five complete tumor regression (CR, 83.3%) and one stable disease (SD, 16.7%) responses at the end of treatment. No significant weight loss was observed during all treatments (FIG. 4B).

TABLE 3

Antitumor activity of APG-115 in combination with compound 6 in the treatment of MV-4-11 AML xenograft in Balb/c nude mice

| Treatment | RTV @ D 22 | T/C (%) @ D 22 | Synergy ratio @ D 22 | Response rate @D 22 | Best response rate |
|---|---|---|---|---|---|
| Vehicles | 13.7 ± 2.2 | — | — | 6/6 mPD | 6/6 mPD |
| compound 6 100 mg/kg | 7.5 ± 0.9 | 55.1 | — | 6/6 mPD | 6/6 mPD |
| APG-115 100 mg/kg | 9.2 ± 2.3 | 67.1 | — | 6/6 mPD | 6/6 mPD |
| compound 6 + APG-115 | 1.2 ± 1.0***$ | 9.1 | 4.06 | 2/6 mCR, 2/6 mPR, 1/6 mSD, 1/6 mPD | 5/6 mCR, 1/6 mSD |

***P < 0.001 vs. vehicle control group;
$P < 0.001 vs. APG-115 group;
Ratio > 1, Synergistic; Ratio = 1, Additive; Ratio < 1, Antagonistic.
PD, progressive disease; PR, partial regression; CR, complete regression; SD, stable disease.

(3) Summary

In summary, the combination treatment with APG-115 and the selective BCL-2 inhibitor compound 6 have synergistic anti-leukemia effects and deserve further clinical investigations.

Example 7. Antitumor Effect of APG-115 Plus Compound 6 in the Systemic MOLM-13-Luc Human AML Xenograft Model in NOD SCID Mice (1) The combined benefits of APG-115 and compound 6 for the therapy of AML was further evaluated in a difficult-to-treat disseminated MOLM-13-Luc systemic human AML model.

The MOLM-13-Luc tumor cells were maintained in vitro as suspension culture in RPMI 1640 medium supplemented with 10% heat inactivated fetal bovine serum (Gibco product), 100 U/mL penicillin and 100 μg/mL streptomycin, at 37° C. in an atmosphere of 5% CO2 in air. The tumor cells were routinely subcultured twice weekly. The cells growing in an exponential growth phase were harvested and counted for tumor inoculation.

The female NOD SCID mice were pre-treated with 2 times of 150 mg/kg cyclophosphamide, QD, at 24 hours before cell inoculation. Each mouse was inoculated with MOLM-13-Luc tumor cells (2×106/mouse) in 0.2 mL of PBS via tail vein for tumor development.

Animals were selected for grouping on day 3 after tumor implantation when the average bioluminescence measurement reached 3.18×107 photons/sec. A high dose pulse regimen (i.e. 100 mg/kg daily for seven days) was applied for APG-115 in this study.

(2) Experimental Results

Figure 5:
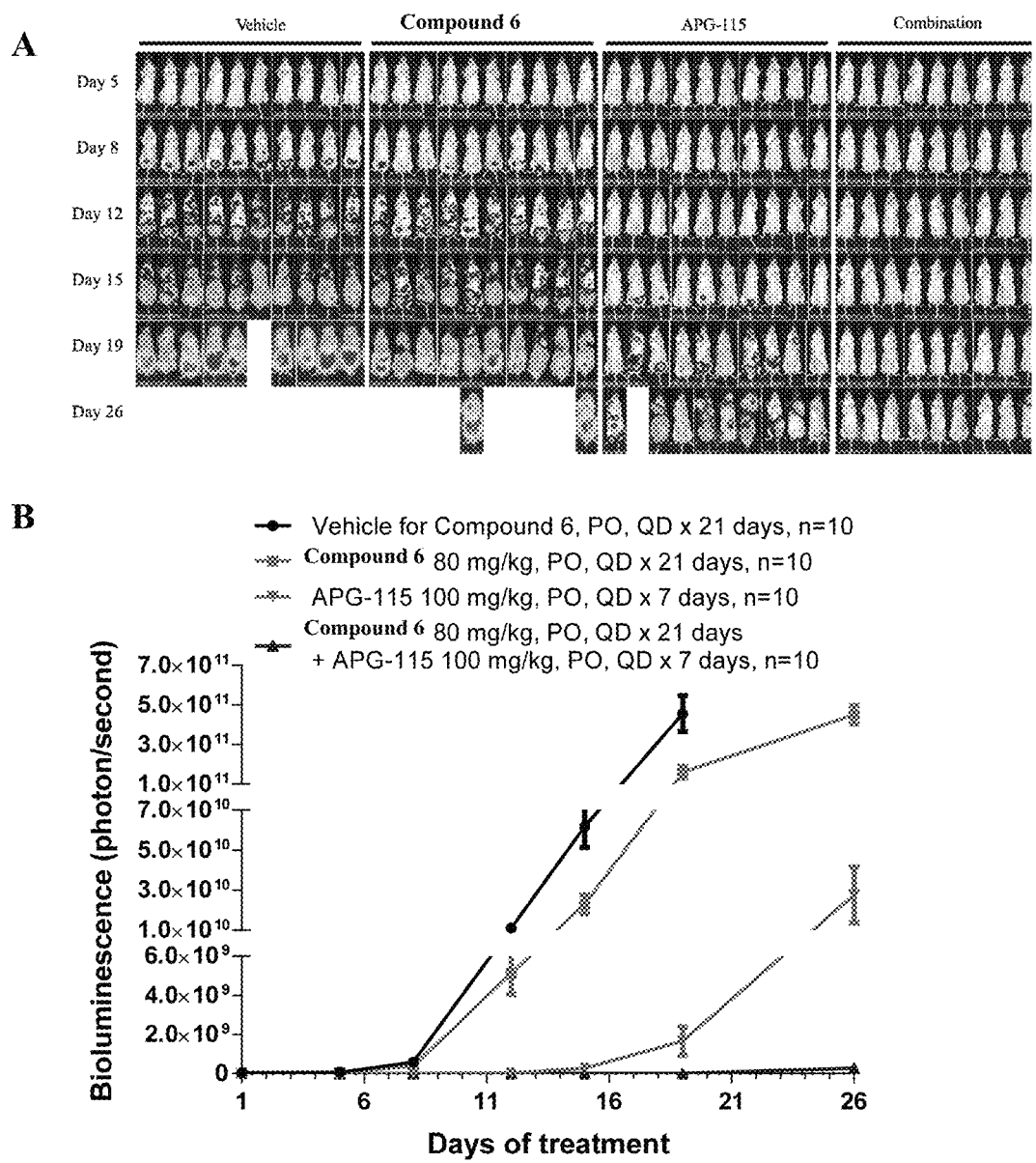
FIG. 5 shows antitumor effect of APG-115 plus compound 6 in the systemic MOLM-13-Luc human AML xenograft model in NOD SCID mice.

As shown in FIG. 5, treatment with compound 6 alone at 100 mg/kg, qd×21 d had limited anti-leukemia activity in this disseminated AML model, as illustrated by the fast increase of bioluminescence signals. Treatment with APG-115 single agent remarkedly decreased bioluminescence signals. Moreover, the combination of APG-115 with compound 6 further reduced bioluminescence signals.

(3) Summary

It is worth noting that the MOLM-13-Luc xenograft model is a diffuse systemic tumor with a higher degree of malignancy and disease progression. These data further demonstrated the superior antileukemia activity of combined treatment with APG-115 and compound 6 for AML therapy.

What is claimed is:

1. A combination comprising:
a Bcl-2 inhibitor of the formula:

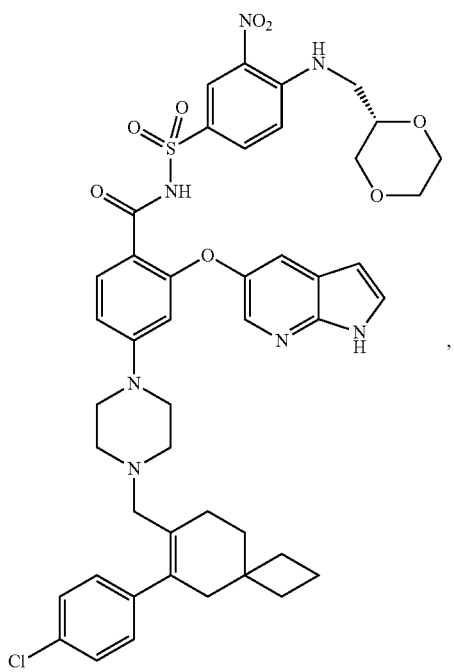 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt or solvate thereof; and
an MDM2 inhibitor of the formula:

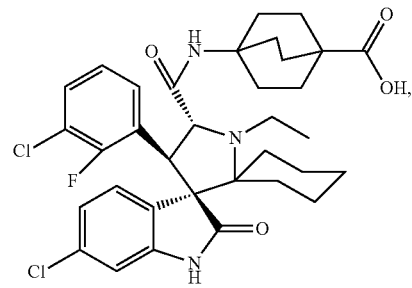 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

or a pharmaceutically acceptable salt or solvate thereof.

2. The combination according to claim 1, wherein the combination is in the form of a pharmaceutical composition.

3. The combination according to claim 1, wherein the Bcl-2 inhibitor and the MDM2 inhibitor are each in a separate preparation.

4. The combination according to claim 1, wherein the Bcl-2 inhibitor and the MDM2 inhibitor are administered or sequentially.

5. The combination according to claim 1, further comprising a pharmaceutically acceptable carrier, diluent or excipient.

6. The combination according to claim 1, wherein the combination is in the form selected from the group consisting of tablet, capsule, granule, syrup, powder, lozenge, sachet, cachet, elixir, suspension, emulsion, solution, syrup, aerosol, ointment, cream, and injection.

7. A method of treating a cancer, comprising administering to a subject in need thereof a therapeutically effective amount of: (i) a Bcl-2 inhibitor of the formula:

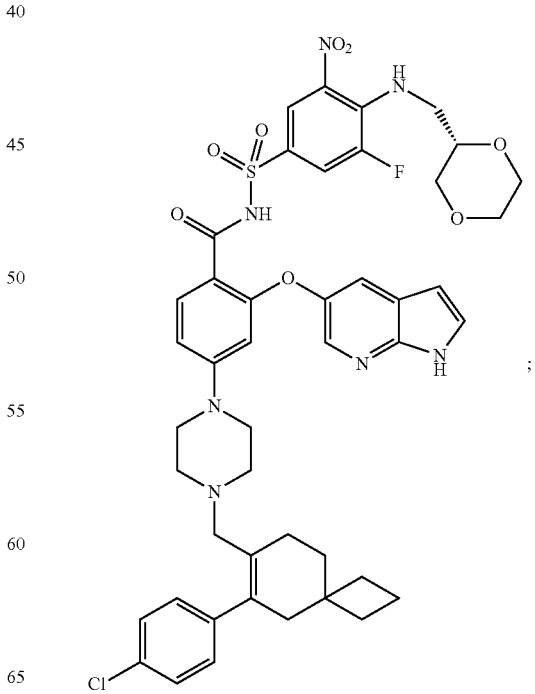

or a pharmaceutically acceptable salt or solvate thereof;
and (ii) an MDM2 inhibitor of the formula:

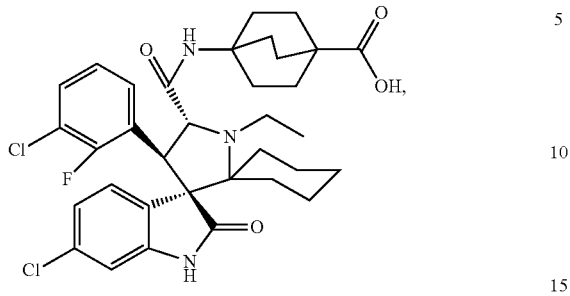

or a pharmaceutically acceptable salt or solvate thereof.

8. The method according to claim 7, wherein the cancer is selected from the group consisting of non-Hodgkin's lymphoma (NHL), diffuse large B-cell lymphoma (DLBCL), follicular lymphoma (FL), acute myeloid leukemia (AML), acute lymphoblastic leukemia (ALL), chronic lymphocytic leukemia (CLL), multiple myeloma (MM), and non-small cell lung cancer (NSCLC).

9. The method according to claim 7, wherein the Bcl-2 inhibitor or a pharmaceutically acceptable salt or solvate thereof is administered in an amount of from about 0.0025 to 1500 mg/day.

10. The method according to claim 7, wherein the MDM2 inhibitor or a pharmaceutically acceptable salt or solvate thereof is administered in an amount of from about 0.005 to 500 mg/day.

* * * * *

UNITED STATES PATENT AND TRADEMARK OFFICE
CERTIFICATE OF CORRECTION

PATENT NO. : 11,478,469 B2  
APPLICATION NO. : 16/648590  
DATED : October 25, 2022  
INVENTOR(S) : Dajun Yang Page 1 of 1

It is certified that error appears in the above-identified patent and that said Letters Patent is hereby corrected as shown below:

In the Claims

Column 110, Line 26, delete "or"; and

Column 110, Lines 40-65, delete

" 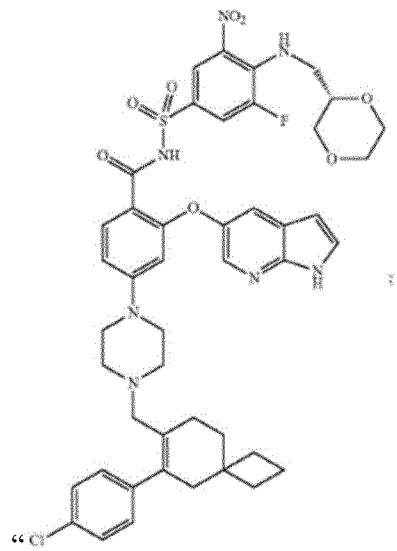 " and insert therefor -- 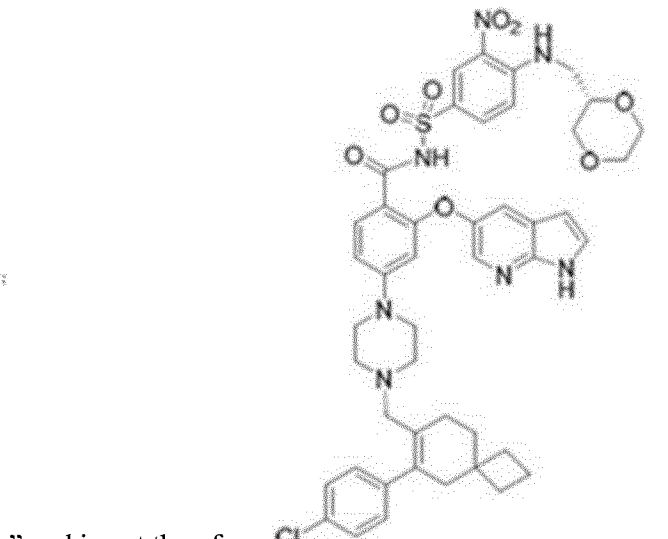 --.

Signed and Sealed this  
Third Day of January, 2023

Katherine Kelly Vidal  
*Director of the United States Patent and Trademark Office*